United States Patent [19]

Bernhard et al.

[11] Patent Number: 5,416,202

[45] Date of Patent: May 16, 1995

[54] MATERIALS COMPRISING AND METHODS OF PREPARATION AND USE FOR RIBOSOME-INACTIVATING PROTEINS

[75] Inventors: Susan L. Bernhard, Menlo Park; Marc D. Better, Los Angeles; Steve F. Carroll, Walnut Creek; Julie A. Lane, Castro Valley; Shau-Ping Lei, Los Angeles, all of Calif.

[73] Assignee: XOMA Corporation, Berkeley, Calif.

[21] Appl. No.: 988,430

[22] Filed: Dec. 9, 1992

Related U.S. Application Data

[63] Continuation-in-part of Ser. No. 901,707, Jun. 19, 1992, which is a continuation-in-part of Ser. No. 787,567, Nov. 4, 1991, abandoned.

[51] Int. Cl.$^6$ ............... C07H 21/02; C12N 15/70; C12N 1/21
[52] U.S. Cl. ............... 536/23.2; 435/252.33; 435/320.1
[58] Field of Search ............... 536/23.2, 23.6; 435/320.1, 252.3, 252.33

[56] References Cited

U.S. PATENT DOCUMENTS

| | | | |
|---|---|---|---|
| 4,853,871 | 8/1989 | Pantoliano et al. | 436/89 |
| 4,888,415 | 12/1989 | Lambert et al. | 530/388.75 |
| 5,101,025 | 3/1992 | Piazak, Jr. et al. | 435/320.1 |

*Primary Examiner*—Stephanie W. Zitomer
*Attorney, Agent, or Firm*—Marshall, O'Toole, Gerstein, Murray & Borun

[57] ABSTRACT

The present invention provides purified and isolated polynucleotides encoding Type I ribosome-inactivating proteins (RIPs) such as gelonin and analogs of the RIPs having a cysteine available for disulfide bonding to targeting molecules. Vectors comprising the polynucleotides and host cells transformed with the vectors are also provided. The RIPs and RIP analogs are particularly suited for use as components of cytotoxic therapeutic agents of the invention which include gene fusion products and immunoconjugates. Cytotoxic therapeutic agents or immunotoxins according to the present invention may be used to selectively eliminate any cell type to which the RIP component is targeted by the specific binding capacity of the second component of the agent, and are suited for treatment of diseases where the elimination of a particular cell type is a goal, such as autoimmune disease, cancer and graft-versus-host disease.

23 Claims, 9 Drawing Sheets

```
RTA         IFPKQYPIINFTTAGATVQSYTNFIRAVRGRLTTGADVRHEIPVLPNRVG   50
                                *       *
GELONIN     GLD----TVSFSTKGATYITYVNFLNELRVKLKPEGN-SHGIPLLRKKCD   45

RTA         LPINQRFILVELSNHAELSVTLALDVTNAYVVGYRAGNSAYFFHPDNQED   100
                                         *
GELONIN     DP-GKCFVLVALSNDNGQLAEIAIDVTSVYVVGYQVRNRSYFF----KDA   90

RTA         AEAITHLFTDVQNRYTFAFGGNYDRLEQLAGNLRENIELGNGPLEEAISA   150
                                  *                    *
GELONIN     PDAAYEGLFKNTIKTRLHFGGTYPSLEG-EKAYRETTDLGIEPLRIGIKK   139

RTA         LYYYSTGGTQLPTLARSFIICIQMISEAARFQYIEGEMRTRIRYNRRSAP   200
                                      ** *
GELONIN     LDENAIDNYKPTEIASSLLVVIQMVSEAARFTFIENQIRNN--FQQRIRP   187

RTA         DPSVITLENSWGRLSTAIQESN-QGAFASPIQLQRRNGSKFSVYDVSILI   249
                      *
GELONIN     ANNTISLENKWGKLSFQIRTSGANGMFSEAVELERANGKKYYVTAVDQVK   237

RTA         PIIALMVYRCAPPPSSQF                                   267
GELONIN     PKIALLKFVDKDPK                                       251
```

FIG. 1

```
RTA     I------FPKQYPIINFTTAGATVQSYTNFIRAVRGRLTTGADVRHEIPV  44
                                  *       *
BRIP    AAKMAKNVDKPLFTATFNVQASSAD-YATFIAGIRNKLRNPAHFSHNRPV  49

RTA     LPN-RVGLPINQRFILVELSNHAELSVTLALDVTNAYVVGYRAGNSAYFF  93
                                            *
BRIP    LPPVEPNVPPSRWFHVVLKASPTSAGLTLAIRADNIYLEGFKSSDGTWWE  99

RTA     HPDNQEDAEAITHLFTDVQNRYTFAFGGNYDRLEQLAGNLRENIELGNGP  143
                                     *
BRIP    LTPGLIPGATYV------------GFGGTYRDLLGDTDKL-TNVALGRQQ  136

RTA     LEEAISALY----YYSTGGTQLPTLARSFIICIQMISEAARFQ----YIE  185
        *                                    ** *
BRIP    LADAVTALHGRTKADKASGPKQQQAREAVTTLVLMVNEATRFQTVSGFVA  186

RTA     GEMRTRIRYNRRSAPDPSVITLENSWGRLSTAIQESNQGAFASPIQLQRR  235
                                 *
BRIP    GLLHPKAVEKKSGKIGNEMKAQVNGWQDLSAALLKTDVKPPPGKSPAKFA  236

RTA     NGSKFSVYDVSILIPIIALMVYRCAP------------PPSSQF        267
BRIP    PIEKMGVRTAEQAANTLGILLFVEVPGGLTVAKALELFHASGGK        280
```

FIG. 2

```
RTA       IFPKQYPIINFTTAGATVQSYTNFIRAVRGRLTTGADVRHEIPVLPNRVG   50
                              *       *
MOMOII    D-------VNFDLSTATAKTYTKFIEDFRATLPFSHKV-YDIPLLYSTIS   42

RTA       LPINQRFILVELSNHAELSVTLALDVTNAYVVGYRAGNSAYFFHPDNQED  100
                                       *
MOMOII    --DSRRFILLDLTSYAYETISVAIDVTNVYVVAYRTRDVSYFF---KESP   87

RTA       AEAITHLFTDVQNRYTFAFGGNYDRLEQLAGNLRENIELGNGPLEEAISA  150
                                *                    *
MOMOII    PEAYNILFKGTR-KITLPYTGNYENLQTAAHKIRENIDLGLPALSSAITT  136

RTA       LYYYSTGGTQLPTLARSFIICIQMISEAARFQYIEGEMRTRIRYNRRSAP  200
                                    ** *
MOMOII    LFYYNAQSA-----PSALLVLIQTTAEAARFKYIERHVAKYVATNFK--P  179

RTA       DPSVITLENSWGRLSTAI--QESNQGAFASPIQLQRRNGSKFSVYDVS--  246
                    *
MOMOII    NLAIISLENQWSALSKQIFLAQNQGGKFRNPVDLIKPTGERFQVTNVDSD  229

RTA       ILIPIIALMVYRCAPPPSSQF                               267

MOMOII    VVKGNIKLLLNSRASTADENFITTMTLLGESVVN                  263
```

FIG. 3

```
RTA       IFPKQYPIINFTTAGATVQSYTNFIRAVRGRLTTGADVRHEIPVLPNRVG  50
                              *       *
LUFFIN    D-------VRFSLSGSSSTSYSKFIGDLRKALPSNGTVYNLTILLSSASG  43

RTA       LPINQRFILVELSNHAELSVTLALDVTNAYVVGYRAGNSAYFFHPDNQED  100
                                       *
LUFFIN    ---ASRYTLMTLSNYDGKAITVAVDVSQLYIMGYLVNSTSYFF---NESD  87

RTA       AEAITHLFTDVQNRYTFAFGGNYDRLEQLAGNLRENIELGNGPLEEAISA  150
                                *                    *
LUFFIN    AKLASQYVFKGSTIVTLPYSGNYEKLQTAAGKIREKIPLGFPALDSALTT  137

RTA       LYYYSTGGTQLPTLARSFIICIQMISEAARFQYIEGEMRTRIRYNRRSAP  200
                                    ** *
LUFFIN    IFHYDSTAA-----AAAFLVILQTTAEASRFKYIEGQIIERI--SKNQVP  180

RTA       DPSVITLENS-WGRLSTAIQ--ESNQGAFASPIQLQRRNGSKFSVYDVSI  247
                     *
LUFFIN    SLATISLENSLWSALSKQIQLAQTNNGTFKTPVVITDDKQQRVEITNVTS  230

RTA       LIPIIALMVYRCAPPPSSQF                                267
LUFFIN    KVVTKNIQLLLNYKQNVA                                  248
```

FIG. 4

```
RTA      IFPKQYPIINFTTAGATVQSYTNFIRAVRGRLTTGADVRHEIPVLPNRVG   50
                             *       *
TRICHO   D-------VSFRLSGATSSSYGVFISNLRKALPNERKL-YDIPLL--RSS   40

RTA      LPINQRFILVELSNHAELSVTLALDVTNAYVVGYRAGNSAYFFHPDNQED   100
                                      *
TRICHO   LPGSQRYALIHLTNYADETISVAIDVTNVYIMGYRAGDTSYFF--NEASA   88

RTA      AEAITHLFTDVQNRYTFAFGGNYDRLEQLAGNLRENIELGNGPLEEAISA   150
                               *                    *
TRICHO   TEAAKYVFKDAMRKVTLPYSGNYERLQTAAGRIRENIPLGLPALDSAITT   138

RTA      LYYYSTGGTQLPTLARSFIICIQMISEAARFQYIEGEMRTRIRYNRRSAP   200
                                   ** *
TRICHO   LFYYNANSA-----ASALMVLIQSTSEAARYKFIEQQIGSRV--DKTFLP   181

RTA      DPSVITLENSWGRLSTAIQ--ESNQGAFASPIQLQRRNGSKFSVYDV--S   246
                   *
TRICHO   SLAIISLENSWSALSKQIQIASTNNGQFESPVVLINAQNQRVTITNVDAG   231

RTA      ILIPIIALMVYRCAPPPSSQF                                267
TRICHO   VVTSNIALLLNRNNMA                                     247
```

FIG. 5

```
RTA    IFPKQYPIINFTTAGATVQSYTNFIRAVRGRLTTGADVRHEIPVLPNRVG                  50
                                          *
MOMOI  D------VSFRLSGADPRSYGMFIKDLRNALPFREKVYNIPLLLPSVSG                   43

RTA    LPINQRFILVELSNHAELSVTLALDVTNAYVVGYRAGNSAYFFHPDNQED                  100
                                      *
MOMOI  ---AGRYLLMHLFNYDGKTITVAVDVTNVYIMGYLADTTSYFFNEPAAEL                   90

RTA    AEAITHLFTDVQNRYTFAFGGNYDRLEQLAGNLRENIELGNGPLEEAISA                  150
                                *
MOMOI  ASQ--YVFRDARRKITLPYSGNYERLQIAAGKPREKIPIGLPALDSAIST                  138

RTA    LYYYSTGGTQLPTLARSFIICIQMISEAARFQYIEGEMRTRIRYNRRSAP                  200
                                       ** *
MOMOI  LLHYDSTAA-----AGALLVLIQTTAEAARFKYIEQQIQERA--YRDEVP                  181

RTA    DPSVITLENSWGRLSTAIQ--ESNQGAFASPIQLQRRNGSKFSVYDVSIL                  248
                      *
MOMOI  SLATISLENSWSGLSKQIQLAQGNNGIFRTPIVLVDNKGNRVQITNVTSK                  231

RTA    IPIIALMVY---------RCAPPPSSQF                                        267

MOMOI  VVTSNIQLLLNTRNIAEGDNGDVSTTHGFSST                                    263
```

FIG. 6

```
RTA   IFPKQYPIINFTTAGATVQSYTNFIRAVRGRLTTGADVRHEIPVLPNRVG   50
                          *       *
MAP   A-PTLETIASLDLNNPT--TYLSFITNIRTKVADKTE-----QCTIQKIS   42

RTA   LPINQRFILVELSNHAELSVTLALDVTNAYVVGYRA---GNSAYFFHPDN   97
                                   *
MAP   KTFTQRYSYIDLIVSSTQKITLAIDMADLYVLGYSDIANNKGRAFFFKDV   92

RTA   QEDAEAITHLFTDVQNRYTFAFGGNYDRLEQLAGNLRENIELGNGPLEEA   147
                               *                    *
MAP   TEAVANNFFPGATGTNRIKLTFTGSYGDLEK-NGGLRKDNPLGIFRLENS   141

RTA   ISALYYYSTGGTQLPTLARSFIICIQMISEAARFQYIEGEMRTRIRYNRR   197
                                   ** *
MAP   IVNIY---GKAGDVKKQAKFFLLAIQMVSEAARFKYI-SDKIPSEKYEE-   186

RTA   SAPDPSVITLENSWGRLSTAIQESNQGAFASPIQLQRRNGSKFSVYDVSI   247
                   *
MAP   VTVDEYMTALENNWAKLSTAVYNSKPSTTTATKCQLATSPVTISPWIFKT   236

RTA   LIPIIALMVYRCAPPPSSQF                                 267
MAP   VEEIKLVMGLLKSS                                       250
```

FIG. 7

```
RTA   IFPKQYPIINFTTAGATVQSYTNFIRAVRGRLTTGADVRHEIPVLPNRVG  50
                          *       *
PAPS  I-----NTITFDAGNATINKYATFMESLRNEAKDPSLKCYGIPMLPNTNS  45

RTA   LPINQRFILVELSNHAELSVTLALDVTNAYVVGYRAGNSA-----YFFHP  95
                                   *
PAPS  ---TIKYLLVKLQGASLKTITLMLRRNNLYVMGYSDPYDNKCRYHIFNDI  92

RTA   DNQEDAEAITHLFTDVQNRYT--FAFGGNYDRLEQLAG-NLRENIELGNG  142
                                   *
PAPS  KGTEYSDVENTLCPSSNPRVAKPINYNGLYPTLEKKAGVTSRNEVQLGIQ  142

RTA   PLEEAISALYYYSTGGTQLPTLARSFIICIQMISEAARFQYIEGEMRTRI  192
       *                                **  *
PAPS  ILSSDIGKI--SGQGSFTEKIEAKFLLVAIQMVSEAARFKYIENQVKTN-  189

RTA   RYNRRSAPDPSVITLENSWGRLSTAIQESNQGAFASPIQLQRRNGSKFSV  242
                        *
PAPS  -FNRDFSPNDKVLDLEENWGKISTAIHNSKNGALPKPLELKNADGTKWIV  238

RTA   YDVSILIPIIALMVYRCAPPPSSQF                           267
PAPS  LRVDEIKPDVGLLNY--VNGTCQAT                           261
```

FIG. 8

```
RTA    IFPKQYPIINFTTAGATVQSYTNFIRAVRGRLTTGADVRHEIPVLPNRVG   50
                           *       *
SAP6   V-----TSITLDLVNPTAQQYSSFVDKIRNNVKDPNLKYGGTDI--AVIG   43

RTA    LPINQRFILVELSNHAELSVTLALDVTNAYVVGYRAGNS-----AYFFHP   95
                                    *
SAP6   PPSKEKFLRINFQSSRG-TVSLGLKRDNLYVVAYLAMDNTNVNRAYYFRS   92

RTA    DNQEDAEAITHLFTDVQNRYTFAFGGNYDRLEQ-----LAGNLRENIELG   140
                                  *
SAP6   EITSAESTALFPEATTANQKALEYTEDYQSIEKNAQITQGDQSRKELGLG   142

RTA    NGPLEEAISALYYYSTGGTQLPTLARSFIICIQMISEAARFQYIEGEMRT   190
          *                                **  *
SAP6   IDLLSTSMEAV---NKKARVVKDEARFLLIAIQMTAEAARFRYIQNLVIK   189

RTA    RIRYNRRSAPDPSVITLENSWGRLSTAI-QESNQGAFASPIQLQRRNGSK   239
                           *
SAP6   N--FPNKFNSENKVIQFEVNWKKISTAIYGDAKNGVFNKDYDFGFGKVRQ   237

RTA    FSVYDVSILIPIIALMVYRCAPPPSSQF                         267
SAP6   VKDLQMGLL------MYLGKPKSSNEAN                         259
```

FIG. 9

MATERIALS COMPRISING AND METHODS OF PREPARATION AND USE FOR RIBOSOME-INACTIVATING PROTEINS

This application is a continuation-in-part of co-pending U.S. patent application Ser. No. 07/901,707, filed Jun. 19, 1992, which in turn is a continuation-in-part of U.S. patent application Ser. No. 07/787,567, filed Nov. 4, 1991, now abandoned.

BACKGROUND

The present invention relates, in general, to materials useful as components of cytotoxic therapeutic agents. More particularly, the invention relates to polynucleotides encoding ribosome-inactivating proteins, to polynucleotides encoding analogs of ribosome-inactivating proteins specifically modified for conjugation to targeting molecules and to gene fusions of polynucleotides encoding ribosome-inactivating proteins to polynucleotides encoding targeting molecules.

Ribosome-inactivating proteins (RIPs) comprise a class of proteins which is ubiquitous in higher plants. RIPs have also been isolated from bacteria. RIPs are potent inhibitors of eukaryotic protein synthesis. The N-glycosidic bond of a specific adenine base is hydrolytically cleaved by RIPs in a highly conserved loop region of the 28S rRNA of eukaryotic ribosomes thereby inactivating translation.

Stirpe et al., *FEBS Lett.*, 195(1,2), 1–8 (1986) groups plant RIPs into two types. Type I proteins each consist of a single peptide chain having ribosome-inactivating activity, while Type II proteins each consist of an A-chain, essentially equivalent to a Type I protein, disulfide-linked to a B-chain having cell-binding properties. Gelonin, dodecandrin, tricosanthin, tricokirin, bryodin, Mirabilis antiviral protein (MAP), barley ribosome-inactivating protein (BRIP), pokeweed antiviral proteins (PAPs), saporins, luffins and momordins are examples of Type I RIPs, while ricin and abrin are examples of Type II RIPs. Amino acid sequence information is reported for various ribosome-inactivating proteins. It appears that at least the tertiary structure of active sites is conserved among Type I RIPs, bacterial RIPs and A-chains of Type II RIPs and, in many cases, primary structure homology is also found. Ready et al., *J. Biol. Chem.*, 259(24), 15252–15256 (1984) and other reports suggest that the two types of RIPs are evolutionarily related.

Separated from their natural environment, Type I plant ribosome-inactivating proteins may be particularly suited for use as components of cytotoxic therapeutic agents. A RIP may be conjugated to a targeting agent that will deliver the RIP to a particular cell type in vivo in order to selectively kill those cells. Typically, the targeting agent (e.g., an antibody) is linked to the toxin by a disulfide bond which is reduced in vivo allowing the protein toxin to separate from the delivery antibody and become active intracellularly. Another strategy for producing a cytotoxic agent is to express a gene encoding a RIP fused to a gene encoding a targeting moiety. The resulting protein product is a single polypeptide containing an RIP linked to, for example, at least one chain of an antibody. A variety of gene fusion products including protein toxin sequences are discussed in a recent review by Pastan et al., *Science*, 254, 1173–1177 (1991).

Because some RIPs, such as the Type I RIP gelonin, are only available from scarce plant materials, it is desirable to clone the genes encoding the RIPs to enable recombinant production of the proteins. It is also desirable to develop analogs of the natural proteins which may be easily conjugated to targeting molecules while retaining their natural biological activity because most Type I RIPs have no natural sites (i.e. available cysteine residues) for conjugation to targeting agents. Alternatively, it is desirable to develop gene fusion products including Type I RIPs as a toxic moiety and antibody substances as a targeting moiety.

There thus exists a need in the art for cloned genes encoding Type I RIPs, for analogs of Type I RIPs which may be easily conjugated to targeting molecules and for gene fusion products comprising Type I RIPs.

SUMMARY OF THE INVENTION

The present invention provides purified and isolated polynucleotides encoding Type I RIPs, Type I RIPs having a cysteine available for disulfide bonding to targeting molecules and fusion products including Type I RIPs. Vectors comprising the polynucleotides and host cells transformed with the vectors are also provided.

A purified and isolated polynucleotide encoding natural sequence gelonin, and a host cell including a vector encoding gelonin of the type deposited as ATCC Accession No. 68721 are provided. Further provided are a purified and isolated polynucleotide encoding natural sequence barley ribosome-inactivating protein and a purified and isolated polynucleotide encoding momordin II.

Analogs of a Type I plant RIP are defined herein as non-naturally occurring polypeptides that share the ribosome-inactivating activity of the natural protein but that differ in amino acid sequence from the natural protein. Preferred analogs according to the present invention are analogs of Type I plant RIPs each having a cysteine available for disulfide bonding located at a position in its amino acid sequence from the position corresponding to position 251 in SEQ ID NO: 1 to the carboxyl terminal position of the analog. Other preferred analogs according to the invention are Type I RIPs each having a cysteine available for disulfide bonding at a position in the analog that is on the surface of the protein in its natural conformation and that does not impair native folding or biological activity of the ribosome-inactivating protein. Analogs of bacterial RIPs are also contemplated by the present invention.

The present invention provides an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog corresponding to position 259 in SEQ ID No: 1 or at a position in the amino acid sequence in the analog corresponding to a position from the position corresponding to position 251 in SEQ ID NO: 1 to the carboxyl terminal position of the analog.

An analog according to the present invention may be an analog of gelonin. In an analog of gelonin according to the present invention, the cysteine may be at a position in the analog from position 244 to the carboxyl terminal position of the analog, more preferably at a position in the analog from position 247 to the carboxyl terminal position of the analog, and, in these regions, most preferably at position 244, at position 247 or at position 248 of the amino acid sequence of the analog. It is preferred that the gelonin cysteine residues at positions 44 and 50 be replaced with alanine residues.

An analog according to the present invention may be an analog of barley ribosome-inactivating protein. Preferably, a cysteine in such an analog is at a position in the analog from position 256 to the carboxyl terminal position, and more preferably the cysteine is at a position in the amino acid sequence of the analog from position 260 to the carboxyl terminal position of the analog. Most preferably, in these regions, the cysteine is at position 256, at position 270 or at position 277 of the amino acid sequence of the analog.

An analog according to the present invention may be an analog of momordin II.

Analogs according to the present invention may have a cysteine in the amino acid sequence of the analog at a position which corresponds to a position within one amino acid of position 259 of SEQ ID NO: 1. Such an analog may be an analog of gelonin, of barley ribosome-inactivating protein, or of momordin II.

The present invention also provides a polynucleotide encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein, and which cysteine is located at a position in the amino acid sequence of the analog from the position corresponding to position 251 in SEQ ID NO: 1 to the carboxyl terminal position of the analog. The polynucleotide may encode an analog of gelonin, preferably an analog wherein the cysteine is at a position in the amino acid sequence of the analog from position 244 to the carboxyl terminal position of the analog, more preferably wherein the cysteine is at a position in the analog from position 247 to the carboxyl terminal position of the analog, and most preferably the cysteine is at position 244, at position 247 or at position 248 of the amino acid sequence of the analog. It is preferred that a polynucleotide according to the present invention encode a gelonin analog wherein the native gelonin cysteine residues at positions 44 and 50 are replaced with alanine residues.

A polynucleotide according to the present invention may encode an analog of barley ribosome-inactivating protein, preferably an analog wherein the cysteine is at a position in the analog from position 256 to the carboxyl terminal position of the analog, more preferably wherein the cysteine is at a position in the analog from position 260 to the carboxyl terminal position of the analog, and most preferably wherein the cysteine is at position 256, at position 270 or at position 277 of the amino acid sequence of the analog.

A polynucleotide according to the present invention may encode an analog of mormordin II.

The present invention provides a vector including a polynucleotide encoding an analog of a Type I ribosome-inactivating protein, which analog has a cysteine available for intermolecular disulfide bonding at a amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

The present invention further provides a host cell including a DNA vector encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog. In such a host cell the vector may encode an analog of gelonin, especially an analog wherein the cysteine is at position 247 of the amino acid sequence of the analog, such as in the host cell deposited as ATCC Accession No. 69009.

A host cell according to the present invention may include a vector encoding barley ribosome-inactivating protein, especially a host cell wherein the cysteine is at position 277 of the amino acid sequence of the analog such as in the host cell deposited as ATCC Accession No. 68722.

The present invention also provides an agent toxic to a cell including an analog of a Type I ribosome-inactivating protein linked by a disulfide bond through a cysteine to a molecule which specifically binds to the cell, which cysteine is at an amino acid position in the analog corresponding to a position not naturally available for intermolecular disulfide bonding in the Type I ribosome-inactivating protein and which cysteine is located in the amino acid sequence of the analog from the position corresponding to position 251 in SEQ ID NO: 1 to the carboxyl terminal position of the analog. The agent may include an analog of gelonin, preferably an analog wherein the cysteine is at a position in the analog from position 247 to the carboxyl terminal position of the analog, and more preferably wherein the cysteine is at position 247 or 248 of the amino acid sequence of analog. An agent including an analog wherein the native gelonin cysteine residues at positions 44 and 50 are replaced with alanine residues is preferred.

An agent according to the present invention may include an analog of barley ribosome-inactivating protein, preferably an analog wherein the cysteine is at a position in the analog from position 260 to the carboxyl terminal position of the analog, more preferably wherein the cysteine is at a position in the analog from position 270 to the carboxyl terminal position of the analog, and most preferably wherein the cysteine is at position 256, at position 270 or at position 277 of the amino acid sequence of the analog.

An agent according to the present invention may include an analog of momordin II.

The present invention provides an agent wherein the Type I ribosome-inactivating protein is linked to an antibody, particularly to an H65 antibody or to an antibody fragment, more particularly to an antibody fragment selected from the group consisting of chimeric and human engineered antibody fragments, and most particularly to a Fab antibody fragment, a Fab' antibody fragment or a F(ab')$_2$ antibody fragment. It is highly preferred that an agent according to the present invention include a chimeric or human engineered antibody fragment selected from the group consisting of a Fab antibody fragment, a Fab' antibody fragment and a F(ab')$_2$ antibody fragment.

A method according to the present invention for preparing an analog of a Type I ribosome-inactivating protein includes the step of expressing in a suitable host cell a polynucleotide encoding a Type I ribosome-inactivating protein having a cysteine available for intermolecular disulfide bonding substituted (e.g., by site-directed mutagenesis of the natural DNA sequence encoding the RIP or by chemical synthesis of a DAN sequence encoding the RIP analog) at an amino acid position corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

A product according to the present invention may be a product of a method including the step of expressing in a suitable host cell a polynucleotide encoding a Type I ribosome-inactivating protein having a cysteine available for intermolecular disulfide bonding substituted at an amino acid position corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

The present invention provides a method for preparing an agent toxic to a cell including the step of linking an analog of a Type I ribosome-inactivating protein through a cysteine to a molecule which specifically binds to the cell, which analog has the cysteine at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

According to the present invention, a method for treating a disease in which elimination of particular cells is a goal may include the step of administering to a patient having the disease a therapeutically effective amount of an agent toxic to the cells including an analog of a Type I ribosome-inactivating protein linked through a cysteine to a molecule which specifically binds to the cell, the analog having the cysteine at an amino acid position corresponding to a position not naturally available for intermolecular disulfide bonding in the Type I ribosome-inactivating protein and the cysteine being located at a position in the amino acid sequence of the analog from the position corresponding to position 251 in SEQ ID NO: 1 to the carboxyl terminal position of the analog.

The present invention also provides an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

Such an analog may be an analog wherein the Type I ribosome inactivating protein is gelonin, and is preferably an analog of gelonin wherein the cysteine is at position 10 of the amino acid sequence of the analog as encoded in a vector in a host cell deposited as ATCC Accession No. 69008. Other such gelonin analogs include those wherein the cysteine is at a position 60, 103, 146, 184 or 215 in the amino acid sequence of the gelonin analog. It is preferred that the gelonin cysteine residues at positions 44 and 50 be replaced with alanine residues in these analogs.

The present invention further provides an analog of a Type I ribosome-inactivating protein wherein the analog includes only a single cysteine. Such an analog may be an analog of gelonin and is preferably an analog wherein the single cysteine is at position 10, position 44, position 50 or position 247 in the amino acid sequence of the analog, but the cysteine may be located at other positions defined by the invention as well.

The present invention provides a polynucleotide encoding an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

According to the present invention, a method for preparing an analog of a Type I ribosome-inactivating protein may include the step of expressing in suitable host cell a polynucleotide encoding a Type I ribosome-inactivating protein having a cysteine available for intermolecular disulfide bonding substituted at an amino acid position corresponding to a position not naturally available for disulfide bonding in the Type I ribosome-inactivating protein, the cysteine is located at a position corresponding to an amino acid position on the surface of ricin A-chain in its natural conformation and which analog retains ribosome-inactivating activity of the Type I ribosome-inactivating protein.

The present invention provides an agent toxic to a cell including an analog of a Type I ribosome-inactivating protein linked by a disulfide bond through a cysteine to a molecule which specifically binds to the cell, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

A method according to the present invention for preparing an agent toxic to a cell may include the step of linking an analog of a Type I ribosome-inactivating protein through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

A method according to the present invention for treating a disease in which elimination of particular cells is a goal includes the step of administering to a patient having the disease a therapeutically effective amount of an agent toxic to the cells wherein the agent includes an analog of a Type I ribosome-inactivating protein linked by a disulfide bond through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

The RIP analogs are particularly suited for use as components of cytotoxic therapeutic agents. Cytotoxic agents according to the present invention may be used in vivo to selectively eliminate any cell type to which the RIP component is targeted by the specific binding capacity of the second component. To form cytotoxic agents RIP analogs may be conjugated to monoclonal antibodies, including chimeric and CDR-grafted antibodies, and antibody domains/fragments (e.g., Fab, Fab', F(ab')$_2$, single chain antibodies, and Fv or single variable domains) as well as conjugated to monoclonal antibodies genetically engineered to include free cysteine residues are within the scope of the present invention. Examples of Fab' and F(ab')$_2$ fragments useful in the present invention are described in co-pending, co-owned U.S. patent application Ser. No. 07/714,175, filed Jun. 14, 1991 and in International Publication No. WO 89/00999 published on Feb. 9, 1989, which are incorporated by reference herein. RIPs according to the present invention may also be conjugated to targeting agents other than antibodies, for example, lectins which bind to cells having particular surface carbohydrates, or hormones, lymphokines, growth factors or other polypeptides which bind specifically to cells having particular receptors. Immunoconjugates including RIPs may be described as immunotoxins. An immunotoxin may also consist of a fusion protein rather than an immunoconjugate.

The present invention provides gene fusions of an antigen-binding portion of an antibody (e.g., an antibody light chain or truncated heavy chain, or a single chain antibody) or any targeting agent listed in the foregoing paragraph, linked to a Type I RIP. The gene fusions may include an RIP gene linked either at the 5' or the 3' end of an antibody gene. A DNA linker encoding a peptide segment may or may not be inserted between the toxin and the antibody gene. Preferably, the linker encodes a segment of the E. coli shiga-like toxin which contains two cysteine residues participating in a disulfide bond and forming a loop that includes a protease sensitive amino acid sequence (e.g., SEQ ID NO: 58), or a segment of rabbit muscle aldolase which contains several potential cathepsin cleavage sites (e.g., SEQ ID NO: 59). The Type I RIP portion of the fused genes preferably encodes gelonin, BRIP or momordin II. Also preferably, the antibody portion of the fused genes comprises sequences encoding one of the chains of an antibody Fab fragment (i.e., kappa or Fd) and the fused gene is co-expressed in a host cell with the other Fab gene, or the antibody portion comprises sequences encoding a single chain antibody.

The present invention also provides a method for purifying an protein or immunotoxin comprising a ribosome-inactivating protein and a portion of an antibody including the steps of passing a solution containing the protein through an anion exchange column; applying the flow-through to a protein G column; and eluting the protein from the protein G column. The method may further comprise the steps of introducing the flow-through of the anion exchange column into a cation exchange column; exposing the cation exchange column to an eluent effective to elute said protein; and then applying the eluted protein to a protein G column, rather than applying the anion exchange column flow-through directly to a protein G column.

Immunotoxins according to the present invention including immunoconjugates and fusion proteins are suited for treatment of diseases where the elimination of a particular cell type is a goal, such as autoimmune disease, cancer and graft-versus-host disease. The immunotoxins are also suited for use in causing immunosuppression and in treatment of infections by viruses such as the Human Immunodeficiency Virus.

Specifically illustrating polynucleotide sequences according to the present invention are the inserts in the plasmid pING3731 in E. coli MC1061 (designated strain G274) and in the plasmid pING3803 in E. coli E104 (designated strain G275), both deposited with the American Type Culture Collection (ATCC), 12301 Parklawn Drive, Rockville, Md., on Oct. 2, 1991, and assigned ATCC Accession Nos. 68721 and 68722, respectively. Additional polynucleotide sequences illustrating the invention are the inserts in the plasmid pING3746 in E. coli E104 (designated strain G277) and in the plasmid pING3737 in E. coli E104 (designated strain G276), which were both deposited with the ATCC on June 9, 1992, and were respectively assigned Accession Nos. 69008 and 69009. Still other polynucleotide sequences illustrating the invention are the inserts in the plasmid pING3747 in E. coli E104 (designated strain G278), in the plasmid pING3754 in E. coli E104 (designated strain G279), in the plasmid pING3758 in E. coli E104 (designated strain G280) and in the plasmid pING3759 in E. coli E104 (designated strain G281), which plasmids were all deposited with the ATCC on Oct. 27, 1992 and were assigned ATCC Accession Nos. 69101, 69102, 69103 and 69104, respectively.

BRIEF DESCRIPTION OF THE DRAWINGS

FIG. 1 is a computer-generated alignment of the amino acid sequence of the ricin A-chain (RTA) (SEQ ID NO: 1) with the amino acid sequence of the Type I ribosome-inactivating protein gelonin (SEQ ID NO: 2), wherein starred positions indicate amino acids invariant among the ricin A-chain and the Type I RIPs;

FIG. 2 is a computer-generated alignment of the amino acid sequence of the ricin A-chain (SEQ ID NO: 1) with the amino acid sequence of the Type I ribosome-inactivating protein BRIP (SEQ ID NO: 3), wherein starred positions indicate amino acids invariant among the ricin A-chain and the Type I RIPs;

FIG. 3 is a computer-generated alignment of the amino acid sequence of the ricin A-chain (SEQ ID NO: 1) with the amino acid sequence of the Type I ribosome-inactivating protein momordin II (MOMOII) (SEQ ID NO: 4), wherein starred positions indicate amino acids invariant among the ricin A-chain and the Type I RIPs;

FIG. 4 is a computer-generated alignment of the amino acid sequence of the ricin A-chain (SEQ ID NO: 1) with the amino acid sequence of the Type I ribosome-inactivating protein luffin (SEQ ID NO: 5), wherein starred positions indicate amino acids invariant among the ricin A-chain and the Type I RIPs;

FIG. 5 is a computer-generated alignment of the amino acid sequence of the ricin A-chain (SEQ ID NO: 1) with the amino acid sequence of the Type I ribosome-inactivating protein αtrichosanthin (TRICHO) (SEQ ID NO: 6), wherein starred positions indicate amino acids invariant among the ricin A-chain and the Type I RIPs;

FIG. 6 is a computer-generated alignment of the amino acid sequence of the ricin A-chain (SEQ ID NO: 1) with the amino acid sequence of the Type I ribosome-inactivating protein momordin I (MOMOI) (SEQ ID NO: 7), wherein starred positions indicate amino acids invariant among the ricin A-chain and the Type I RIPs;

FIG. 7 is a computer-generated alignment of the amino acid sequence of the ricin A-chain (SEQ ID NO: 1) with the amino acid sequence of the Type I ribosome-inactivating protein Mirabilis anti-viral protein (MAP) (SEQ ID NO: 8), wherein starred positions indicate amino acids invariant among the ricin A-chain and the Type I RIPs;

FIG. 8 is a computer-generated alignment of the amino acid sequence of the ricin A-chain (SEQ ID NO: 1) with the amino acid sequence of the Type I ribosome-inactivating protein pokeweed antiviral protein from seeds (PAPS) (SEQ ID NO: 9), wherein starred positions indicate amino acids invariant among the ricin A-chain and the Type I RIPs;

FIG. 9 is a computer-generated alignment of the amino acid sequence of the ricin A-chain (SEQ ID NO: 1) with the amino acid sequence of the Type I ribosome-inactivating protein saporin 6 (SAP6) (SEQ ID NO: 10), wherein starred positions indicate amino acids invariant among the ricin A-chain and the Type I RIPs.

DETAILED DESCRIPTION

Nucleotide sequences of genes encoding three plant Type I RIPs and expression vectors containing the genes are provided by the present invention. A first plant RIP, gelonin, is produced by seeds of *Gelonium multiflorum*, a plant of the Euphorbiaceae family native to the tropical forests of eastern Asia, while a second plant RIP, BRIP, is synthesized by the common cereal grain barley. Momordin II, a third plant RIP, is produced in *Momordica balsamina* seeds. Analogs of BRIP are also provided by the present invention. The analogs were genetically engineered to include a cysteine free to participate in a intermolecular disulfide bond and were conjugated to antibody molecules without non-specific chemical derivatization of the RIP with crosslinking agents.

Type I RIP analogs of the present invention offer distinct advantages over the natural proteins for use as components of immunotoxins. Chemical treatment to introduce free sulfhydryl groups in the natural proteins lacking free cysteines typically involves the non-selective modification of amino acid side chains. This non-selectivity often results in antibodies conjugated to different sites on different RIP molecules (i.e., a heterogeneous population of conjugates) and also in a decrease in RIP activity if antibodies are conjugated in or near important regions of the RIP (e.g., the active site or regions involved in translocation across cell membranes). In contrast, RIP analogs according to the present invention can be conjugated to a single antibody through a disulfide bond to a specific residue of the analog resulting in reduced batch to batch variation of the immunoconjugates and, in some cases, immunoconjugates with enhanced properties (e.g., greater cytotoxicity or solubility).

Type I plant RIPs, as well as bacterial RIPs such as shiga and shiga-like toxin A-chains, are homologous to the ricin A-chain and are useful in the present invention.

Type I RIPs may be defined and sites for substitution of a cysteine in a RIP may be identified by comparing the primary amino acid sequence of the RIP to the natural ricin A-chain amino acid sequence, the tertiary structure of which has been described in Katzin et al., *Proteins*, 10, 251–259 (1991), which is incorporated by reference herein.

Amino acid sequence alignment defines Type I RIPs in that the ricin A-chain and the Type I plant RIPs have nine invariant amino acids in common. Based on the ricin sequence the invariant amino acids are tyrosine$_{21}$, arginine$_{29}$, tyrosine$_{80}$, tyrosine$_{123}$, leucine$_{144}$, glutamic acid$_{177}$, alanine$_{178}$, arginine$_{180}$, and tryptophan$_{211}$. The ricin A-chain may be used as a model for the three-dimensional structure of Type I RIPs. A protein lacking a cysteine available for conjugation while having ribosome-inactivating activity and having the nine invariant amino acids when its primary sequence is compared to the primary sequence of the ricin A-chain [according to the alignment algorithm of Myers et al., *CABIOS COMMUNICATIONS*, 4(1), 11–17 (1988), implemented by the PC/GENE program PALIGN (Intelligenetics, Inc., Mountain View, Calif.) and utilizing the Dayhoff Mutation Data Matrix (MDM-78) as described in Schwartz et al., pp. 353–358 in *Atlas of Protein Sequence and Structure*, 5 Supp. 3, National Biomedical Research Foundation, Washington, D.C. (1978)] is defined as a Type I RIP herein and is expected to be useful in the present invention. "Corresponding" refers herein to amino acid positions that align when two amino acid sequences are compared by the strategy of Myers et al., supra.

The primary amino acid sequences of the Type I RIPs gelonin, BRIP, momordin II, luffin [see Islam et al., *Agricultural Biological Chem.*, 54(5), 1343–1345 (199)], αtrichosanthin [see Chow et al., *J. Biol. Chem.*, 265, 8670–8674 (1990)], momordin I [see Ho et al., *BBA*, 1088, 311–314 (1991)], Mirabilis anti-viral protein [see Habuka et al., *J. Biol. Chem.*, 264(12), 6629–6637 (1989)], pokeweed antiviral protein isolated from seeds [see Kung et al., *Agric. Biol. Chem.*, 54(12), 3301–3318 (1990)] and saporin [see Benatti et al., *Eur. J. Biochem.*, 183, 465–470 (1989)] are individually aligned with the primary sequence of the ricin A-chain [see Halling et al., *Nucleic Acids Res.*, 13, 8019–8033 (1985)] in FIGS. 1–9, respectively, according to the algorithm of Myers et al., supra, as specified above.

FIGS. 1–9 may be utilized to predict the amino acid positions of the Type I RIPs where cysteine residues may be substituted. Preferred amino acids for cysteine substitution are on the surface of the molecule and include any solvent accessible amino acids that will not interfere with proper folding of the protein if replaced with a cysteine. A region of the ricin A-chain comprising such amino acids is the carboxyl terminal region. Amino acids that should be avoided for replacement are those critical for proper protein folding, such as proline, and those that are solvent inaccessible. Also to be avoided are the nine amino acids invariant among RIPs, and the amino acids in or near regions comprising the active site of ricin A-chain as depicted in FIG. 6 of Katzin et al., supra.

Therefore, a preferred region of substitution for Type I RIPs is their carboxyl terminal region which is solvent accessible and corresponds to the carboxyl terminal region where Type II RIP A-chains and B-chains are naturally linked by a disulfide bond. As shown in the examples, a cysteine may be substituted in positions in the amino acid sequence of a Type I RIP from the position corresponding to position 251 in SEQ ID NO: 1 to the carboxyl terminal position of said Type I RIP, resulting in RIP analogs which retain enzymatic activity and gain disulfide crosslinking capability. One preferred cysteine substitution position is near the position which corresponds to the cysteine at position 259 in the ricin A-chain.

Immunotoxins specifically illustrating the present invention including cytotoxic agents and gene fusion products are particularly suited for use in treatment of human autoimmune disease where T-cell function is implicated. Treatment of autoimmune diseases with immunotoxins is described in co-owned U.S. patent application Ser. No. 07/306,433 filed on Sep. 13, 1991 and in International Publication No. WO89/06968 published Aug. 10, 1989, which are incorporated by reference herein. Examples of autoimmune diseases are systemic lupus erythematosus, scleroderma diseases (including lichen sclerosus, morphea and lichen planus), rheumatoid arthritis, chronic thyroiditis, pemphigus vulgaris, diabetes mellitus type 1, progressive systemic sclerosis, aplastic anemia, myasthenia gravis, myositis, Sjogrens disease, Crohn's disease, ulcerative colitis, and primary biliary cirrhosis. Autoimmunity is also implicated in multiple sclerosis, uveitis, psoriasis and Meniere's disease. A general description of various autoimmune diseases may be found in Rose and Mackey, Eds., *The Autoimmune Diseases*, Academic Press (1985).

The immunotoxins may be administered to a patient either singly or in a cocktail containing two or more immunotoxins, other therapeutic agents, compositions, or the like, including, but not limited to, immunosuppressive agents, tolerance-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally-accepted efficacious dose ranges such as those disclosed in the *Physician's Desk Reference*, 41st Ed., Publisher Edward R. Barnhart, N.J. (1987). Patent Cooperation Treaty (PCT) patent application WO 89/069767 published on Aug. 10, 1989, discloses administration of an immunotoxin as an immunosuppressive agent and is incorporated by reference herein.

Anti-T cell immunotoxins may be formulated into either an injectable or topical preparation. Parenteral formulations are known and are suitable for use in the invention, preferably for intramuscular or intravenous administration. The formulations containing therapeutically-effective amounts of anti-T cell immunotoxins are either sterile liquid solutions, liquid suspensions or lyophilized versions, and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where the biological activity is less than or equal to 20 ng/ml when measured in a reticulocyte lysate assay. Typically, the pharmaceutical compositions containing anti-T cell immunotoxins will be administered in a therapeutically effective dose in a range of from about 0.01 mg/kg to about 5 mg/kg of the patient. A preferred, therapeutically effective dose of the pharmaceutical composition containing anti-T cell immunotoxin will be in a range of from about 0.01 mg/kg to about 0.5 mg/kg body weight of the patient administered over several days to two weeks by daily intravenous infusion, each given over a one hour period, in a sequential patient dose-escalation regimen.

Anti-T cell immunotoxin is formulated into topical preparations for local therapy by including a therapeutically effective concentration of anti-T cell immunotoxin in a dermatological vehicle. The amount of anti-T cell immunotoxin to be administered, and the anti-T cell immunotoxin concentration in the topical formulations, depends upon the vehicle selected, the clinical condition of the patient, the systemic toxicity and the stability of the anti-T cell immunotoxin in the formulation. Thus, a physician knows to employ the appropriate preparation containing the appropriate concentration of anti-T cell immunotoxin in the formulation, as well as the appropriate amount of formulation to administer depending upon clinical experience with the patient in question or with similar patents. The concentration of anti-T cell immunotoxin for topical formulations is in the range of greater than from about 0.1 mg/ml to about 25 mg/ml. Typically, the concentration of anti-T cell immunotoxin for topical formulations is in the range of greater than from about 1 mg/ml to about 20 mg/ml. Solid dispersions of anti-T cell immunotoxin as well as solubilized preparations can be used. Thus, the precise concentration to be used in the vehicle is subject to modest experimental manipulation in order to optimize the therapeutic response. Greater than about 10 mg anti-T cell immunotoxin/100 grams of vehicle may be useful with 1% w/w hydrogel vehicles in the treatment of skin inflammation. Suitable vehicles, in addition to gels, are oil-in-water or water-in-oil emulsions using mineral oils, petroleum and the like.

Anti-T cell immunotoxin is optionally administered topically by the use of a transdermal therapeutic system [Barry, *Dermatological Formulations*, p. 181 (1983) and literature cited therein]. While such topical delivery systems have been designed for transdermal administration of low molecular weight drugs, they are capable of percutaneous delivery. They may be readily adapted to administration of anti-T cell immunotoxin or derivatives thereof and associated therapeutic proteins by appropriate selection of the rate-controlling microporous membrane.

Topical preparations of anti-T cell immunotoxin either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically-acceptable buffer may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the anti-T cell immunotoxin or other agents. Such agents should desirably possess some or all of the following features as would be known to the ordinarily skilled artisan: pharmacological inertness, non-promotive of body fluid or electrolyte loss, compatible with anti-T cell immunotoxin (non-inactivating), and capable of formulation into creams, gels or other topical delivery systems as desired.

Anti-T cell immunotoxin may also be administered by aerosol to achieve localized delivery to the lungs. This is accomplished by preparing an aqueous aerosol, liposomal preparation or solid particles containing immunotoxin. Ordinarily, an aqueous aerosol is made by formulating an aqueous solution or suspension of anti-T cell immunotoxin together with conventional pharmaceutically acceptable carriers and stabilizers. The carriers and stabilizers vary depending upon the requirements for the particular anti-T cell immunotoxin, but typically include: nonionic surfactants (Tweens, Pluronics, or polyethylene glycol); innocuous proteins like serum albumin, sorbitan esters, oleic acid, lecithin; amino acids such as glycine; and buffers, salts, sugars or sugar alcohols. The formulations may also include mucolytic agents as well as bronchodilating agents. The formulations are sterile. Aerosols generally are prepared from isotonic solutions. The particles optionally include normal lung surfactants.

Aerosols may be formed of the particles in aqueous or nonaqueous (e.g., fluorocarbon propellant) suspension. Such particles include, for example, intramolecular aggregates of anti-T cell immunotoxin or derivatives thereof or liposomal or microcapsular-entrapped anti-T cell immunotoxin or derivatives thereof. The aerosols should be free of lung irritants, i.e., substances which cause acute bronchoconstriction, coughing, pulmonary edema or tissue destruction. However, nonirritating absorption-enhancing agents are suitable for use herein. Sonic nebulizers are preferably used in preparing aerosols. Sonic nebulizers minimize exposing the anti-T cell immunotoxin or derivatives thereof to shear, which can result in degradation of anti-T cell immunotoxin.

Anti-T cell immunotoxin may be administered systemically, rather than topically, by injection intramuscularly, subcutaneously, intrathecally or intraperitoneally or into vascular spaces, particularly into the joints, e.g., intraarticular injection at a dosage of greater than about 1 μg/cc joint fluid/day. The dose will be dependent upon the properties of the anti-T cell immunotoxin employed, e.g., its activity and biological half-life, the concentration of anti-T cell immunotoxin in the formulation, the site and rate of dosage, the clinical tolerance of the patient involved, the autoimmune disease afflicting the patient and the like, as is well within the skill of the physician.

The anti-T cell immunotoxins of the present invention may be administered in solution. The pH of the solution should be in the range of pH 5 to 9.5, preferably pH 6.5 to 7.5. The anti-T cell immunotoxin or derivatives thereof should be in a solution having a suitable pharmaceutically-acceptable buffer such as phosphate, Tris(hydroxymethyl)aminomethane-HCl or citrate and the like. Buffer concentrations should be in the range of 1 to 100 mM. The solution of anti-T cell immunotoxin may also contain a salt, such as sodium chloride or potassium chloride in a concentration of 50 to 150 mM. An effective amount of a stabilizing agent such as an albumin, a globulin, a gelatin, a protamine or a salt of protamine may also be included, and may be added to a solution containing anti-T cell immunotoxin or to the composition from which the solution is prepared.

Systemic administration of anti-T cell immunotoxin is made daily and is generally by intramuscular injection, although intravascular infusion is acceptable. Administration may also be intranasal or by other nonparenteral routes. Anti-T cell immunotoxin may also be administered via microspheres, liposomes or other microparticulate delivery systems placed in certain tissues including blood. Topical preparations are applied daily directly to the skin or mucosa and are then preferably occluded, i.e., protected by overlaying a bandage, polyolefin film or other barrier impermeable to the topical preparation.

The following examples illustrate practice of the invention but are not to be construed as limiting the invention. Example 1 is a description of the cloning of a cDNA encoding the Type I RIP gelonin. Example 2 describes the construction of recombinant expression vectors containing the gelonin gene. Described in Example 3 are constructions of various analogs of gelonin having a single cysteine available for disulfide bonding. Example 4 describes the testing of recombinant gelonin and the gelonin analogs for the capacity to inhibit protein synthesis in a reticulocyte lysate assay. Example 5 presents descriptions of the preparation of various gelonin immunoconjugates. Example 6 describes of the testing of the immunoconjugates for the capacity to act as cytotoxic agents in a whole cell kill assay. Example 7 presents solubility and stability characteristics of the immunoconjugates. Examples 8 presents results of in vivo pharmacokinetic and immunogenicity studies of the gelonin immunoconjugates and Example 9 presents results of testing of the immunoconjugates for the capacity to deplete human T cells in a human peripheral blood lymphocyte-reconstituted, severe combined immunodeficient mouse model. Described in Example 10 are various gene fusions of gelonin DNA sequences and sequences encoding antibody fragments. Expression of products of the gene fusions products and testing of the products in the reticulocyte and whole cell kill assays are described in Example 11. Example 12 is a description of the construction of gelonin gene fusions to single chain antibodies. Example 13 describes the cloning of a cDNA encoding the Type I RIP BRIP, construction of expression vectors containing the BRIP gene, production of BRIP analogs having a single cysteine available for disulfide bonding, testing of the analogs in the reticulocyte lysate assay, and construction of the BRIP immunoconjugates and testing of their activity in the whole cell kill assay. Example 14 describes the cloning of a cDNA encoding momordin II and construction of expression vectors containing the momordin II gene.

Example 1

The cloning of the gelonin gene according to the present invention obviates the requirement of purifying the RIP gene product from its relatively scarce natural source, *G. multiflorum* seeds, and allows development of gelonin analogs conjugatable to antibodies without prior chemical derivatization and development of gelonin gene fusion products. One formidable hurdle in the cloning of the gene was that the available Gelonium seeds are old and inviable, making preparation of intact messenger RNA from the seeds impossible. Cloning the gene from cDNA prepared from messenger RNA was thus impractical and total RNA was utilized to generate cDNA. Using total RNA to make cDNA under normal circumstances, i.e., when mRNA may be utilized, is not desirable because total RNA typically comprises about 95% ribosomal RNA.

Preparation of RNA from G. multiflorum Seeds

Total. RNA was prepared from Gelonium seeds (Dr. Michael Rosenblum, M.D. Anderson Cancer Center, Houston, Tex.) by a modification of the procedure for preparation of plant RNA described in Ausubel et al., eds., *Current Protocols in Molecular Biology:*, Wiley & Sons, 1989. Briefly, 4.0 grams of seeds were ground to a fine powder in a pre-cooled (−70° C.) mortar and pestle with liquid $N_2$. The powder was added to 25 ml Grinding buffer (0.18M Tris, 0.09M LiCl, 4.5mM EDTA, 1% SDS, pH 8.2) along with 8.5 ml of phenol equilibrated with TLE (0.2M Tris, 0.1M LiCl, 5mM EDTA pH8.2). The mixture was homogenized using a Polytron PT-1035 (#5 setting). 8.5 ml of chloroform was added, mixed and incubated at 50° C. for 20 minutes. The mixture was centrifuged at 3K for 20 minutes in a rotor precooled to 4° C. and the aqueous phase was transferred to a new tube. 8.5 ml of phenol was added followed by 8.5 ml of chloroform and the mixture was recentrifuged. This extraction was repeated 3 times. The RNA in the aqueous phase was then precipitated by adding 1/3 volume 8M LiCl, and incubated at 4 ° C. for 16 hours. Next, the RNA was pelleted by centrifugation for 20 minutes at 4 ° C. The pellet was washed with 5 ml of 2M LiCl, recentrifuged and resuspended in 2 ml of water. The RNA was precipitated by addition of NaOAc to 0.3M and 2 volumes of ethanol. The RNA was stored in 70% ethanol at −70° C.

cDNA Preparation cDNA was prepared from total Gelonium RNA by two similar methods. The first method involved making a cDNA library in the bacterial expression plasmid pcDNAII using the Librarian II cDNA Library Construction System kit (Invitrogen). About 5 μg of total RNA was converted to first strand cDNA with a 1:1 mixture of random primers and oligo-dT. Second strand synthesis with DNA polymerase I was performed as described by the system manufacturer. Double stranded cDNA was ligated to BstX1 linkers and size fractionated. Pieces larger than about 500 bp were ligated into the expression vector provided in the kit. Individual vectors were introduced into *E. coli* either by transformation into high-efficiency competent cells or by electroporation into electrocompetent cells. Electroporation was performed with a BTX100 unit (BTX, San Diego, CA) in 0.56 μ Flatpack cells as recommended by BTX based on the method of Dower et al., *Nucleic Acids Res.*, 16, 6127–6145 (1988), at a voltage amplitude of 850 V and a pulse length of 5 mS. The resulting library consisted of approximately 150,000 colonies.

The second method involved generating cDNA using the RNA-PCR kit sold by Perkin-Elmer-Cetus. About 100 ng of total Gelonium RNA was used as template for cDNA synthesis.

Determination of the Gelonin Protein Sequence

The partial sequence of the native gelonin protein was determined by direct amino acid sequence analysis by automated Edman degradation as recommended by the manufacturer using an Applied Biosystems model 470A protein sequencer. Proteolytic peptide fragments of gelonin (isolated from the same batch of seeds as the total RNA) were sequenced.

Cloning of the Gelonin Gene

Three overlapping gelonin cDNA fragments were cloned and a composite gelonin gene was assembled from the three fragments.

(1) Cloning of the Fragment Encoding the Middle Amino Acids of Gelonin in Vector pING3823.

Degenerate DNA primers based on the gelonin partial amino acid sequences were used to amplify by PCR, segments of the cDNA generated with the Perkin-Elmer-Cetus kit. Six primers were designed based on regions of the gelonin amino acid sequence where degeneracy of the primers could be minimized. Appropriate pairs of primers were tested for amplification of a gelonin gene fragment. When products of the expected DNA size were identified as ethidium bromide-stained DNA bands on agarose gels, the DNA was treated with T4 DNA polymerase and then purified from an agarose gel. Only the primer pair consisting of primers designated gelo-7 and gelo-5 yielded a relatively pure product of the expected size. The sequences of degenerate primers gelo-7 and gelo-5 are set out below using IUPAC nucleotide symbols.

Gelo-7 (SEQ ID NO: 14)
5' TTYAARGAYGCNCCNGAYGCNGCNTAYGARGG 3'
Gelo-5 (SEQ ID NO: 15)
3' TTYTTYATRATRCANTGNCGNCANCTRGTYCA 5'

Primer gelo-7 corresponds to amino acids 87–97 of gelonin while primer gelo-5 corresponds to amino acids 226–236. The blunt-ended DNA fragment (corresponding to amino acids 87 to 236 of gelonin) generated with primers gelo-7 and gelo-5 was cloned into pUC 18 (BRL, Gaithersburg, Maryland). The DNA sequence of the insert was determined, and the deduced amino acid sequence based on the resulting DNA sequence matched the experimentally determined gelonin amino acid sequence. The clone containing this gelonin segment is denoted pING3726.

The insert of clone pING3726 was labeled with $^{32}P$ and used as a probe to screen the 150,000-member Gelonium cDNA library. Only one clone hybridized to the library plated in duplicate. This clone was purified from the library and its DNA sequence was determined. The clone contains a fragment encoding 185 of the 270 amino acids of gelonin (residues 25–209) and is denoted pING3823.

(2) Cloning of the Fragment Encoding the N-terminal Amino Acids of Gelonin.

Based on the sequence determined for the gelonin gene segment in pING3726, exact oligonucleotide primers were designed as PCR amplification primers to be used in conjunction with a degenerate primer to amplify a 5' gelonin gene fragment and with a nonspecific primer to amplify a 3' gelonin gene fragment. cDNA generated using the Perkin-Elmer-Cetus RNA-PCR kit was amplified.

To amplify the 5'-end of the gelonin gene, PCR amplification with a degenerate primer gelo-1 and an exact primer gelo-10 was performed. The sequences of the primers are set out below.

Gelo-1 (SEQ ID NO: 16)
5' GGNYTNGAYACNGTNWSNTTYWSNACNAARGG 3'
Gelo-10 (SEQ ID NO: 17)

3' TGTCTGAACCCGTAACTTGGTAA 5'

Primer gelo-1 corresponds to amino acids 1-11 of the gelonin gene while primer gelo-10 corresponds to amino acids 126-133. The product from the reaction was reamplified with gelo-1 (SEQ ID NO: 16) and gelo-11 (an exact primer comprising sequences encoding amino acids 119-125 of gelonin) to confer specificity to the reaction product. The sequence of primer gelo-11 is listed below.

Gelo-11 (SEQ ID NO: 18)
3' CACTCTTCCGTATATCTCTCTGT 5'

Hybridization with an internal probe confirmed that the desired specific gelonin DNA fragment was amplified. This fragment was cloned into pUC18, and the vector generated was designated pING3727. The fragment was sequenced revealing that the region of the fragment (the first 27 nucleotides) corresponding to part of the degenerate primer gelo-1 could not be translated to yield the amino acid sequence upon which primer gelo-1 was originally based. This was not unexpected considering the degeneracy of the primer. The fragment was reamplified from the Gelonium cDNA with exact primers gelo-11 (SEQ ID NO: 18) and gelo-5' (which extends upstream of the 5' end of the gelonin gene in addition to encoding the first 16 amino acids of gelonin). The sequence of primer gelo-5' is set out below.

Gelo-5'(SEQ ID NO: 19)
5' TCAACCCGGGCTAGATACCGTGTCAT
TCTCAACCAAAGGTGCCACTTATATTA 3'

The resulting DNA fragment encodes the first 125 amino acids of gelonin. While the majority of the sequence is identical to the natural gelonin gene, the first 32 nucleotides of the DNA fragment may not be. For the purposes of this application this N-terminal fragment is referred to as fragment GEL1-125.

(3) Cloning of the Fragment Encoding the C-terminal Amino Acids of Gelonin.

To amplify the 3'-end of the gelonin gene as well as 3'untranslated sequences, PCR amplification with exact primers gelo-9 and XE-dT was performed. The sequence of each of the primers is set out below.

Gelo-9 (SEQ ID NO: 20)
5' CTTCATTTTGGCGGCACGTATCC 3'
XE-DT (SEQ ID NO: 21)
3' TTTTTTTTTTTTTTTTTTTTTTAG
GGTGCATTCGAACGTCGGAGCTC 5'

Primer gelo-9 corresponds to amino acids 107-113 of gelonin. Primer XE-dT consists of an 3' oligo-dT portion and a 5' portion containing the restriction sites HindIII and XhoI, and will prime any poly A-containing cDNA. The reaction product was reamplified with exact primers gelo-8 and XE. The sequences of primers gelo-8 and XE are set out below.

Gelo-8 (SEQ ID NO: 22)
5' CTCGCTGGAAGGTGAGAA 3'
XE (SEQ ID NO: 23)

3' AGGGTGCATTCGAACGTCGGAGCTC 5'

Primer gelo-8 consists of sequences encoding amino acids 115-120 of gelonin while the primer XE corresponds to the 5' portion of the XE-dT primer which contains HindIII and XhoI restriction sites. Hybridization with internal probes confirmed that the desired gelonin gene fragment was amplified. The fragment was cloned into pUC 18 by two different methods. First, it was cloned as a blunt-ended fragment into the SmaI site of pUC 18 (the resulting vector was designated pING3728) and, second, it was cloned as an EcoRI to HindIII fragment into pUC18 (this vector was designated pING3729). Both vector inserts were sequenced. The insert of pING3728 encodes amino acids 114-270 of gelonin, while the insert of pING3729 encodes amino acids 184-270 of gelonin plus other 3' sequences.

(4) Assembly of the overlapping gelonin DNA fragments into a composite gelonin gene To reassemble the C-terminal two-thirds of the gelonin gene, vector pING3729 was cut with SspI (one SspI site is located within the vector and the second is located about 80 bp downstream of the termination codon of the insert in the vector) and an XhoI linker (8 bp, New England Biolabs) was ligated to the resulting free ends. The DNA was then cut with XhoI and EcoRI, and the 350 bp fragment generated, encoding amino acids 185-270 of gelonin, was isolated. This 350 bp fragment was ligated adjacent to a NcoI to EcoRI fragment from pING3823 encoding amino acids 37-185 of gelonin in a intermediate vector denoted pING3730, thus reassembling the terminal 87% of the gelonin gene (amino acids 37-270).

Next, fragment GEL1-125 was cut with SmaI and NcoI, resulting in a fragment encoding amino acids 1-36 of gelonin which was ligated along with the NcoI to XhoI fragment of pING3730 into the vector pIC100. [pIC100 is identical to pING1500 described in Better et al., Science, 240, 1041-1043 (1988), except that it lacks 37 bp upstream of the pelB leader sequence. The 37 bp were eliminated by digestion of pING1500 with SphI and EcoRI, treatment with T4 polymerase and religation of the vector. This manipulation regenerated an EcoRI site in the vector while eliminating other undesirable restriction sites.] Before ligation, the vector pIC100 had previously been digested with SstI, treated with T4 polymerase, and cut with XhoI. The ligation generated a new vector containing a complete gelonin gene that was designated plasmid pING3731 (ATCC Accession No. 68721). The complete DNA sequence of the gelonin gene is set out in SEQ ID NO: 11.

Example 2

Construction of Expression Vectors Containing the Gelonin Gene

A first *E. coli* expression vector was constructed containing the gelonin gene linked to the *Erwinia carotovora* pelB leader sequence, and to the *Salmonella typhimurium* araB promoter. A basic vector containing the araB promoter is described in co-owned U.S. Pat. No. 5,028,530 issued Jul. 2, 1991 which is incorporated by reference herein. The vector containing the arab promoter was cut with EcoRI and XhoI. Two DNA fragments were then ligated in tandem immediately downstream of the promoter. The fragment ligated adjacent to the promoter was a 131 bp fragment derived from SstI digestion, T4 polymerase treatment and digestion with EcoRI of the pIC100 vector which includes the leader sequence of the *E. carotovora* pelB gene. The translated leader sequence is a signal for secretion of the respective protein through the cytoplasmic membrane. The fragment ligated downstream of the leader sequence was a SmaI to XhoI fragment from pING3731 which contains the complete gelonin gene. Thus, the expression vector contains the gelonin gene linked to the pelB leader sequence and the araB promoter. This plasmid is designated pING3733.

A second expression vector may be constructed that is identical to the first except that the gelonin gene sequences encoding the nineteen C-terminal amino acids of gelonin are not included. The cDNA sequence of the gelonin gene predicted a 19 residue C-terminal segment that was not detected in any peptide fragments generated for determination of the gelonin amino acid sequence. These 19 amino acids may represent a peptide segment that is cleaved from the mature toxin post-translationally, i.e. that is not present in the native protein. A similar C-terminal amino acid segment was identified in the plant toxin αtrichosanthin [Chow et al., *J Biol. Chem.*, 265, 8670–8674 (1990)]. Therefore, the expression product without the C-terminal fragment may be of importance.

For construction of a gelonin expression vector without the 19 C-terminal amino acids of gelonin, PCR was used to amplify and alter the 3'l -end of the gene. pING3728 was amplified with primers gelo-14 and gelo-9 (SEQ ID NO: 20). The sequence of primer gelo-14 is set out below.

Gelo-14 (SEQ ID NO: 24)
5' TGATCTCGAGTACTATTTAGGATCTTTATCGACGA 3'

Primer gelo-14, which corresponds to gelonin amino acids 245–256, introduces a termination codon (underlined in the primer sequence) in the gelonin gene sequence which stops transcription of the gene before the sequences encoding the terminal 19 amino acids of the gelonin and also introduces a XhoI site immediately downstream of the termination codon. The PCR product was cut with XhoI and EcoRI, and the resulting 208 bp fragment encoding amino acids 185–251 of gelonin was purified from an agarose gel. This fragment was ligated adjacent to the NcoI to EcoRI fragment from pING3823 encoding amino acids 37–185 of gelonin to generate plasmid pING3732. A final expression vector, pING3734, containing a gelonin gene with an altered 3'-end was generated by substituting an NcoI to XhoI fragment encoding amino acids 37–251 of gelonin from pING3732 into pING3733.

Identification of the Native Gelonin 5'-End

Inverse PCR was used to identify a cDNA clone encoding the 5'-end of the mature gelonin gene. 5 μg of total *G. multiflorum* RNA was converted to cDNA using the Superscript Plasmid System (BRL, Gaithersburg, Maryland) with Gelo-11 (SEQ ID NO: 18) as a primer. Gelonin cDNA was self-ligated to generate covalent circular DNA and the ligated DNA was amplified by PCR with oligonucleotides Gelo-9 (SEQ ID NO: 20) and Gelo-16. The sequence of primer Gel-16 is set out below.

Gelo-16 (SEQ ID NO: 25)
5' GTAAGCAGCATCTGGAGCATCT 3'

The PCR product was size-fractionated on an agarose gel and DNAs larger than 300 bp were cloned into SmaI cut pUC18. Several clones were sequenced with the primer Gelo-18, the sequence of which is set out below.

Gelo-18 (SEQ ID NO: 26)
5' CATTCAAGAAATTCACGTAGG 3'

A clone identified as having the largest gelonin-specific insert was designated pING3826. The DNA sequence of pING3826 included the first 32 nucleotides of the natural, mature gelonin gene not necessarily present in gelonin expression plasmids pING3733 and pING3734. The complete DNA sequence of the natural gelonin gene is set out in SEQ ID NO: 57.

Construction of Expression Vectors Containing a Gelonin Gene with a Natural 5'End Derivatives of expression vectors pING3733 and pING3734 (described above) containing a gelonin gene with the natural 5' sequence were generated as follows. The 5'-end of gelonin was amplified from pING3826 with the PCR primers Gelo-16 (SEQ ID NO: 24) and Gelo-17, the sequence of which is set out below.

Gelo-17 (SEQ ID NO: 27)
5'GGCCTGGACACCGTGAGCTTTAG 3'

The 285 bp PCR product was treated with T4 polymerase and cut with NcoI. The resulting 100 bp 5'-end DNA fragment was isolated from an agarose gel and ligated adjacent to the 120 bp pelB leader fragment from plC100 (cut with SstI, treated with T4 polymerase and cut with PstI) into either pING3733 or pING3734 digested with PstI and NcoI. The resulting plasmids pING3824 and pING3825 contain the entire native gelonin gene and the native gelonin gene minus the nineteen amino acid carboxyl extension, respectively, linked to the pelB leader and under the transcriptional control of the araB promoter. The gene construct without the nineteen amino acid carboxyl extension in both pING3734 and pING3825 encodes a protein product referred to in this application as "recombinant gelonin."

Purification of Recombinant Gelonin

Recombinant gelonin was purified by the following procedure: *E. coli* fermentation broth was concentrated and buffer-exchanged to 10 mM sodium phosphate at pH 7.0 by using an S10Y10 cartridge over a DC10 unit (Areicon) the concentrated and buffer-exchanged material was applied to a CM52 column (100 g, 5×10 cm). The column was washed with 1 L of starting buffer and eluted with a 0 to 300 mM NaCl gradient in starting buffer (750 ml total volume). The pure gelonin containing fractions were pooled (elution was from 100–250 mM NaCl), concentrated over an Amicon YM10 membrane, equilibrated with 10 mM sodium phosphate buffer, pH 7.0, and stored frozen at −20°C. A further purification step was attempted using Blue Toyopearl chromatography. However, this procedure did not result in an increased purity of material, and resulted in an approximate 50% loss of the starting material.

Example 3

Assembly of gelonin genes with cysteine residues available for conjugation

The gelonin protein has two cysteine residues at positions 44 and 50 which are linked by an endogenous disulfide bond. The protein contains no free cysteine residue directly available for conjugation to antibodies or other proteins. Analogs of gelonin which contain a free cysteine residue available for conjugation were generated by three different approaches. In one approach, various residues along the primary sequence of the gelonin were replaced with a cysteine residue, creating a series of analogs which contain an odd number of cysteine residues. In another approach, one of the two endogenous cysteines was replaced by alanine, creating a molecule which lacks an intrachain disulfide bond but contains a single, unpaired cysteine. In yet another approach both endogenous cysteines were replaced by alanines and a third non-cysteine residue was replaced by a cysteine, creating an analog with a single, unpaired cysteine.

Fifteen analogs of gelonin were constructed. Ten non-cysteine residues of gelonin were targeted for substitution with a cysteine residue. Comparison of the amino acid sequence of gelonin to the natural amino acid sequence and tertiary structure of the ricin A-chain (see FIG. 1) suggested that these positions would be at the surface of the molecule and available for conjugation. Each of the ten gelonin analogs include a cysteine substituted in place of one of the following residues: lysine$_{10}$, asparagine$_{60}$, isoleucine$_{103}$, aspartic acid$_{146}$, arginine$_{184}$, serine$_{215}$, asparagine$_{239}$, lysine$_{244}$, aspartic acid$_{247}$, and lysine$_{248}$, and the analogs have respectively been designated Gel$_{c10}$, Gel$_{c60}$, Gel$_{c103}$, Gel$_{c146}$, Gel$_{c184}$, Gel$_{c215}$, Gel$_{c239}$, Gel$_{c244}$, Gel$_{c247}$, and Gel$_{c248}$.

Two analogs of gelonin were constructed in which one of the native gelonin cysteines that participates in an endogenous disulfide bond was replaced with a non-cysteine residue. Specifically, the cysteine at position 50 was replaced with an alanine residue, creating a gelonin analog (designated Gel$_{c44}$) which has a cysteine available for disulfide bonding at position 44. Conversely, the cysteine at position 44 was replaced with an alanine residue, resulting in an analog (designated Gel$_{c50}$) which has a cysteine available for disulfide bonding at position 50. The combined series of the foregoing twelve analogs thus spans the entire length of the mature gelonin protein.

Another gelonin analog (Gel$_{c44AC50A}$) was constructed in which both native gelonin cysteines were replaced with alanines. Two additional analogs were constructed that have alanine residues substituted in place of both native cysteines and have either a cysteine residue substituted in place of the native lysine at position 10 (GelC10$_{c44AC50A}$) or a cysteine residue substituted in place of the native aspartate at position 247 (GelC247$_{c44AC50A}$).

The variants of recombinant gelonin were constructed by restriction fragment manipulation or by overlap extension PCR with synthetic oligonucleotides. The sequences of the primers used for PCR are set out below. In each mutagenic primer sequence, the nucleotides corresponding to the changed amino acid, either a cysteine or an alanine residue, are underlined.

Gelo-9 (SEQ ID NO: 20)
Gelo-11 (SEQ ID NO: 18)
Gelo-16 (SEQ ID NO: 25)
Gelo-17 (SEQ ID NO: 27)
Gelo-18 (SEQ ID NO: 26)
Gelo-19 (SEQ ID NO: 60)
5' CAGCCATGGAATCCCATRGCTG 3'
GeloC-1 (SEQ ID NO: 28)
5' TCGATTGCGATCCTAAATAGTACTC 3'

GeloC-2 (SEQ ID NO: 29)
5' TTTAGGATCGCAATCGACGAACTTCAAG 3'

GeloC-3-2 (SEQ ID NO: 30)
5' GTTCGTCTGTAAAGATCCTAAATAGTACTCGA 3'

GeloC-4 (SEQ ID NO: 31)
5' GGATCTTTACAGACGAACTTCAAGAGT 3'

GeloC-5 (SEQ ID NO: 32)
5' TCTTGTGCTTCGTCGATAAAGATCC 3'

GeloC-6 (SEQ ID NO: 33)
5' ATCGACGAAGCACAAGAGTGCTATTTT 3'

GeloC-9 (SEQ ID NO: 34)
5' GTAAAACCATGCATAGCACTCTTGAAGTTCGT 3'

GeloC-10 (SEQ ID NO: 35)
5' AGTGCTATGCATGGTTTTACTTGATCAACTGC 3'

GeloC-13 (SEQ ID NO: 36)
5' AGCACATGTGGTGCCACTTATATRACCTA 3'

GeloC-14 (SEQ ID NO: 37)
5' TAAGTGGCACCACATGTGCTAAAGCTCACGGTG 3'

GeloC-15 (SEQ ID NO: 38)
5' TGATGTGGACAGTTGGCGGAAATA 3'

GeloC-16 (SEQ ID NO: 39)
5' GCCAACTGTCCACAGTCATTTGAAAGCGCTACC 3'

GeloC-17 (SEQ ID NO: 40)
5' GATGATCCTGGAAAGGCTTTCGTTTTGGTAGCGCTT 3'

GeloC-18 (SEQ ID NO: 41)
5' AAGCCTTTCCAGGATCATCAGC
TTTTTTGCGCAGCAATGGG 3'

GeloC-19 (SEQ ID NO: 42)
5' AAGCCTTTCCAGGATCATCACAT 3'

GeloC-20 (SEQ ID NO: 61)
5' CACATGTAAAACAAGACTTCAYMGGC 3

GeloC-21 (SEQ ID NO: 62)
5' TGAAGTCTTGTTTTAGATGTGTTTTTGAAGAGGCCT 3'

GeloC-22 (SEQ ID NO: 63)
5' ATGCCATATGCAATTATAAACCAACGGAGA 3'

GeloC-23 (SEQ ID NO: 64)
5' GGTTTATAATTGCATATGG
CATTTTCATCAAGTTTCTTG 3'

GeloC-24 (SEQ ID NO: 65)
5' CTTTCAACAATGCATTCGCCCGGCGAATAATAC 3'

GeloC-25 (SEQ ID NO: 66)
5' GCGAATGCATTGTTGAAAGTTATTTCTAATTTG 3'

GeloC-26 (SEQ ID NO: 67)
5' GTTTTGTGAGGCAGTTGAATTGGAAC 3'

GeloC-27 (SEQ ID NO: 68)
5' TTCAACTGCCTCACAAAACATRCCATTTGCACCT 3

GeloC-28 (SEQ ID NO: 69)
5' AAAAGCTGATGATCCTGGAAAGTG 3'

GeloC-29 (SEQ ID NO: 70)
5' TCCAGGATCATCAGCTTTTTTGCGCAGCAATGGGA 3' ara B2 (SEQ ID NO: 43)
5' GCGACTCTCTACTGTTTC 3'
HINDIII-2 (SEQ ID NO: 44)
5' CGTTAGCAATTTAACTGTGAT 3'

(1) Specifically, a cysteine was introduced at amino acid 247 of gelonin (an aspartic acid which corresponds to the cysteine at position 259 in the ricin A-chain) by PCR with mutagenic primers GeloC-3-2 and GeloC-4 in conjunction with primers HINDIII-2 (a primer located in the vector portion of pING3734 or pING3825), Gelo-9 and Gelo-8. Template DNA (pING3734) was amplified with GeloC-3-2 and HINDIII-2 and in a concurrent reaction with GeloC-4 and Gelo-9. The products of these reactions were mixed and amplified with the outside primers Gelo-8 and HINDIII-2. The reaction product was cut with EcoRI and XhoI, purified, and was inserted into plasmid pING3825 in a three-piece ligation. The DNA sequence of the $Gel_{c247}$ variant was then verified. The plasmid containing the sequence encoding $Gel_{c247}$ was designated pING3737 (deposited on Jun. 9, 1992 with the American Type Culture Collection, 12301 Parklawn Drive, Rockville, Md 20852 as ATCC Accession No. 69009).

(2–3) In the same manner, a cysteine residue was introduced in place of the amino acid at position 248 (a lysine) of gelonin with the mutagenic oligonucleotides GeloC-1 and GeloC-2 to generate analog $Gel_{c248}$ in plasmid pING3741, and a cysteine residue was introduced at amino acid position 239 (a lysine) with primers GeloC-9 and GeloC-10 to generate analog $Gel_{239}$ in plasmid pING3744.

(4) Also in the same manner, a cysteine residue was introduced at amino acid 244 (a lysine) of gelonin with mutagenic primers GeloC-5 and GeloC-6 to generate analog $Gel_{c244}$ in the plasmid designated pING3736. This variant was prepared by PCR using plasmid pING3734 as template DNA rather than pING3825. It therefore encodes the same N-terminal gelonin amino acid sequence as plasmids pING3737, pING3741, and pING3744, but includes the PCR primer-derived 5'-end 32 nucleotides instead of the native gelonin 5'-end nucleotides.

(5) A cysteine residue was introduced in place of the amino acid (a lysine) at position 10 of gelonin by a similar procedure. A cysteine was introduced with mutagenic primers GeloC-13 and GeloC-14 by amplifying pING3824 with ara B2 (a vector primer) and GeloC-14, and in a separate reaction, with GeloC-13 and Gelo- 11. These reaction products were mixed and amplified with the outside primers ara B2 and Gelo-11. The PCR product was cut with PstI and NcoI, purified, and cloned back into pING3825 to generate analog $Gel_{c10}$ in the plasmid designated pING3746 ( deposited on Jun. 9, 1992 with the American Type Culture Collection, 12301 Parklawn Drive, Rockville, Md 20852 as ATCC Accession No. 69008).

(6) The asparagine at position 60 of gelonin was replaced with a cysteine residue using two mutagenic oligos, GeloC-15 and GeloC-16, in conjunction with oligos ara B2 and Gelo-11 in the same manner as for the $Gel_{c10}$ variant. The plasmid encoding the $Gel_{c60}$ analog was designated pING3749.

(7) A cysteine was introduced at amino acid 103 (an isoleucine) by PCR with mutagenic primers GeloC-20 and GeloC-21 in conjunction with primers ara B2 and HINDIII-2. Template DNA (pING3733) was amplified with GeloC-21 and ara B2 and separately with GeloC-20 and HINDIII-2. The products of these reactions were mixed and amplified with the outside primers ara B2 and HINDIII-2. The reaction product was cut with NcoI and BclI, purified, and inserted into pING3825 digested with NcoI and BclI. The oligonucleotides used to place a cysteine at residue 103 also introduced an AflIII restriction site which was verified in the cloned gene. The plasmid containing the $Gel_{c103}$ analog was designated pING3760.

(8) A cysteine was introduced at position 146 (an aspartic acid) by a similar strategy. Template DNA (pING3733) was amplified with mutagenic primer GeloC-22 and Gelo-14 and separately with mutagenic primer GeloC-23 and Gelo-19. The products of these reactions were mixed, and amplified with Gelo-19 and Gelo-14. The reaction product was cut with BglII and EcoRI, and can be inserted into pING3825 in a three-piece ligation. The oligonucleotides used to place a cysteine at residue 146 also introduced a NdeI restriction site which can be verified in the cloned gene.

(9) To introduce a cysteine at position 184 (an arginine) of gelonin, template DNA (pING3733) was amplified with mutagenic primer GeloC-25 and ara B-2 and separately with mutagenic primer GeloC-24 and HINDIII-2. The products of these reactions were mixed, and amplified with ara B2 and Gelo-14. The reaction product was cut with NcoI and BclI, and inserted into pING3825 previously digested with NcoI and BclI. The oligonucleotides used to place a cysteine at residue 184 also introduced an NsiI restriction site which was verified in the cloned gene. The plasmid containing the sequence encoding the $Gel_{c184}$ variant was designated pING3761.

(10) A cysteine can be introduced at position 215 (a serine) by a similar strategy. Template DNA (pING3733) was amplified with mutagenic primer GeloC-27 and ara B2 and separately with mutagenic primer GeloC-26 and HINDIII-2. The products of these reactions were mixed, and amplified with ara B2 and HINDIII2. The reaction product was cut with EcoRI and BclI, and can be inserted into pING3825 in a three-piece ligation.

( 11 ) Another gelonin variant with a free cysteine residue was generated by replacing one of the two naturally occurring gelonin cysteine residues, the cysteine a position 50, with an alanine. Plasmid pING3824 was amplified with primers GeloC-17 and Gelo-11, and concurrently in a separate reaction with primers GeloC-19 and ara B2. The reaction products were mixed and amplified with ara B2 and Gelo-11. This product was cut with NcoI and BglII, and cloned back into the vector portion of pING3825 to generate pING3747 (ATCC 69101). This analog was designated $Gel_{c44}$ because it contains a cysteine available for disulfide bonding at amino acid position 44.

(12) A gelonin variant with the natural cysteine at position 44 changed to alanine was constructed by amplifying pING3733 using the mutagenic oligos GeloC-28 and GeloC-29 in conjunction with primers ara B2 and HINDIII-2. The amplified DNA was cut with NcoI and BglII, and cloned into a gelonin vector, generating pING3756. The variant generated was designated Gel$_{c50}$.

(13) A gelonin variant in which both the cysteine at position 44 and the cysteine at position 50 of gelonin were changed to alanine residues was constructed by overlap PCR of pING3824 using the mutagenic oligos GeloC-17 and GeloC-18 in conjunction with primers ara B2 and Gelo-11. This analog, like the native gelonin protein, has no cysteine residues available for conjugation. The plasmid encoding the analog was designated pING3750. The analog generated was designated Gel$_{c44AC50A}$.

(14) The triple mutant GeloninC247$_{c44AC50A}$ was constructed from the plasmids pING3824, pING3750 and pING3737. This variant contains an introduced cysteine at position 247 while both of the naturally occurring cysteine residues at positions 44 and 50 have been replaced with alanine and is desirable because disulfide linkage to an antibody is assured at only a single cysteine residue in the gelonin analog. Plasmid pING3824 was cut with NcoI and XhoI and the vector fragment was purified in an agarose gel. pING3750 was cut with NcoI and EcoRI and pING3737 was cut with EcoRI and XhoI. The NcoI-EcoRI fragment encodes the alanines at positions 44 and 50 while the EcoRI-XhoI fragment encodes the cysteine at position 247. Each of these fragments was purified and ligated to the NcoI to XhoI vector fragment. The resulting plasmid is named pING3752.

(15) The triple mutant $GeloninC10_{C44AC50A}$ was also constructed by assembly from previously assembled plasmids. In this case, pING3746 was cut with PstI and NcoI, while pING3750 was cut with NcoI and XhoI. Each of the insert fragments was purified by electrophoresis in an agarose gel, and the fragments were ligated into a PstI and XhoI digested vector fragment. The resulting vector was designated pING3753.

Each of the gelonin variants constructed was transformed into *E. coli* strain E 104. Upon induction of bacterial cultures with arabinose, gelonin polypeptide could be detected in the culture supernatants with gelonin-specific antibodies. There were no significant differences detected in the expression levels of gelonin from plasmids pING3734 and pING3825, or in the levels from any of the gelonin variants. Each protein was produced in E. coli at levels of approximately 1 g/l.

Example 4

Reticulocyte Lysate Assay

The ability of gelonin and recombinant gelonin analogs to inhibit protein synthesis in vitro was tested using a reticulocyte lysate assay (RLA) described in Press et al., *Immunol. Letters*, 14, 37–41 (1986). The assay measures the inhibition of protein synthesis in a cell-free system using endogenous globin mRNA from a rabbit red blood cell lysate. Decreased incorporation of tritiated leucine ($^3$HLeu) was measured as a function of toxin concentration. Serial log dilutions of standard toxin (the 30 kD form of ricin A-chain, abbreviated as RTA 30), native gelonin, recombinant gelonin (rGelonin) and gelonin analogs were tested over a range of 1 μg/ml to 1 pg/ml. Samples were tested in triplicate, prepared on ice, incubated for 30 minutes at 37° C., and then counted on an Inotec Trace 96 cascade ionization counter. By comparison with an uninhibited sample, the picomolar concentration of toxin (pM) which corresponds to 50% inhibition of protein synthesis ($IC_{50}$) was calculated. As is shown in Table 2 below, recombinant gelonin and most of its analogs exhibit activity in the RLA comparable to that of native gelonin. For some of the analogs (such as $Gel_{C239}$), RLA activity was diminished.

TABLE 1

| Toxin | $IC_{50}$ (pM) |
|---|---|
| RTA 30 | 2.5 |
| Gelonin | 15 |
| rGelonin | 11 |
| $Gel_{C10}$ | 60 |
| $Gel_{C44}$ | 20 |
| $Gel_{C50}$ | 47 |
| $Gel_{C60}$ | 26 |
| $Gel_{C239}$ | 955 |
| $Gel_{C244}$ | 32 |
| $Gel_{C247}$ | 12 |
| $Gel_{C248}$ | 47 |
| $Gel_{C44AC50A}$ | 16 |
| $GelC10_{C44AC50A}$ | 7 |
| $GelC247_{C44AC50A}$ | 20 |

Example 5

Preparation of Gelonin Immunoconjugates

Gelonin analogs of the invention were variously conjugated to murine (ATCC HB9286) and chimetic H65 antibody, (CH65) and cH65 antibody domains (including cFab, cFab' and $cF(ab')_2$ fragments) that are specifically reactive with the human T cell determinant CD5. H65 antibody was prepared and purified by methods described in U.S. patent application Ser. No. 07/306,433, supra and International Publication No. WO 89/06968, supra. Chimetic H65 antibody was prepared according to methods similar to those described in Robinson et at., *Human Antibodies and Hybridomas*, 2, 84–93 (1991).

(1) Conjugation to H65 antibodies

To expose a reactive sulfhydryl, the unpaired cysteine residues of the gelonin analogs were first reduced by incubation with 0.1 to 2 mM DTT (30–60 minutes at room temperature), and then were desalted by size-exclusion chromatography.

Specifically, the $Gel_{C248}$ analog (3.8 mg/ml) was treated with 2 mM DTT for 60 minutes in 0.1 M NaPhosphate, 0.25 M NaCl, pH 7.5 buffer. The $Gel_{C244}$ variant (7.6 mg/ml) was treated with 2 mM DTT for 30 minutes in 0.1 M NaPhosphate, 0.25 M NaCl, pH 7.5 buffer. The $Gel_{C247}$ analog (4 mg/ml) was treated with 2 mM DTT for 30 minutes in 0.1 M NaPhosphate, 0.5 M NaCl, pH 7.5 buffer with 0.5 mM EDTA. The $Gel_{C239}$ variant (3.2 mg/ml) was treated with 2 mM DTT for 30 minutes in 0.1 m NaPhosphate, 0.5 M NaCl, pH 7.5 buffer with 0.5 mM EDTA. The $Gel_{C44}$ analog (4.2 mg/ml) was treated with 0.1 mM DTT for 30 minutes in 0.1 M NaPhosphate, 0.1 M NaCl, pH 7.5 buffer with 0.5 mM EDTA. Lastly, the $Gel_{C10}$ variant (3.1 mg/ml) was treated with 1 mM DTT for 20 minutes in 0.1 M NaPhosphate, 0.1 M NaCl, pH 7.5 buffer with 1 mM EDTA.

The presence of a free sulfhydryl was verified by reaction with DTNB and the average value obtained was 1.4 ±0.65 SH/molecule. No free thiols were detected in the absence of reduction.

H65 antibody and chimeric H65 antibody were chemically modified with the hindered linker 5-methyl-2-iminothiolane (M2IT) at lysine residues to introduce a reactive sulfhydryl group as described in Goff et al., Bioconjugate Chem., 1, 381–386 (1990).

Specifically, for conjugation with Gel$_{C248}$ and Gel$_{C244}$, murine H65 antibody at 4 mg/mL was derivitized with 18x M2IT and 2.5 mM DTNB in 25 mM TEOA, 150 mM NaCl, pH 8 buffer for 1 hour at 23° C. The reaction gave 1.9 linkers per antibody as determined by DTNB assay.

For conjugation with Gel$_{C247}$ and Gel$_{C239}$, H65 antibody at 4.7 mg/mL was derivitized with 20x M2IT and 2.5 mM DTNB in 25 mM TEOA 150 mM NaCl, pH 8 buffer for 50 minutes at 23° C. The reaction gave 1.6 linkers per antibody as determined by DTNB assay.

Before reaction with Gel$_{C44}$, H65 antibody at 5.8 mg/mL was derivitized with 20x m2IT and 2.5 mM DTNB in 25 mM TEOA, 150 mM NaCl, pH 8 buffer for 30 minutes at 23°C. The reaction gave 1.5 linkers per antibody as determined by DTNB assay.

For conjugation with Gel$_{C10}$, H65 antibody at 2.2 mg/mL was derivitized with 10x m2IT and 2.5 mM DTNB in 25 mM TEOA, 150 mM NaCl, pH 8 buffer for 1 hour at 23° C. The reaction gave 1.4 linkers per antibody as determined by DTNB assay.

Chimeric H65 antibody was prepared for conjugation in a similar manner to murine H65 antibody.

Two methods were initially compared for their effectiveness in preparing immunoconjugates with recombinant gelonin. First, the native disulfide bond in recombinant gelonin was reduced by the addition of 2mM DTT at room temperature for 30 minutes. The reduced gelonin was recovered by size-exclusion chromatography on a column of Sephadex GF-05LS and assayed for the presence of free sulfhydryls by the DTNB assay. 1.4 free SH groups were detected. This reduced gelonin was then reacted with H65-(M2IT)-S-S-TNB (1.8 TNB groups/H65). Under these experimental conditions, little or no conjugate was prepared between reduced gelonin and thiol-activated H65 antibody.

In contrast, when both the recombinant gelonin and the H65 antibody were first derivitized with the cross-linker M2IT (creating gelonin-(M2IT)-SH and H65-(M2IT)-S-S-TNB) and then mixed together, H65-(M2IT)-S-S-(M2IT)-gelonin conjugate was prepared in good yield (toxin/antibody ratio of 1.6). The starting materials for this conjugation (gelonin-(M2IT)-SH and H65-(M2IT)-S-S-TNB) contained linker/protein ratios of 1.2 and 1.4, respectively. Native gelonin was derivatized in a similar manner prior to conjugation to murine or chimeric H65 antibody.

The reduced gelonin analogs were mixed with H65-(M2IT)-S-S-TNB to allow conjugation. The following conjugation reactions were set up for each analog: 23 mg (in 7.2 ml) of H65-M2IT-TNB were mixed with a 5-fold molar excess of Gel$_{C248}$ (23 mg in 6 ml) for 2 hours at room temperature, then for 18 hours overnight at 4° C.; 23 mg (in 7.3 ml) of H65-m2IT-TNB were mixed with a 5-fold molar excess of Gel$_{C244}$ (23 mg in 3 ml) for 3 hours at room temperature, then for 18 hours overnight at 4° C.; 9 mg (in 2.8 mL) of H65-m2IT-TNB were mixed with a 5-fold molar excess of Gel$_{C247}$ (9 mg in 2.25 mL) for 2 hours at room temperature, then for 5 nights at 4° C.; 9 mg (in 2.8 mL) of H65-m2IT-TNB were mixed with a 5-fold molar excess of Gel$_{C239}$ (9mg in 2.6 mL) for 2 hours at room temperature, then at 4° C. for 3 days; 12 mg (in 1.9 mL) of H65-m2IT-TNB were mixed with a 5.6-fold molar excess of Gel$_{C44}$ (13.44 mg in 3.2 mL) for 4.5 hours at room temperature, then 4° C. overnight; and 11 mg of H65-m2IT-TNB were mixed with a 5-fold molar excess of Gel$_{C10}$ (11 mg in 3.5 mL) for 4 hours at room temperature, then at 4° C. overnight.

Following conjugation, unreacted M2IT linkers on the antibody were quenched with 1:1 mole cysteamine to linker for 15 minutes at room temperature. The quenched reaction solution was then loaded onto a gel filtration column [Sephadex G-150 (Pharmacia) in the case of Gel$_{C248}$, GelC247, Gel$_{C244}$ and Gel$_{C239}$ and an AcA-44 column (IBF Biotecnics, France) in the case of Gel$_{C44}$ and Gel$_{C10}$]. The reactions were run over the gel filtration columns and eluted with 10 mM Tris, 0.15M NaCl pH 7. The first peak off each column was loaded onto Blue Toyopearl ® resin (TosoHaas, Philadelphia, Pa.) in 10 mM Tris, 30 mM NaCl, pH 7 and the product was eluted with 10 mM Tris, 0.5M NaCl, pH 7.5.

Samples of the final conjugation products were run on 5% non-reduced SDS PAGE, Coomassie stained and scanned with a Shimadzu laser densitometer to quantitate the number of toxins per antibody (T/A ratio). The yield of final product for each analog conjugate was as follows: Gel$_{C248}$, 17 mg with a T/A ration of 1.6; Gel$_{C247}$, 1.1 mg with a T/A ratio of 1; Gel$_{C244}$, 4.5 mgs with a T/A ratio of 1.46; Gel$_{C239}$, 2.9 mg with a T/A ratio of 2.4; Gel$_{C44}$, 7.3 mg with a T/A ratio of 1.22; and Gel$_{C10}$, 6.2 mg with a T/A ratio of 1.37. Conjugation efficiency (i.e., conversion of free antibody to immunoconjugate) was significantly greater (~80%) for some analogs (Gel$_{C10}$, Gel$_{C44}$, Gel$_{C239}$, Gel$_{C247}$, and Gel$_{C248}$) than for others (~10%, Gel$_{C244}$).

(2) Conjugation to antibody fragments

Analogs Gel$_{C247}$ and Gel$_{C44}$ were conjugated to various chimeric [cFab, cFab' and cF(ab')$_2$] and "human engineered"[he1 Fab, he2 Fab, he3 Fab, he1 Fab' and he1 F(ab')$_2$] antibody fragments. Chimetic H65 antibody fragments may be prepared according to the methods described in U.S. patent application Ser. No. 07/714,175, supra and in International Publication No. WO 89/00999, supra. The DNA sequences encoding the variable regions of H65 antibody fragments that were human engineered (referring to the replacement of selected murine-encoded amino acids to make the H65 antibody sequences less immunogenic to humans) according to the methods described in co-pending, co-owned U.S. Pat. application Ser. No. 07/808,454 filed Dec. 13, 1991 which is incorporated by reference herein, are set out in SEQ ID NO: 71 (the kappa chain of he1 and he2), SEQ ID NO: 72 (the gamma chain of he1), SEQ ID NO: 73 (the gamma chain of he2 and he3) and SEQ ID NO: 74 (the kappa chain of he3)

The chimetic H65 antibody fragments were conjugated to Gel$_{C247}$ analog basically as described below for conjugation of human engineered Fab and Fab' fragments to Gel$_{C247}$ and Gel$_{C44}$.

(a) he1 Fab-Gel$_{C247}$

The he1 Fab was dialyzed into 25 mM TEOA buffer, 250 mM NaCl, pH 8 and then concentrated to 6.8 mg/mL prior to derivitization with the M2IT cross-linker. For the linker reaction, M2IT was used at 20-fold molar excess, in the presence of 2.5 mM DTNB. The reaction was allowed to proceed for 30 minutes at room temperature, then desalted on GF05 (gel filtration resin) and equilibrated in 0.1 M Na Phosphate, 0.2M NaCl, pH 7.5. A linker number of 1.8 linkers per Fab was calculated based on the DTNB assay. The he1 Fab-M2IT-TNB was concentrated to 3.7 mg/mL prior to conjugation with Gel$_{C247}$.

Gel$_{C247}$ at 12.8 mg/mL in 10 mM Na Phosphate, 0.3M NaCl, was treated with 1 mM DTT, 0.5 mM EDTA for 20 minutes at room temperature to expose a reactive sulfhydryl for conjugation and then was desalted on GF05 and equilibrated in 0.1M Na Phosphate, 0.2M NaCl, pH 7.5. Free thiol content was determined to be 0.74 moles of free SH per mole of Gel$_{C247}$ using the DTNB assay. The gelonin was concentrated to 8.3 mg/mL prior to conjugation with activated antibody.

The conjugation reaction between the free thiol on Gel$_{C247}$ and the derivitized hel Fab-M2IT-TNB, conditions were as follows. A 5-fold excess of the gelonin analog was added to activated he 1 Fab-M2IT-TNB (both proteins were in 0.1M Na Phosphate, 0.2M NaCl, pH7.5) and the reaction mixture was incubated for 3.5 hours at room temperature and then overnight at 4° C. Following conjugation, untreated M2IT linkers were quenched with 1:1 mole cysteamine to linker for 15 minutes at room temperature. The quenched reaction solution was loaded onto a gel filtration column (G-75) equilibrated with 10 mM Tris, 150 mM NaCl, pH 7. The first peak off this column was diluted to 30 mM NaCl with 10 mM Tris, pH7 and loaded on Blue Toyopearl ®. The product was eluted with 10 mM Tris, 0.5M NaCl, pH 7.5.

(b) he1 Fab '-Gel$_{C247}$

Similarly, the H65 he1 Fab' fragment was dialyzed into 25 mM TEOA buffer, 400 mM NaCl, pH 8 at 2.9 mg/mL prior to derivitization with the M2IT crosslinker. For the linker reaction, M2IT was used at 20-fold molar excess, in the presence of 2.5 mM DTNB. The reaction was allowed to proceed for 1 hour at room temperature then it was desalted on GF05 (gel filtration resin) and equilibrated in 0.1 M Na Phosphate, 0.2M NaCl, pH 7.5. A linker number of 1.6 linkers per Fab' was calculated based on the DTNB assay. The he1 Fab'-M2IT-TNB was concentrated to 3.7 mg/mL prior to conjugation with Gel$_{C247}$ The Gel$_{C247}$ at 77 mg/mL was diluted with in 10 mM Na Phosphate, 0.1M NaCl to a concentration of 5 mg/mL, treated with 1 mM DTT, 0.5 mM EDTA for 30 minutes at room temperature to expose a free thiol for conjugation and then was desalted on GF05 and equilibrated in 0.1M Na Phosphate, 0.2M NaCl, pH 7.5. Free thiol content was determined to be 1.48 moles of free SH per mole of Gel$_{C247}$ using the DTNB assay. The Gel$_{C247}$ was concentrated to 10 mg/mL prior to conjugation with activated he1 Fab'-M2IT-TNB.

For the reaction between the free thiol on Gel$_{C247}$ and the derivitized he1 Fab'-M2IT-TNB, conditions were as follows. A 5.7-fold molar excess of gelonin was added to activated he1 Fab'-M2IT-TNB and the final salt concentration was adjusted to 0.25M. The reaction mix was incubated for 1.5 hours at room temperature and then over the weekend at 4° C. Following conjugation, unreacted M2IT linkers were quenched with 1:1 mole cysteamine to linker for 15 minutes at room temperature. The quenched reaction solution was loaded onto a gel filtration column (AcA54) equilibrated with 10 mM Tris, 250 mM NaCl, pH 7.5. The first peak off this column was diluted to 20 mM NaCl with 10 mM Tris, pH 7 and loaded on Blue Toyopearl ® which was equilibrated in 10 mM Tris, 20 mM NaCl, pH 7. The column was then washed with 10 mM Tris, 30 mM Nacl, pH 7.5. The product was eluted with 10 mM Tris, 1M NaCl, pH 7.5.

(c) he2 Fab Gel$_{C44}$

The he2 Fab was dialyzed overnight into 25 mM TEOA, 0.25M NaCl, pH 8 buffer and then concentrated to 13.3 mg/mL prior to derivitization with the M2IT crosslinker. For the linker reaction, M2IT was used in a 20-fold molar excess in the presence of 2.5 mM DTNB. The reaction was allowed to proceed for 20 minutes at room temperature and was then alesalted on a GF05-LS (gel filtration) column, equilibrated in 0.1M Na Phosphate, 0.2M NaCl with 0.02% Na azide. A linker number of 1.7 linkers per Fab-M2IT-TNB was calculated based on the DTNB assay. After derivitization and gel filtration, the he2 Fab concentration was 5.2 mg/mL.

Gel$_{C44}$ at 8.33 mg/mL in 10 mM Na Phosphate, pH 7.2 was treated with 5 mM DTT and 0.5 mM EDTA for 30 minutes at room temperature to expose a reactive thiol for conjugation and then was desalted on GF05-LS resin equilibrated in 0.1M Na Phosphate, 0.1M NaCl with 0.5 mM EDTA plus 0.02 % Na azide, pH 7.5. Free thiol content was determined to be 0.83 moles of free SH per mole of Gel$_{C44}$ using the DTNB assay. The gelonin was concentrated to 11.4 mg/mL prior to conjugation with activated he2 Fab.

The conjugation reaction conditions between the free thiol on Gel$_{C44}$ and the derivitized he2 Fab-M2IT-TNB were as follows. A 3-fold excess of the gelonin analog was added to activated he2 Fab-M2IT-TNB (both proteins were in 0.1 M Na Phosphate, 0.1M NaCl, pH 7.5 but the gelonin solution contained 0.5 mM EDTA as well). The reaction mixture was concentrated to half its original volume, then the mixture was incubated for 4 hours at room temperature followed by 72 hours at 4° C. Following the incubation period the efficiency of conjugation was estimated at 70–75 % by examination of SDS PAGE.

Following conjugation the excess M2IT linkers were quenched by incubation with 1:1 mole cysteamine to linker for 15 minutes at room temperature. The quenched reaction as loaded onto a gel filtration column (G-75) equilibrated in 10 mM Tris, 0.15M NaCl, pH 7. The first peak off this column was diluted to 30 mM NaCl with 10 mM Tris, pH 7 and loaded onto a Blue Toyopearl ® (TosoHaas) column. The product was eluted with 10 mM Tris, 1M NaCl, pH 7.5.

(d) he3 Fab Gel$_{C44}$

Similarly, the he3 Fab was dialyzed overnight into 25 mM TEOA, 0.25M NaCl, pH 8 buffer and then concentrated to 5 mg/mL prior to derivitization with the M2IT crosslinker. For the linker reaction, M2IT was used in a 10-fold molar excess in the presence of 2.5 mM DTNB. The reaction was allowed to proceed for 45 minutes at room temperature and was then alesalted on a GF05-LS (gel filtration) column, equilibrated in 0.1M Na Phosphate, 0.2M NaCl with 0.02% Na azide. A linker number of 1M2IT per Fab-M2IT-TNB was calculated based on the DTNB assay. After derivitization and gel filtration, the he3 Fab concentration was 5.3 mg/mL.

Gel$_{C44}$ at 7.8 mg/mL in 0.1M Na Phosphate, 0.1M NaCl, pH 7.5 was treated with 1.5 mM DTT and 1 mM EDTA for 30 minutes at room temperature to expose a reactive thiol for conjugation and then was desalted on GF05-LS resin equilibrated in 0.1M Na Phosphate, 0.1M NaCl plus 0.02% Na azide, pH 7.5. Free thiol content was determined to be 0.66 moles of free SH per mole of Gel$_{C44}$ using the DTNB assay. The gelonin was concentrated to 5.2 mg/mL prior to conjugation with activated he3 Fab.

The conjugation reaction conditions between. the free thiol on Gel$_{C44}$ and the derivitized he3 Fab-M2IT-TNB were as follows. A 5-fold excess of the gelonin analog was added to activated he3 Fab-M2IT-TNB (both proteins were in 0.1M Na phosphate 0.1M NaCl, pH 7.5). The reaction mixture was incubated for 2 hours at room temperature followed by 72 hour at 4° C. Following the incubated period the efficiency of conjugation was estimated at 70–75 % by examination of SDS PAGE.

Following conjugation, the excess M2IT linkers were quenched by incubation with 1:1 mole cysteamine to linker for 15 minutes at room temperature. The quenched reaction was loaded onto a GammaBind G (immobilized protein G affinity resin, obtained from Genex, Gaithersburg, Md.) equilibrated in 10 mM Na Phosphate, 0.15M NaCl, pH 7. It was eluted with 0.5M NaOAc, pH 3 and neutralized with Tris. It was dialyzed into 10 mM Tris, 0.15M NaCl, pH 7 overnight, then diluted to 30 mM NaCl with 10 mM Tris, pH 7 and loaded onto a blue Toyopearl ® (TosoHaas) column. The product was eluted with 10 mM Tris, 1M NaCl, pH 7.5

EXAMPLE 6

Whole Cell Kill Assays

Immunoconjugates prepared with gelonin and gelonin analogs were tested for cytotoxicity against an acute lymphoblastoid leukemia T cell line (HSB2 cells) and against human peripheral blood mononuclear cells (PBMCs). Immunoconjugates of ricin A-chain with H65 antibody (H65-RTA) and antibody fragments were also tested. The ricin A-chain (RTA) as well as the H65-RTA immunoconjugates were prepared and purified according to methods described in U.S. patent application Ser. No. 07/306,433, supra and in International Publication No. WO 89/06968, Supra.

Briefly, HSB2 cells were incubated with immunotoxin and the inhibition of protein synthesis in the presence of immunotoxin was measured relative to untreated control cells. The standard immunoconjugates H65-RTA (H65 derivitized with SPDP linked to RTA), H65-Gelonin and H65-rGelonin, H65 fragment immunoconjugate, and gelonin immunoconjugate samples were diluted with RPMI without leucine at half-log concentrations ranging from 2000 to 0.632 ng/ml. All dilutions were added in triplicate to microtiter plates containing 1×10$^5$ HSB2 cells. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar concentration (pM) of immunotoxin which resulted in a 50% inhibition of protein synthesis (IC$_{50}$) was calculated. In order to normalize for conjugates containing differing amounts of toxin or toxin analog, the cytotoxicity data were converted to picomolar toxin (pM T) by multiplying the conjugate IC$_{50}$ (in pM) by the toxin/antibody ratio which is unique to each conjugate preparation.

The PMBC assays were performed as described by Fishwild et al., *Clin. and Exp. Immunol.*, 86, 506–513 (1991) and involved the incubation of immunoconjugates with PBMCs for a total of 90 hours. During the final 16 hours of incubation, $^3$H-thymidine was added; upon completion, immunoconjugate-induced inhibition of DNA synthesis was quantified. The activities of the H65 and chimetic H65 antibody conjugates against HSB2 cells and PBMC cells are listed in Table 2 below.

TABLE 2

| Conjugate | IC$_{50}$ (PM T) | |
|---|---|---|
| | HSB2 Cells | PBMCs |
| H65-RTA | 143 | 459 |
| H65-(M2IT)-S—S-(M2IT)-Gelonin | 1770 | 81 |
| H65-(M2IT)-S—S-(M2IT)-rGelonin | 276 | 75 |
| H65-(M2IT)-S—S-Gel$_{C10}$ | 140 | 28 |
| H65-(M2IT)-S—S-Gel$_{C44}$ | 99 | 51 |
| H65-(M2IT)-S—S-Gel$_{C239}$ | 2328 | 180 |
| H65-(M2IT)-S—S-Gel$_{C244}$ | >5000 | >2700 |
| H65-(M2IT)-S—S-Gel$_{C247}$ | 41 | 35 |
| H65-(M2IT)-S—S-Gel$_{C248}$ | 440 | 203 |
| cH65-RTA30 | 60 | 400 |
| cH65-(M21T)-S—S-(M2IT)-Gelonin | 1770 | 140 |
| cH65-(M2IT)-S—S-(M2IT)-rGelonin | 153 | 120 |
| cH65-(M2IT-S—S-Gel$_{C239}$ | >7000 | 290 |
| cH65-(M2IT-S—S-Gel$_{C247}$ | 34 | 60 |
| cH65-(M21T)-S—S-Gel$_{C248}$ | 238 | 860 |

Against HSB2 cells, many of the gelonin analog immunoconjugates were significantly more potent than conjugates prepared with native gelonin or recombinant, unmodified gelonin, both in terms of a low IC$_{50}$ value, but also in terms of a greater extent of cell kill. Against human PBMCs, the gelonin analog conjugates were at least as active as native and recombinant gelonin conjugates. Importantly, however, some of the conjugates (for example, Gel$_{C10}$, Gel$_{C44}$ and Gel$_{C247}$) exhibited an enhanced potency against PBMCs compared to native and recombinant gelonin conjugates, and also exhibited an enhanced level of cell kill (data not shown).

The activities of the H65 antibody fragment conjugates against HSB2 cells and PBMC cells are listed in Tables 3 and 4 below, wherein extent of kill in Table 4 refers to the percentage of protein synthesis inhibited in HSB2 cells at the highest immunotoxin concentration tested (1μg/ml).

TABLE 3

| Conjugate | IC$_{50}$ (pM T) | |
|---|---|---|
| | HSB2 Cells | PBMCs |
| cFab'-RTA 30 | 530 | 1800 |
| cFab'-rGelonin | 135 | 160 |
| cFab'-Gel$_{C247}$ | 48 | 64 |
| cF(ab')$_2$-RTA 30 | 33 | 57 |
| cF(ab')$_2$-rGelonin | 55 | 34 |
| cF(ab')$_2$Gel$_{C247}$ | 23 | 20 |
| cF(ab')$_2$-Gel$_{C248}$ | 181 | 95 |

TABLE 4

| Conjugate | IC$_{50}$ (pM T) | |
|---|---|---|
| | HSB2 Cells | Extent of Kill |
| hel Fab'-Gel$_{C247}$ | 57.7 | 93% |
| hel Fab-Gel$_{C247}$ | 180 | 94% |
| he2 Fab-Gel$_{C44}$ | 363 | 91% |
| he3 Fab-Gel$_{C44}$ | 191 | 93% |
| cFab'-Gel$_{C247}$ | 47.5 | 93% |
| cF(ab')$_2$-rGelonin | 45.4 | 85% |
| F(ab')$_2$-Gel$_{C247}$ | 77.5 | 83% |
| cF(ab')$_2$-Gel$_{C247}$ | 23.2 | 85% |

The cFab '-Gel$_{247}$ immunoconjugate is clearly more cytotoxic than cFab' conjugates with recombinant gelonin or RTA 30.

EXAMPLE 7

Solubility

Recombinant gelonin and the gelonin analogs exhibited enhanced solubility in comparison to both native gelonin and RTA30. In addition, recombinant gelonin and gelonin analog immunoconjugates exhibited enhanced solubility relative to immunoconjugates prepared with native gelonin and RTA30. This enhanced solubility was particularly noteworthy for recombinant gelonin and analog conjugates prepared with chimeric Fab fragments.

Disulfide Bond Stability Assay

The stability of the disulfide bond linking a RIP to a targeting molecule (such as an antibody) is known to influence the lifespan of immunoconjugates in vivo [see Thorpe et al., *Cancer Res.*, 47, 5924–5931 (1987)]. For example, conjugates in which the disulfide bond is easily broken by reduction in vitro are less stable and less efficacious in animal models [see Thorpe et al., *Cancer Res.*, 48, 6396–6403 (1988)].

Immunoconjugates prepared with native gelonin, recombinant gelonin and gelonin analogs were therefore examined in an in vitro disulfide bond stability assay similar to that described in Wawrzynczak et al., *Cancer Res.*, 50, 7519–7526 (1990). Conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparison with the amount of RIP released by high concentrations of 2-mercaptoethanol (to determine 100% release), the concentration of glutathione required to release 50% of the RIP (the $RC_{50}$) was calculated. The results of assays for H65 antibody conjugates are set out in Table 5 below.

TABLE 5

| Conjugate | $RC_{50}$ (mM) |
|---|---|
| H65-RTA 30 | 3.2 |
| H65-(M2IT)-S—S-(M2IT)-gelonin | 11.1 |
| H65-(M2IT)-S—S-(M2IT)-rGelonin | 3.0 |
| H65-(M2IT)-S—S-$Gel_{C10}$ | 2.5 |
| H65-(M2IT)-S—S-$Gel_{C44}$ | 0.6 |
| H65-(M2IT)-S—S-$Gel_{C239}$ | 774.0 |
| H65-(M2IT)-S—S-$Gel_{C244}$ | 1.2 |
| H65-(M2IT)-S—S-$Gel_{C247}$ | 0. 1 |
| H65-(M2IT)-S—S-$Gel_{C248}$ | 0.4 |
| cH65-RTA 30 | 2.50 |
| cH65-(M2IT)-S—S-(M2IT)-rGelonin | 2.39 |
| cH65-(M2IT)-S—S-$Gel_{C247}$ | 0.11 |
| cH65-(M2IT)-S—S-$Gel_{C248}$ | 0.32 |

The foregoing results indicate that the stability of the bonds between the different gelonin proteins and H65 antibody varied greatly. With the exception of $Gel_{C10}$ and $Gel_{C239}$, most of the gelonin analogs resulted in conjugates with linkages that were somewhat less stable in this in vitro assay than the dual-linker chemical conjugate. The stability of the $Gel_{C239}$ analog, however, was particularly enhanced.

The results of the assay for H65 antibody fragment conjugates are set out in Table 6 below.

TABLE 6

| Conjugate | $RC_{50}$ (mM) |
|---|---|
| he1 Fab'-$Gel_{C247}$ | 0.07 |
| cFab'-Gelonin | 1.27 |

TABLE 6-continued

| Conjugate | $RC_{50}$ (mM) |
|---|---|
| cFab'-$Gel_{C247}$ | 0.08 |
| cF(ab')$_2$-RTA 30 | 1.74 |
| cF(ab')$_2$-rGelonin | 2.30 |
| cF(ab')$_2$-$Gel_{C247}$ | 0.09 |
| cF(ab')$_2$-$Gel_{C248}$ | 0.32 |
| he2 Fab-$Gel_{C44}$ | 0.46 |
| he3 Fab-$Gel_{C44}$ | 0.58 |

From the $RC_{50}$ results presented in Tables 5 and 6, it appears that the particular RIP analog component of each immunotoxin dictates the stability of the immunotoxin disulfide bond in vitro.

EXAMPLE 8

Pharmacokinetics of Conjugates to H65 Antibody

The pharmacokinetics of gelonin analogs $Gel_{C247}$, $Gel_{C44}$ and $Gel_{C10}$ linked to whole H65 antibody was investigated in rats. An IV bolus of 0.1 mg/kg of $^{125}$I-labelled immunoconjugate H65-(M2IT)-S-S-$Gel_{C247}$, H65-(M2IT)-S-S-$Gel_{C44}$ or H65-(M2IT)-S-S-$Gel_{C10}$ was administered to male Sprague-Dawley rats weighing 134–148 grams. Serum samples were collected from the rats at 3, 15, 30 and 45 minutes, and at 1.5, 2, 4, 6, 8, 18, 24, 48, 72, and 96 hours. Radioactivity (cpm/ml) of each sample was measured, and SDS-PAGE was performed to determine the fraction of radioactivity associated with whole immunoconjugate. Immunoconjugate associated serum radioactivity was analyzed using the computer program PCNONLIN (SCI Software, Lexington, Ky.). Table 7 below lists the pharmacokinetic parameters of the immunoconjugates. In the table, the standard error for each value is indicated and a one way analysis of variance is presented, IC is the immunoconjugate (specified by the abbreviation for the gelonin variant that is part of the immunoconjugate) n is the number of animals in the study, Vc is the central volume of distribution, Cl is the clearance, MRT is the total body-mean residence time, Alpha is the α half-life and Beta is the β half-life of the immunoconjugate.

TABLE 7

| IC | Vc (ml/kg) | Cl (ml/hr/kg) | MRT (hours) | Alpha (hours) | Beta (hours) |
|---|---|---|---|---|---|
| H65 $Gel_{C247}$ n = 32 | 65.3 ± 3.4 | 11.0 ± 0.4 | 16.5 ± 1.9 | 2.3 ± 0.2 | 20.5 ± 3.0 |
| H65 $Gel_{C44}$ n = 38 | 61.9 ± 2.4 | 4.1 ± 0.1 | 22.7 ± 0.7 | 3.0 ± 0.7 | 17.8 ± 0.8 |
| H65 $Gel_{C10}$ n = 45 | 59.2 ± 1.3 | 2.5 ± 0.04 | 42.7 ± 1.1 | 3.3 ± 0.3 | 32.9 ± 1.1 |
| p-value | 0.176 | <0.0001 | <0.0001 | 0.303 | <0.0001 |

The $Gel_{C247}$ immunoconjugate was found to have α and β half lives of 2.3 and 20 hours, with a total mean residence time of 17 hours. The 72 and 96 hour time points were excluded from analysis because of the poor resolution of immunoconjugate associated radioactivity on the SDS-PAGE gel for these serum samples.

Because in vitro studies suggested that the $Gel_{C10}$ immunoconjugate had greater disulfide bond stability, it was anticipated that its half lives in vivo would be longer relative to the $cys_{247}$ form of the immunoconjugate. The β half life of the immunoconjugate was about 33 hours compared to 20 hours for the $Gel_{C247}$ conjugate. The total mean residence time was also much greater for the $Gel_{C10}$ immunoconjugate (42 hours versus 42 hours for the $Gel_{247}$ conjugate). In addition, the clearance of the Gel$_{C10}$ immunoconjugate was 2.5 ml/hr/kg, about four times less than that of the Gel$_{C247}$ immunoconjugate (11 ml/hr/kg). As also predicted from the in vitro disulfide stability data, the clearance of the Gel$_{C44}$ immunoconjugate was intermediate between those of the Gel$_{C10}$ and Gel$_{C247}$ immunoconjugates.

Based on these studies, the Gel$_{C10}$ analog conjugated to H65 antibody has greater in vivo stability than the Gel$_{C44}$ and Gel$_{C247}$ analogs conjugated to H65 antibody (as determined by the longer mean residence time and clearance rates), although the properties of the Gel$_{C44}$ immunoconjugate more closely resembled those of the Gel$_{C10}$ immunoconjugate than the Gel$_{C247}$ immunoconjugate.

Pharmacokinetics of Conjugates to H65 Antibody Fragments

The pharmacokinetics of Gel$_{C247}$ and Gel$_{C44}$ analogs linked to human engineered H65 Fab fragments were also investigated in rats. An IV bolus of 0.1 mg/kg of $^{125}$I-labelled he1 H65 Fab-Gel$_{C247}$, he2 H65 Fab-Gelc44 or he3 H65 Fab-Gel$_{C44}$ was administered to male Sprague-Dawley rats weighing 150–180 grams. Serum samples were collected at 3, 5, 15, 20, 30, and 40 minutes, and 1, 1.5, 3, 6, 8, 18, 24, 32, 48, and 72 hours, and were analyzed by ELISA using rabbit anti-Gelonin antibody as the capture antibody and biotin-labelled goat anti-human kappa light chain antibody as the secondary antibody. Results of the analysis are presented in Table 8 below. In the table, the standard error for each value is shown, and IC is the immunoconjugate, n is the number of animals in the study, Vc is the central volume of distribution, Vss is the steady state volume of distribution, Cl is the clearance, MRT is the total body mean residence time, Alpha is the $\alpha$ half-life and Beta is the $\beta$ half-life of the indicated conjugate.

TABLE 8

| IC | Vc (ml/kg) | Vss (ml/hr/kg) | Cl (ml/hr/kg) | MRT (hours) | Alpha (hours) | Beta (hours) |
|---|---|---|---|---|---|---|
| he1 Gel$_{C247}$ n = 27 | 48 ± 3 | 133 ± 7 | 62 ± 3 | 2.1 ± 0.1 | 0.33 ± 0.03 | 3.0 fixed |
| he2 Gel$_{C44}$ n = 28 | 54 ± 5 | 141 ± 8 | 53 ± 3 | 2.7 ± 0.2 | 0.37 ± 0.04 | 3.1 fixed |
| he3 Gel$_{C44}$ n = 33 | 77 ± 6 | 140 ± 20 | 57 ± 3 | 2.5 ± 0.4 | 0.58 ± 0.11 | 3.0 ± 1.0 |

Comparing the three immunoconjugates, the pharmacokinetics of he1 H65 Fab-Gel$_{C247}$, he2 H65 Fab-Gel$_{C44}$ and he3 Fab-Gel$_{C44}$ were very similar, having similar alpha and beta half-lives, mean residence times, and clearance, particularly when comparing parameters obtained from the ELISA assayed curves. This is in contrast to their whole antibody immunoconjugate counterparts, where the clearance of Gel$_{C247}$ immunoconjugate (11 ml/kg/hr) was three-fold greater than that of Gel$_{C44}$ immunoconjugate (4 ml/kg/hr). This suggests that cleavage of the disulfide bond linking the Fab fragment and gelonin is not as important for the serum clearance of Fab immunoconjugates as for whole antibody immunoconjugates.

Immunogencity of Immunoconjugates

Outbred Swiss/Webster mice were injected repeatedly (0.2 mg/kg each injection) with murine H65 antibody conjugates prepared with RTA, RTA30 and recombinant gelonin. The cycle was such that each animal was injected on days 1 and 2, and then the injections were repeated 28 and 29 days later. The animals received 5 such cycles of injections. One week and three weeks following each series of injections, blood was collected and the amount of anti-RIP antibodies present was determined by ELISA; peak titers for each cycle are shown in Table 9. RTA and RTA30 generated strong responses which began immediately following the first cycle of injections and remained high throughout the experiment. In contrast, no immune response was detected for the gelonin conjugate, even after 5 cycles of injections. When the conjugates were mixed with Complete Freund Adjuvant and injected i.p. into mice, anti-RTA and RTA-30 antibodies were readily detected after several weeks. These data indicate that anti-gelonin antibodies, if generated, would have been detected by the ELISA assay, and suggest that recp-,bomamt gelonin may be much less immunogenic in animals than is RTA.

TABLE 9

| Cycle | H65-RTA | H65-RTA30 | H65-rGel |
|---|---|---|---|
| Prebleed | 100 | 100 | 100 |
| Cycle 1 | 168 | 117 | 100 |
| Cycle 2 | 4208 | 1008 | 100 |
| Cycle 3 | 7468 | 3586 | 100 |
| Cycle 4 | 5707 | 3936 | 100 |
| Cycle 5 | 4042 | 2505 | 100 |

EXAMPLE 9

A human peripheral blood lymphocyte (PBL)-reconstituted, severe combined immunodeficient mouse model was utilized to evaluate the in vivo efficacy of various immunoconjugates comprising the gelonin analogs Gel$_{C247}$ and Gel$_{C44}$. Immunoconjugates were tested for the capacity to deplete human blood cells expressing the CD5 antigen.

Human PBL Donors and Cell Isolation

Human peripheral blood cells were obtained from lymphapheresis samples (HemaCare Corporation, Sherman Oaks, Calif.) or venous blood samples (Stanford University Blood Bank, Palo Alto, Calif.) collected from healthy donors. Blood cells were enriched for PBLs using Ficoll-Hypaque density gradient centrifugation (Ficoll-Paque ®; Pharmacia, Piscataway, N.J.) and subsequently washed 4 times with PBS. Residual erythrocytes were lysed with RBC lysing buffer (16 μM ammonium chloride, 1 mM potassium bicarbonate, 12.5 μM EDTA) during the second wash. Cell viability in the final suspension was >95% as assessed by trypan blue dye exclusion.

Animals and Human PBL Transfer

CB.17 scid/scid (SCID) mice were purchased from Taconic (Germantown, N.Y.) or were bred under sterile conditions in a specific pathogen-free animal facility (original breeding pairs were obtained from Hana Biologics, Alameda, Calif.). Animals were housed in filter-top cages and were not administered prophylactic antibiotic treatment. Cages, bedding, food and water were autoclaved before use. All manipulations with animals were performed in a laminar flow hood.

Untreated SCID mice were bled for determination of mouse Ig levels. Human PBL-injected mice were bled at various intervals for quantitation of human Ig and sIL-2R. Blood collection was from the retro-orbital sinus into heparinized tubes. Blood samples were centrifuged at 300×g for 10 min, and plasma was collected and stored at −70° C. Mouse and human Ig were quantified using standard sandwich ELISAs. Briefly, flat-bottom microtiter plates (MaxiSorp Immuno-Plates, Nunc, Roskilde, Denmark) were coated overnight at 4° C. with goat anti-mouse IgG+IgA+IgM (Zymed Laboratories, Inc., South San Francisco, Calif.) or goat anti-human Igs (Tago, Inc., Burlingame, Calif.) in bicarbonate buffer, pH 9.6. Plates were blocked for 2 hours at room temperature with 1% BSA in Tris-buffered saline, pH 7.5 (TBS), and then incubated at 37° C. for 1 hour with standards or samples serially-diluted in TBS/1% BSA/0.05% Tween 20. Standards used were a monoclonal mouse IgG2a (IND1 anti-melanoma; XOMA Corporation, Berkeley, Calif.) and polyclonal human Ig (Sigma Chemical Co., St. Louis, Mo.). Subsequently, plates were washed with TBS/Tween 20 and incubated at 37° C. for 1 hour with alkaline phosphatase-conjugated goat anti-mouse IgG+IgA+IgM or goat anti-human Igs (Caltag Laboratories, South San Francisco, Calif.). Detection was by measurement of absorbance at 405 nm following incubation with 1 mg/ml p-nitrophenylphosphate (Sigma) in 10% diethanolamine buffer, pH 9.8. Plasma from a normal BALB/c mouse was used as a positive control in the mouse Ig ELISA. Plasma samples from naive SCID mice or normal BALB/c mice did not have detectable levels of human Ig. Human sIL-2R was quantified using an ELISA kit (Immunotech S.A., Marseille, France) as per the manufacturer's instructions.

Five-to-seven week old mice with low plasma levels of mouse Ig (<10 μg/ml) were preconditioned with an i.p. injection of cyclophosphamide (Sigma) at 200 mg/kg. Two days later, they were injected i.p. with 25–40×10⁶ freshly-isolated human PBL suspended in 0.8 ml PBS.

Immunoconjugate Treatment

SCID mice were bled at approximately 2 weeks after human PBL transplantation. Mice with undetectable <10 pM or low plasma levels of human sIL-2R were eliminated from the study. The cut-off for exclusion of mice with detectable, but low, levels of human sIL-2R was empirically determined for each study and was generally 20 pM. The remaining mice were divided into groups and were administered vehicle or immunoconjugate as an i.v. bolus (0.2 mg/kg) daily for 5 consecutive days. Animals were sacrificed 1 day after cessation of treatment for quantitation of human T cells in tissues and human sIL-2R in plasma.

Collection of Tissues and Analysis of PBL Depletion

Blood was collected from the retro-orbital sinus into heparinized tubes. Mice were then killed by cervical dislocation and spleens were removed aseptically. Single cell suspensions of splenocytes were prepared in HBSS by pressing the spleens between the frosted ends of sterile glass microscope slides. Collected cells were washed twice with PBS. Erythrocytes were eliminated from blood and splenocyte suspensions using RBC lysing buffer. Subsequently, cells were resuspended in PBS for enumeration. Recovered cells were then assayed for Ag expression using flow cytometry.

Two to five hundred thousand cells in 100 μl of PBS/1% BSA/0.1% sodium azide were incubated on ice for 30 min. with saturating amounts of various FITC- or phycoerythrin (PE)-conjugated Abs (Becton-Dickinson, Mountain View, Calif.) Abs used for staining included: HLe-1-FITC (IgG1 anti-CD45), Leu 2-FITC (IgG1 anti-CD8), Leu 3 PE (IgG1 anti-CD4), and Leu M3-PE (IgG2a anti-CD14). Cells were then washed in cold buffer and fixed in 0.37% formaldehyde in PBS. Samples were analyzed on a FACscan (Becton-Dickinson) using log amplifiers. Regions to quantify positive cells were set based on staining of cells obtained from naive SCID mice. The absolute numbers of human Ag-positive cells recovered from SCID tissues were determined by multiplying the percent positive cells by the total number of cells recovered from each tissue sample. The total number of leukocytes in blood was calculated using a theoretical blood volume of 1.4 ml/mouse. The detection limit for accurate quantitation of human cells in SCID mouse tissues was 0.05 %. All statistical comparison between treatment groups were made using the Mann-Whitney U test. Treatment groups were determined to be significantly different from buffer control groups when the p value was <0.05. Results are presented in Table 10 below, wherein +indicates a significant difference from controls, −indicates an insignificant difference and NT means the conjugate was not tested. CD5 Plus (XOMA Corporation, Berkeley, Calif.) is mouse H65 antibody chemically linked to RTA and is a positive control. OX19 Fab-Gel$_{C247}$ is a negative control immunoconjugate. The O×19 antibody (European Collection of Animal Cell Cultures #84112012) is a mouse anti-rat CD5 antibody that does not cross react with human CD5.

TABLE 10

| Test Article | Human T Cell Depletion | |
|---|---|---|
| | Spleen | Blood |
| CD5 Plus | + | + |
| cH65 F(ab')₂ | − | − |
| cH65 Fab' | − | − |
| H65-rGEL | + | + |
| cH65 F(ab')₂-rGel | + | + |
| cH65 Fab'-rGel | + | + |
| cH65 F(ab')₂-Gel$_{C247}$ | + | NT |
| cH65 Fab'-Gel$_{C247}$ | + | + |
| heIH65 Fab'-Gel$_{C247}$ | + | NT |
| cH65 Fab'-Gel$_{C44}$ | + | + |
| OX19 Fab-Gel$_{C247}$ | − | − |

All the gelonin immunoconjugates were capable of depleting human cells in the mouse model.

EXAMPLE 10

Nine genetic constructs were assembled that each included a natural sequence gelonin gene fused to an H65 truncated heavy chain gene (Fd) or an H65 light chain gene (kappa). The H65 Fd sequence consists of the nucleotides encoding the murine H65 heavy chain variable (V), joining (J) and human IgG₁, constant (C) domain 1 regions. The DNA sequences of the V and J regions of the H65 Fd and kappa fragment genes linked to the pel B leader can be obtained from GenBank (Los Alamos National Laboratories, Los Alamos, N.M.) under Accession Nos. M90468 and M90467, respectively. Four of the gene fusions included a gelonin gene linked at the 5′ end of an H65 Fab fragment gene while the other four included an gelonin gene linked at the 3′ end of an H65 Fab fragment gene. A DNA linker encoding a peptide segment of the E. coli shiga-like toxin (SLT) (SEQ ID NO: 58), which contains two cysteine residues participating in a disulfide bond and forming a loop that includes a protease sensitive amino acid sequence) or of rabbit muscle aldolase (RMA) (SEQ ID NO: 59), which contains several potential cathepsin cleavage sites) was inserted between the gelonin gene and the antibody gene in the constructs. Alternatively, a direct fusion was made between a gelonin gene and an H65 Fab fragment gene without a peptide linker segment. Table 11 below sets out a descriptive name of each gene fusion and indicates the expression plasmid containing the gene fusion. Each plasmid also includes the Fab fragment gene (shown in parentheses in Table 11 ) with which each particular gene fusion was co-expressed.

TABLE 11

| Plasmid | Description |
| --- | --- |
| pING3754 | Gelonin::SLT::Fd (kappa) |
| pING3757 | Gelonin::SLT::kappa (Fd) |
| pING3759 | Gelonin::RMA::Fd (kappa) |
| pING3758 | Gelonin::RMA::kappa (Fd) |
| pING4406 | Fd::SLT::Gelonin (kappa) |
| pING4407 | kappa::SLT::Gelonin (Fd) |
| pING4408 | Fd::RMA::Gelonin (kappa) |
| pING4410 | kappa::RMA::Gelonin (Fd) |
| pING3334 | Gelonin::Fd (kappa) |

Fusions of Gelonin at the Carboxyl-Terminus of Antibody Genes (1) Fd::SLT::Gelonin (kappa)

A gelonin gene fusion to the 3'-end of the H65 Fd chain with the 23 amino acid SLT linker sequence was assembled in a three piece ligation from plasmids pVK1, pING3731 (ATCC 68721) and pING4000. Plasmid pVK1 contains the Fd gene linked in-frame to the SLT linker sequence; pING3731 contains the gelonin gene, and pING4000 contains the H65 kappa and Fd genes each linked to the pelB leader sequence under the control of the araB promoter as a dicistronic message.

Plasmid pVK1 was designed to link the 3'-end of a human IgG Fd$_1$ constant region in-frame to a protease-sensitive segment of the SLT bounded by two cysteine residues which form an intra-chain disulfide bond. The SLT gene segment (20 amino acids from SLT bounded by cysteine residues, plus three amino acids introduced to facilitate cloning) was assembled from two oligonucleotides, SLT Linker 1 and SLT Linker 2.

SLT Linker 1 (SEQ ID NO: 75)
5' TGTCATCATCATGCATCGCGAGTTGCCAGAAT
                 GGCATCT
GATGAGTTTCCTTCTATGTGCGCAAGTACTC 3'
SLT Linker 2 (SEQ ID NO: 76)
5' TCGAGAGTACTTGCGCACATAGAAGGAAACTCAT
                   CAGAT
GCCATTCTGGCAACTCGCGATGCATGATGAT
                   GACATGCA 3'

The two oligonucleotides were annealed and ligated into a vector containing PstI and XhoI cohesive ends, destroying the PstI site and maintaining the XhoI site. The vector, pING3185, contained an engineered Pst I site at the 3'-end of the Fd gene, and contained an XhoI site downstream of the Fd gene. The product of this ligation, pVK1, contained the H65 Fd gene (fused to the pelB leader) in frame with the SLT linker segment, and contained two restriction sites, FspI and ScaI, at the 3'-end of the SLT linker.

Plasmid pVK1 was digested with SauI and ScaI, and the 217 bp fragment containing a portion of the Fd constant domain and the entire SLT gene segment was purified by electrophoresis on an agarose gel. pING3731 was digested with SinI and XhoI and the 760 bp gelonin gene was similarly purified. Plasmid pING4000 was digested with SauI and XhoI and the vector segment containing the entire kappa gene and a portion of the Fd gene was also purified. Ligation of these three DNA fragments resulted in pING4406 containing the Fd::SLT::Gelonin (kappa) gene fusion vector.

(2) kappa::SLT::Gelonin (Fd)

A gelonin gene fusion to the 3'-end of the H65 kappa chain with the 25 amino acid SLT linker sequence (20 amino acids from SLT bounded by cysteine residues, plus 5 amino acids introduced to facilitate cloning) was assembled from the DNA segments in pING3731 (ATCC 68721) and pING3713.

Plasmid pING3713 is an Fab expression vector where the H65 Fd and kappa genes are linked in a dicistronic transcription unit containing the SLT linker segment cloned in-frame at the 3'-end of the kappa gene. The plasmid was constructed as follows. In a source plamid containing the H65 Fd and kappa genes, an EagI site was positioned at the 3-end of the kappa gene by site directed mutagenesis without altering the encoded amino acid sequence. The SLT gene segment from pVK1 was amplified with primers SLT-EagI-5' and SalI for in frame linkage to the EagI site at the 3'-end of the kappa gene.

SLT-Eag-5' (SEQ ID NO: 77)
5' TGTTCGGCCGCATGTCATCATCATGCATCG 3'
SalI (SEQ ID NO: 78)
5' AGTCATGCCCCGCGC 3'

The 140 bp PCR product was digested with EagI and XhoI, and the 75 bp fragment containing the SLT gene segment was cloned adjacent to the Fd and kappa genes in the source plåsmid to generate pING3713.

For construction of gene fusion to gelonin, pING3713 was cut with ScaI and XhoI, and the vector fragment containing the Fd gene and kappa::SLT fusion was purified. pING3731 was digested with SmaI and XhoI and the DNA fragment containing the gelonin gene was also purified. The product of the ligation of these two fragments, pING4407, contains the Fd and kappa::SLT::gelonin genes.

(3) Fd::RMA::Gelonin (kappa)

A gelonin gene fusion to the 3 '-end of the H65 Fd chain with the 21 amino acid RMA linker sequence (20 amino acids from RMA, plus 1 amino acid introduced to facilitate cloning) was assembled in a three piece ligation from plasmids pSH4, pING3731 (ATCC 68721) and pING4000.

Plasmid pSH4 contains an Fd gene linked in frame to the RMA linker sequence. The RMA gene segment was linked to the 3'-end of Fd by overlap extension PCR as follows. The 3 '-end (constant region) of the Fd gene was amplified by PCR from a source plasmid with the primers KBA-γ2 and RMAG-1. Any Fd constant region may be used because constant regions of all human $IgG_1$ antibodies are identical.

KBA-γ2 (SEQ ID NO: 79)
5' TCCCGGCTGTCCTACAGT 3'
RMAG-1 (SEQ ID NO: 80)
5' TCCAGCCTGTCCAGATGGTGTGTGAGTTTTGT
CACAA 3'

The product of this reaction was mixed with primer RMA-76, which annealed to the amplified product of the first reaction, and the mixture was amplified with primers KBA-γ2 and RMAK-2.

RMA-76 (SEQ ID NO: 81)
5' CTAACTCGAGAGTACTGTATGCATGGTTCGAGAT
GAACA
AAGATTCTGAGGCTGCAGCTCCAGCCTGTCCAGATGG 3'
RMAK-2 (SEQ ID NO: 82)
5' CTAACTCGAGAGTACTGTAT 3'

The PCR product contained a portion of the Fd constant region linked in-frame to the RMA gene segment. The product also contained a ScaI restriction site useful for in-frame fusion to a protein such as gelonin, and an XhoI site for subsequent cloning. This PCR product was cut with SauI and XhoI and ligated adjacent to the remainder of the Fd gene to generate pSH4.

For assembly of the gene fusion vector containing the Fd::RMA::Gelonin, kappa genes, pSH4 was cut with SauI and ScaI and the Fd::RMA segment was purified. Plasmid pING3731 was cut with SmaI and XhoI and the 760 bp DNA fragment containing the gelonin gene was purified, and pING4000 was cut with SauI and XhoI and the vector was purified. The product of the ligation of these fragments, pING4408, contained the Fd::RMA::Gelonin and kappa genes.

(4) kappa::RMA::Gelonin (Fd)

A gelonin gene fusion to the 3'-end of the H65 kappa chain with the 21 amino acid RMA linker sequence was assembled in a three piece ligation from plasmids pSH6, pING4408 (see the foregoing paragraph) and pING3713.

Plasmid pSH6 contains a kappa gene linked in-frame to the RMA linker sequence. The RMA gene segment was linked to the 3'-end of kappa by overlap extension PCR as follows. The 3'-end (constant region) of the kappa gene was amplified by PCR from a source plamid with the primers KBA-K2 and RMAK-1.

RMAK-1 (SEQ ID NO: 83)
5' TCCAGCCTGTCCAGATGGACACTCTCCCCTGTTGAA 3'
KBA-K2 (SEQ ID NO: 84)
5' GTACAGTGGAAGGTGGAT 3'

The product of this reaction was mixed with primer RMA-76 (SEQ ID NO: 81), which annealed to the amplified product of the first reaction, and the mixture was amplified with primers KBA-K2 and RMAK-2 (SEQ ID NO: 82). The PCR product contained a portion of the kappa constant region linked in-frame to the RMA gene segment. The product also contained a ScaI restriction site useful for in-frame fusion to a protein such as gelonin, and an XhoI site for subsequent cloning. This PCR product was cut with SstI and XhoI and ligated adjacent to the remainder to the kappa gene to generate pSH6.

For assembly of the gene fusion vector containing the kappa::RMA::Gelonin and Fd genes, pSH6 was cut with HindIII and PstI and the DNA fragment containing the kappa constant region and a portion of the RMA linker (the PstI RMA linker segment contains a PstI site) segment was purified. Plasmid pING4408 was cut with PstI and SalI and the DNA fragment containing a segment of the RMA linker, the gelonin gene and a portion of the tetracycline resistance gene in the vector segment was purified. pING3713 was cut with SalI and HindIII and the vector was purified. The product of the ligation of these three fragments, pING4410, contained the kappa::RMA::Gelonin and Fd genes.

Fusions of gelonin at the amino-terminus of antibody genes (1) Gelonin::SLT::Fd (kappa)

A gelonin gene fusion to the 5'-end of the H65 Fd chain with a 25 amino acid SLT linker sequence (20 amino acids from SLT bounded by cystine residues, plus five amino acids introduced to facilitate cloning) was assembled in a three piece ligation from plasmids pING3748, pING3217, and a PCR fragment encoding the H65 gamma variable region ($V_H$) gene segment which is the variable region of the Fd gene in pING3217. Plasmid pING3748 Contains the gelonin gene linked in-frame to the SLT linker sequence, and pING3217 contains the H65 Fd and kappa genes in a dicistronic transcription unit.

Plasmid pING3825 (see Example 2) was amplified with PCR primers gelo3'-Eag and gelo-9 to introduce an EagI restriction site at the 3'-end of the gelonin gene by PCR mutagenesis.

gelo3'-Eag (SEQ ID NO: 85)
5' CATGCGGCCGATTTAGGATCTTTATCGACGA 3'

The PCR product was cut with BclI and EagI and the 56 bp DNA fragment was purified. Plasmid pING3713 was cut with EagI and XhoI, and the 77 bp DNA fragment containing the SLT linker was purified. The 56 bp BclI to EagI fragment and the 77 bp EagI to XhoI fragment were ligated into pING3825 which had been digested with BclI and XhoI to generate pING3748 which contains the gelonin gene linked in-frame to the SLT linker sequence.

For assembly of the gene fusion vector containing the Gelonin::SLT::Fd and kappa genes, the H65 $V_H$ was amplified by PCR from pING3217 with primers H65-G1 and H65-G2, and the product was treated with T4 polymerase followed by digestion with NdeI.

H65-G1 (SEQ ID NO: 86)
5' AACATCCAGTTGGTGCAGTCTG 3'
H65-G2 (SEQ ID NO: 87)
5' GAGGAGACGGTGACCGTGGT 3'

The 176 bp fragment containing the 5'-end of the H65 heavy chain V-region was purified. Concurrently, pING3217 was digested with NdeI and XhoI, and the 1307 bp DNA fragment containing a portion of the Fd gene and all of the kappa gene was purified. The two fragments were ligated to pING3748 which had been digested with ScaI and XhoI in a three piece ligation yielding pING3754 (ATCC 69102), which contains the Gelonin::SLT::Fd and kappa genes.

(2) Gelonin::SLT::kappa (Fd)

A gelonin gene fusion to the 5'-end of the H65 kappa chain with the 25 amino acid SLT linker sequence was assembled in a three piece ligation from plasmids pING3748 (see the foregoing section), pING4000, and a PCR fragment encoding the H65 kappa variable region ($V_L$) gene segment.

For assembly of the gene fusion vector containing the Gelonin::SLT::kappa and Fd genes, an H65 $V_L$ fragment was amplified by PCR from pING3217 with primers H65-K1 and JK1-HindIII, and the product was treated with T4 polymerase followed by digestion with HindIII.

---
H65-K1 (SEQ ID NO: 88)
5' GACATCAAGATGACCCAGT 3'
JK1-HindIII (SEQ ID NO: 89)
5' GTTTGATTTCAAGCTTGGTGC 3'
---

The 306 bp fragment containing the light chain V-region was purified. Concurrently, pING4000 was digested with HindIII and XhoI, and the 1179 bp DNA fragment containing the kappa constant region and all of the Fd gene was purified. The two fragments were ligated to pING3748 which had been digested with ScaI and XhoI in a three piece ligation yielding pING3757, which contains the Gelonin::SLT::kappa and Fd genes.

(3) Gelonin::RMA::Fd (kappa)

A gelonin gene fusion to the 5'-end of the H65 Fd chain with the 24 amino acid RMA linker sequence (20 amino acids from RMA, plus 4 amino acids introduced to facilitate cloning) was assembled in a three piece ligation from plasmids pING3755, pING3217, and a PCR fragment encoding the H65 $V_H$ gene segment. Plasmid pING3755 contains the gelonin gene linked in-frame to the RMA linker sequence, and pING3217 contains the H65 Fd and kappa genes in a dicistronic transcription unit.

Plasmid pING3755 was assembled to contain the gelonin gene linked to the RMA linker gene segment. The RMA linker gene segment was amplified by PCR from pSH4 with primers RMA-EagI and HINDIII-2.

---
RMA-EagI (SEQ ID NO: 90)
5' ACTTCGGCCGCACCATCTGGACAGGCTGGAG 3'
HINDIII-2 (SEQ ID NO: 91)
5' CGTTAGCAATTTAACTGTGAT 3'
---

The 198 bp PCR product was cut with EagI and HindIII, and the resulting 153 bp DNA fragment was purified. This RMA gene segment was cloned adjacent to gelonin using an PstI to EagI fragment from pING3748 and the PstI to HindIII vector fragment from pING3825. The product of this three piece ligation was pING3755.

For assembly of the gene fusion vector containing the Gelonin::RMA::Fd, kappa genes, the H65 $V_H$ was amplified by PCR from pING3217 with primers H65-G1 (SEQ ID NO: 86) and H65-G2 (SEQ ID NO: 87), and the product was treated with T4 polymerase followed by digestion with NdeI. The 186 bp fragment containing the 5'-end of the heavy chain V-region was purified. Concurrently, pING3217 was digested with NdeI and XhoI, and the 1307 bp DNA fragment containing a portion of the Fd gene and all of the kappa gene was purified. These two fragments were ligated to pING3755 which had been digested with ScaI and XhoI in a three piece ligation yielding pING3759 (ATCC 69104), which contains the Gelonin::RMA::Fd and kappa genes.

(4) Gelonin::RMA::kappa (Fd)

A gelonin gene fusion to the 5'-end of the H65 kappa chain with the 24 amino acid RMA linker sequence was assembled in a three piece ligation from plasmids pING3755, pING4000, and a PCR fragment encoding the H65 $V_L$ gene segment.

For assembly of the gene fusion vector containing the Gelonin::RMA::kappa and Fd genes, an H65 $V_L$ segment was amplified by PCR from pING3217 with primers H65K-1 (SEQ ID NO: 88) and JK1-HindIII (SEQ ID NO: 89), and the product was treated with T4 polymerase followed by digestion with HindIII. The 306 bp fragment containing the 5'-end of the light chain V-region was purified. Concurrently, pING4000 was digested with HindIII and XhoI, and the 1179 bp DNA fragment containing the kappa constant region and all of the Fd gene was purified. These two fragments were ligated to pING3755 which had been digested with ScaI and XhoI in a three piece ligation yielding pING3758 (ATCC 69103), which contains the Gelonin::RMA::kappa and Fd genes.

(5) Gelonin::Fd (Kappa)

A direct gelonin gene fusion was constructed from pING3754. pING3754 was digested with BglII and XhoI and the vector segment was purified. Concurrently, pING3754 was digested with EagI, treated with T4 polymerase, cut with BglII, and the gelonin gene segment was purified. pING3754 was also cut with FspI and XhoI, and the Fd and kappa gene segment was purified. These fragments were assembled in a three-piece ligation to generate pING3334, which contains a direct gene fusion of gelonin to Fd in association with a kappa gene.

EXAMPLE 11

Each of the eight gelonin gene fusions whose construction is described in Example 10 was co-expressed with its pair H65 Fab gene in arabinose-induced *E. coli* strain E104.

Expression products of the gene fusions were detected in the supernatant of induced cultures by ELISA. Typically, a plate was coated with antibody recognizing gelonin. Culture supernatant was applied and bound Fab was detected with antibody recognizing human kappa coupled to horseradish peroxidase. H65 Fab fragment chemically conjugated to gelonin was used a standard. Alternative ELISA protocols involving coating a plate with antibody recognizing either the kappa or Fd or involving a detection step with anti-human Fd rather that anti-human kappa yielded similar results. Only properly assembled fusion protein containing gelonin, kappa and Fd was detected by this assay. Unassociated chains were not detected.

The fusion protein produced from induced cultures containing expression vectors pING4406, 4407, 4408, and 4410 in *E. coli* E104 accumulated at about 20–50 ng/ml. The fusion proteins expressed upon induction of pING3754, 3334, 3758 and 3759 (but not pING3757) were expressed at much higher levels, at about 100 to 500 ng/ml. A fusion protein of about 70,000 Kd was detected in the concentrated *E. coli* culture supernatant by immunostaining of Western blots with either anti-human kappa or anti-gelonin antibodies.

The Gelonin::SLT::Fd (kappa) fusion protein from pING3754 (ATCC 69102) was purified from induced 10 L fermentation broth. The 10 L fermentation broth was concentrated and buffer exchanged into 10mM phosphate buffer at pH 7.0, using an S10Y10 cartridge (Amicon) and a DC10 concentrator. The supernatant was purified by passing the concentrated supernatant through a DE52 column (20×5 cm) equilibrated with 10 mM sodium phosphate buffer at pH 7.0. The flow-through was then further purified and concentrated by column chromatography on CM52 (5×10 cm) in 10 mM phosphate buffer. A 0–0.2 M linear gradient of NaCl was used to the elute the fusion protein, and fractions containing the fusion protein were pooled and loaded onto a Protein G column (1 ml). The fusion protein was eluted from protein G with 0.2 M glycine. The Gelonin::RMA::Fd (kappa) and Gelonin::RMA::kappa (Fd) fusions proteins were purified from fermentation broths by similar methods except that the CM52 column step was eliminated, and the DE52 column was equilabrated with 100 mM sodium phosphate buffer at pH 7.0. The fusion proteins were not purified to homogeneity.

Each of the three purified fusion proteins was then assayed for activity in the RLA assay and for cytotoxicity against the T-cell line HSB2. (T cells express the CD5 antigen which is recognized by H65 antibody.) The RLA assay was performed as described in Example 4 and results of the assay are presented below in Table 12.

TABLE 12

| Fusion Protein | IC50 (pM) |
| --- | --- |
| rGelonin | 11 |
| Gelonin::SLT::Fd (kappa) | 19 |
| Gelonin::RMA::Fd (kappa) | 28 |
| Gelonin::RMA::kappa (Fd) | 10 |

In whole cell cytotoxicity assays performed as described in Example 6, the fusion protein was active and killed two T cell lines, HSB2 and CEM, with respective $IC_{50}$s 2-fold (HSB2) or 10-fold (CEM) lower than that of the gelonin chemically linked to H65. See Table 13 below for results wherein $IC_{50}$ values were adjusted relative to the amount of fusion protein in each sample.

TABLE 13

| | $IC_{50}$ (pMT) | |
| --- | --- | --- |
| Fusion Protein | HSB2 Cells | CEM Cells |
| he3Fab-Gel$_{C44}$ | 165 | 173 |
| Gelonin:SLT::Fd (kappa) | 180 | 1007 |
| Gelonin::RMA::Fd (kappa) | 150 | nt |

The fusion protein showed similar activity on peripheral blood mononuclear cells (dam not shown).

EXAMPLE 12

The natural sequence gelonin gene was also fused to a single chain form of the human engineered he3 H65 variable region. The gelonin gene was positioned at the N-terminus of the fusion gene and the SLT or RMA linker peptide was positioned between the gelonin and antibody domains to allow intracellular processing of the fusion protein with subsequent cytosolic release of gelonin.

A single chain antibody (scAb) form of the he3 H65 variable domain was assembled from previously constructed genes. This scab segment consisted of the entire V and J region of the one chain (heavy or light) linked to the entire V and J segment of the other chain (heavy or light) via a 15 amino acid flexible peptide: [(Gly)$_4$Ser]$_3$. This peptide is identical to that described in Huston et al., Proc. Natl. Acad. Sci. USA, 85, 5879–5883 (1988); Glockshuber et al., Biochemistry, 29, 1362–1367 (1990); and Cheadle et al., Molecular Immunol., 29, 21–30 (1992). The scAb was assembled in two orientations: V-J$_{kappa}$::[(Gly)$_4$Ser]$_3$::V-J$_{Gamma}$ (SEQ ID NO: 92) and V-J$_{Gamma}$::[(Gly)$_4$Ser]$_3$::V-J$_{kappa}$ (SEQ ID NO: 93). Each scab segment was assembled and subsequently fused to gelonin.

For assembly of the scAb segment V-J$_{kappa}$::[(Gly)$_4$Ser]$_3$::V-J$_{Gamma}$, primers HUK-7 and SCFV-1 were used to amplify a 352 bp DNA fragment containing the he3 V/J kappa sequences from pING4627 by PCR in a reaction containing 10 mM KCl, 20 mM TRIS pH 8.8, 10 mM (NH4)$_2$SO$_2$, 2 mM MgSO$_4$, 0.1% Triton X-100., 100 ng/ml BSA, 200 uM of each dNTP, and 2 Units of Vent polymerase (New England Biolabs, Beverley, Mass.) in a total volume of 100 μl.

SCFV-1 (SEQ ID NO: 94)
5' CGGACCCACCTCCACCAGATCCACCGC
CACCTTTCATCTCAAGCTTGGTGC 3'
HUK-7 (SEQ ID NO: 95)
5' GACATCCAGATGACTCAGT 3'

Concurrently, primers SCFV-2 and SCFV-3 were used to amplify a he3 heavy chain V/J gamma segment from pING4623, generating a 400 bp fragment.

SCFV-2 (SEQ ID NO: 96)
5' GGTGGAGGTGGGTCCGGAGGTGGAGGATCTGA
GATCCAGTTGGTGCAGT 3'
SCFV-3 (SEQ ID NO: 97)
5' TGTACTCGAGCCCATCATGAGGAGACGGTGACCGT 3'

The products from these reactions were mixed and amplified with the outside primers HUK-7 and SCFV-3. The product of this reaction was treated with T4 polymerase and then cut with XhoI. The resulting 728 bp fragment was then purified by electrophoresis on an agarose gel. This fragment was ligated into the vectors pING3755 and pING3748 (see Example 10), each digested with ScaI and XhoI. The resulting vectors pING4637 and pING4412 contain the Gelonin::RMA::scab V-J$_{kappa}$::[(Gly)$_4$Ser]$_3$::V-J$_{Gamma}$ and Gelonin::SLT::scAb V-J$_{kappa}$::[(Gly)$_4$Ser]$_3$::V-J$_{Gamma}$ fusion genes, respectively.

Similarly, the scAb V-J$_{Gamma}$::[(Gly)$_4$Ser]$_3$::V-J$_{kappa}$ was assembled by amplification of pING4627 with primers SCFV-5 and SCFV-6 generating a 367 bp fragment containing he3 V/J kappa sequences, SCFV-5 (SEQ ID NO: 98)
5' GGTGGAGGTGGGTCCGGAGGTGGAGGATCT 3'
SCFV-6 (SEQ ID NO: 99)
5' TGTACTCGAGCCCATCATTTCATCTCAAGCTTGGTGC 3' and pING4623 with primers H65-G3 and SCFV-4 generating a 385 bp fragment containing he3 gamma V/J sequences by PCR with Vent polymerase.

H65-G3 (SEQ ID NO: 100)
5' GAGATCCAGTTGGTGCAGTCTG 3'
SCFV-4 (SEQ ID NO: 101)
5' CGGACCCACCTCCACCAGATCC
ACCGCCACCTGAGGAGACGGTGACCGT 3'

The products from these reactions were mixed and amplified with H65-G3 and SCFV-6. The 737 bp product was treated with T4 polymerase and cut with XhoI. Ligation into pING3755 and pING3748 (digested with ScaI and XhoI) resulted in assembly of the Gelonin::-RMA::scAb V-J$_{Gamma}$::[(Gly)$_4$Ser]$_3$::V-J$_{kappa}$ gene fusion in pING4638 and Gelonin::SLT::scAb V-J$_{Gamma}$::[(Gly)$_4$Ser]$_3$::V-J$_{kappa}$ gene fusion in pING4639, respectively.

The vectors pING4637, pING4412, pING4638 and pING4639 were each transformed into E. coli strain E104 and induced with arabinose. Protein products of the predicted molecular weight were identified by Western blot with gelonin-specific antibodies.

Gelonin::scAb fusions without a cleavable linker can be constructed by deletion of the SLT linker in pING4412 using the restriction enzymes EagI and FspI. Digestion at these sites and religation of the plasmid results in an in-frame deletion of the SLT sequence.

EXAMPLE 13

BRIP possesses characteristics which make it an attractive candidate for a component of immunotoxins. BRIP is a naturally unglycosylated protein that may have reduced uptake in the liver and enhanced circulatory residence time in vivo. Additionally, BRIP is less toxic and less immunogenic in animals than the A-chain of ricin. Cloning of the BRIP gene and expression of recombinant BRIP in an E. coli expression system obviates the need to purify native BRIP directly from barley, and enables the development of analogs of BRIP which may be conjugated with an available cysteine residue for conjugation to antibodies.

Purification of BRIP and Generation of Polyclonal Antibodies to BRIP

Native BRIP was purified from pearled barley flour. Four kilograms of flour was extracted with 16 liters of extraction buffer (10 mM NaPO4, 25 mM NaCl, pH 7.2) for 20 hours at 4° C. The sediment was removed by centrifugation, and 200 ml of packed S-Sepharose (Pharmacia, Piscataway, N.J.) was added to absorb BRIP. After mixing for 20 hours at 4° C., the resin was allowed to settle out, rinsed several times with extraction buffer and then packed into a 2.6×40 cm column. Once packed, the column was washed with extraction buffer (150 ml/h) until the absorbance of the effluent approached zero. BRIP was then eluted with a linear gradient of 0.025 to 0.3 M NaCl in extraction buffer and 5 ml fractions were collected. BRIP-containing peaks (identified by Western analysis of column fractions) were pooled, concentrated to about 20 ml, and then chromatographed on a 2.6×100 cm Sephacryl S-200HR (Pharmacia) column equilibrated in 10 mM NaPO4, 125 mM NaCl, pH 7.4 (10 ml/hr). BRIP-containing peaks were pooled again, concentrated, and stored at −70° C.

The resulting purified BRIP protein had a molecular weight of about 30,000 Daltons, based upon the mobility of Coomassie-stained protein bands following SDS-PAGE. The amino acid composition was consistent with that published by Asano et al., *Carlsberg Res. Comm.*, 49, 619–626 (1984).

Rabbits were immunized with purified BRIP to generate polyclonal antisera.

Cloning of the BRIP Gene

A cDNA expression library prepared from germinating barley seeds in the phage λ expression vector λZAPII was purchased from Stratagene, La Jolla, Calif. Approximately 700,000 phage plaques were screened with anti-BRIP polyclonal antisera and 6 immunoreactive plaques were identified. One plaque was chosen, and the cDNA contained therein was excised from λZAPII with EcoRI and subcloned into pUC18 generating the vector pBS1. The cDNA insert was sequenced with Sequenase (United States Biochemical, Cleveland, Ohio). The DNA sequence of the native BRIP gene is set out in SEQ ID NO: 12. To confirm that cDNA encoded the native BRIP gene, the cDNA was expressed in the E. coli plasmid pKK233-2 (Pharmacia). BRIP protein was detected in IPTG-induced cells transformed with the plasmid by Western analysis with above-described rabbit anti-BRIP antisera.

Construction of an E. coli Expression Vector Containing the BRIP Gene

Barley cDNA containing the BRIP gene was linked to a pelB leader sequence and placed under control of an arab promoter in a bacterial secretion vector.

An intermediate vector containing the BRIP gene linked to the pelB leader sequence was generated. Plasmid pBS1 was cut with NcoI, treated with Mung Bean Nuclease, cut with BamHI and the 760 bp fragment corresponding to amino acids 1–256 of BRIP was purified from an agarose gel. Concurrently, a unique XhoI site was introduced downstream of the 3'-end of the BRIP gene in pBS1 by PCR amplification with a pUC18 vector primer (identical to the Reverse® primer sold by NEB or BRL but synthesized on a Cyclone Model 8400 DNA synthesizer) and the specific primer BRIP 3'Xho. The sequence of each of the primers is set out below.

Reverse (SEQ ID NO: 45)
5' AACAGCTATGACCATG 3'
BRIP 3'Xho (SEQ ID NO: 46)
5' TGAACTCGAGGAAAACTACCTATTTCCCAC 3'

Primer BRIP 3'Xho includes a portion corresponding to the last 8 bp of the BRIP gene, the termination codon and several base pairs downstream of the BRIP gene, and an additional portion that introduces a XhoI site in the resulting PCR fragment. The PCR reaction product was digested with BamHI and XhoI, and an 87 bp fragment containing the 3'-end of the BRIP gene was purified on a 5% acrylamide gel. The 760 and 87 bp purified BRIP fragments were ligated in the vector pING 1500 adjacent to the pelB leader sequence. pING1500 had previously been cut with SstI, treated with T4 polymerase, cut with XhoI, and purified. The DNA sequence at the junction of the pelB leader and the 5'-end of the BRIP gene was verified by DNA sequence analysis. This vector was denoted pING3321-1.

The final expression vector was assembled by placing the BRIP gene under the control of the inducible araB promoter. Plasmid pING3321-1 was cut with PstI and XhoI, and the BRIP gene linked to the pelB leader was purified from an agarose gel. The expression vector pING3217, containing the arab promoter, was cut with PstI and XhoI and ligated to the BRIP gene. The expression vector was denoted pING3322.

Arabinose induction of E. coli cells containing the plasmid pING3322 in a fermenter resulted in the production of about 100 mg per liter of recombinant BRIP. E. coli-produced BRIP displays properties identical to BRIP purified directly from barley seeds.

Construction of BRIP Analogs With a Free Cysteine Residue

The BRIP protein contains no cysteine residues, and therefore contains no residues directly available which may form a disulfide linkage to antibodies or other proteins. Analogs of recombinant BRIP were generated which contain a free cysteine residue near the C-terminus of the protein. Three residues of the BRIP protein were targets for amino acid substitutions. Comparison of the amino acid sequence of BRIP to the known tertiary structure of the ricin A-chain (see FIG. 2) suggested that the three positions would be available near the surface of the molecule. The three BRIP analogs include cysteines substituted in place of serine$_{277}$, alanine$_{270}$, and leucine$_{256}$ of the native protein, and were designated BRIP$_{C277}$, BRIP$_{C270}$ and BRIP$_{C256}$, respectively.

(1) A plasmid vector capable of expressing the BRIP$_{C277}$ analog was constructed by replacing the 3'-end of the BRIP gene with a DNA segment conferring the amino acid change. The EcoRI fragment containing the BRIP gene from pBS1 was subcloned into M13mp18, and single-stranded DNA (anti-sense strand) was amplified by PCR with primers OBM2 (corresponding nucleotides −11 to +8 of the BRIP gene) and OMB4 (corresponding to amino acids 264–280 of BRIP and the termination codon of BRIP, and incorporating the substitution of a cysteine codon for the native codon for serine$_{277}$ of native BRIP). The sequences of primers OBM2 and OMB4, wherein the underlined nucleotides encode the substituted cysteine, are set out below.

| OBM2 (SEQ ID NO: 47) |
|---|
| 5' GCATTACATCCATGGCGGC 3' |
| OMB4 (SEQ ID NO: 48) |
| 5' GATATCTCGAGTTAACTATTTCCCACC<u>ACA</u>CG |
| CATGGAACAGCTCCAGCGCCTTGGCCACCGTC 3' |

A fragment containing a BRIP gene in which the codon for the amino acid at position 277 was changed to a cysteine codon was amplified. The fragment was cloned into the SmaI site of pUC19 (BRL) and the plasmid generated was denoted pMB22. pMB22 was digested with EcoRI and an EcoRI-XhoI linker (Clonetech, Palo Alto, Calif.) was ligated into the vector. Subsequent digestion with XhoI and religation generated vector pINGMB2X. A BamHI to XhoI fragment encoding the 3'-end of BRIP with the altered amino acid was excised from pMB2X and the fragment was purified on a 5% acrylamide gel. This fragment along with an EcoRI to BamHI fragment containing the pelB leader sequence and sequences encoding the first 256 amino acids of BRIP were substituted in a three piece ligation into pING3322 cut with EcoRI and XhoI. The resulting vector containing the BRIP$_{C277}$ analog was designated pING3803 (ATCC Accession No. 68722).

(2) A BRIP analog with a free cysteine at position 256 was constructed using PCR to introduce the amino acid substitution. A portion of the expression plasmid pING3322 was amplified with primers BRIP-256 and HINDIII-2. The sequence of each primer is set out below.

| BRIP-256 (SEQ ID NO: 49) |
|---|
| 5' <u>TGT</u>CTGTTCGTGGAGGTGCCG 3' |
| HINDIII-2 (SEQ ID NO: 50) |
| 5' CGTTAGCAATTTAACTGTGAT 3' |

Nucleotides 4–21 of primer BRIP-256 encode amino acids 256–262 of BRIP while the underlined nucleotides specify the cysteine to be substituted for the leucine at the corresponding position of the native BRIP protein. Primer HINDIII-2 corresponds to a portion of the plasmid. The PCR product, which encodes the carboxyl terminal portion of the BRIP analog, was treated with T4 polymerase, cut with XhoI, and the resulting fragment was purified on a 5% acrylamide gel. Concurrently, plasmid pING3322 was cut with BamHI, treated with T4 polymerase, cut with EcoRI, and the fragment containing the pelB leader sequence and sequences encoding the first 256 amino acids of BRIP was purified. The two fragments were then assembled back into pING3322 to generate the gene encoding the analog BRIP$_{C256}$. This plasmid is denoted pING3801.

(3) A BRIP analog with a cysteine at position 270 was also generated using PCR. A portion of the expression plasmid pING3322 was amplified with primers BRIP-270 and the HINDIII-2 primer (SEQ ID NO: 50). The sequence of primer BRIP-270 is set out below.

| BRIP-270 (SEQ ID NO: 51) |
|---|
| 5' CCAAGTGTCTGGAGCT<u>GTT</u>CCATGCGA 3' |

Primer BRIP-270 corresponds to amino acids 268–276 of BRIP with the exception of residue 270. The codon of the primer corresponding to position 270 specifies a cysteine instead of the alanine present in the corresponding position in native BRIP. The PCR product was treated with T4 polymerase, cut with XhoI, and the 51 bp fragment, which encodes the carboxyl terminal portion of the analog, was purified on a 5% acrylamide gel. The fragment (corresponding to amino acids 268–276 of BRIP$_{C270}$) was cloned in a three piece ligation along with the internal 151 bp BRIP restriction fragment from SstII to MscI (corresponding to BRIP amino acids 217–267) from plasmid pING3322, and restriction fragment from SstII to XhoI from pING3322 containing the remainder of the BRIP gene. The plasmid generated contains the gene encoding the BRIP$_{C270}$ analog and is designated pING3802.

Purification of Recombinant BRIP and the BRIP Analogs

Recombinant BRIP (rBRIP) and the BRIP analogs with free cysteine residues were purified essentially as described for native BRIP except they were prepared from concentrated fermentation broths. For rBRIP, concentrated broth from a 10 liter fermentation batch was exchanged into 10 mM Tris, 20 mM NaCl pH 7.5, loaded onto a Sephacryl S-200 column, and eluted with a 20 to 500 mM NaCl linear gradient. Pooled rBRIP was further purified on a Blue Toyopearl ® column (TosoHaas) loaded in 20 mM NaCl and eluted in a 20 to 500 mM NaCl gradient in 10mM Tris, pH 7.5. For BRIP analogs, concentrated fermentation broths were loaded onto a CM52 column (Whatman) in 10 mM phosphate buffer, pH 7.5, and eluted with a 0 to 0.3M NaCl linear gradient. Further purification was by chromatography on a Blue Toyopearl ® column.

Reticulocyte Lysate Assay

The ability of the rBRIP and the BRIP analogs to inhibit protein synthesis in vitro was tested by reticulocyte lysate assay as described in Example 1. Serial log dilutions of standard toxin (RTA 30), native BRIP, rBRIP and BRIP analogs were tested over a range of 1 μg/ml to 1 pg/ml. By comparison with an uninhibited sample, the picomolar concentration of toxin (pM) which corresponds to 50% inhibition of protein synthesis ($IC_{50}$) was calculated. The results of the assays are presented below in Table 14.

TABLE 14

| Toxin | $IC_{50}$ (pM) |
|---|---|
| RTA 30 | 3.1 |
| Native BRIP | 15 |
| rBRIP | 18 |
| $BRIP_{C256}$ | 23 |
| $BRIP_{C270}$ | 20 |
| $BRIP_{C277}$ | 24 |

The RLA results indicate that the BRIP analogs exhibit ribosome-inactivating activity comparable to that of the recombinant and native BRIP toxin. All the analogs retained the natural ability of native BRIP to inhibit protein synthesis, suggesting that amino acid substitution at these positions does not affect protein folding and activity.

Construction of BRIP Immunoconjugates

Immunoconjugates of native BRIP with 4A2 (described in Morishima et al., *J. Immunol.*, 129, 1091 (1982) and H65 antibody (obtained from hybridoma ATCC HB9286) which recognize the T-cell determinants CD7 and CD5, respectively, were constructed. Immunoconjugates of ricin A-chains (RTAs) with 4A2 and H65 antibody were constructed as controls. The H65 antibody and ricin A-chains as well as the RTA immunoconjugates were prepared and purified according to methods described in U.S. patent application Ser. No. 07/306,433 supra and in International Publication No. WO 89/06968.

To prepare immunoconjugates of native BRIP, both the antibody (4A2 or H65) and native BRIP were chemically modified with the hindered linker 5-methyl-2-iminothiolane (M2IT) at lysine residues to introduce a reactive sulfhydryl group as described in Goff et al., *Bioconjugate Chem.*, 1, 381–386 (1990). BRIP (3 mg/ml) was first incubated with 0.5 mM M2IT and 1 mM DTNB in 25 mM triethanolamine, 150 mM NaCl, pH 8.0, for 3 hours at 25° C. The derivitized BRIP-(M2IT)-S-S-TNB was then desalted on a column of Sephadex GF-05LS and the number of thiol groups introduced was quantitated by the addition of 0.1 mM DTT. On average, each BRIP molecule contained 0.7 SH/mol.

4A2 or H65 antibody (4 mg/ml) in triethanolamine buffer was similarly incubated with M2IT (0.3 mM) and DTNB (1 mM) for 3 hours at 25° C. Antibody-(M2IT)-S-S-TNB was then desalted and the TNB:antibody ratio was determined. To prepare the conjugate, the BRIP-(M2IT)-S-S-TNB was first reduced to BRIP-(M2IT)-SH by treatment with 0.5 mM DTT for 1 hour at 25° C., desalted by gel filtration of Sephadex ® GF-05LS to remove the reducing agent, and then mixed with antibody-(M2IT)-S-S-TNB.

Following a 3 hour incubation at 25° C., and an additional 18 hours at 4° C., the conjugate was purified by sequential chromatography on AcA44 (IBF) and Blue Toyopearl ®. Samples of the final product were run on 5% non-reducing SDS PAGE, Coomassie stained, and scanned with a Shimadzu laser densitometer to quantitate the number of toxins per antibody.

The BRIP analogs containing a free cysteine were also conjugated to 4A2 and H65 antibodies. The analogs were treated with 50 mM DTT either for 2 hours at 25° C. or for 18 hours at 4° C. to expose the reactive sulfhydryl group of the cysteine and desalted. The presence of a free sulfhydryl was verified by reaction with DTNB [Ellman et al., *Arch. Biochem. Biophys*, 82, 70–77 (1959)]. 4A2 or H65 antibody derivatized as described above with M2IT was incubated with the reduced BRIP analogs at a ratio of 1:5 at room temperature for 3 hours and then overnight at 4° C. Immunoconjugates H65-$BRIP_{C256}$, 4A2-$BRIP_{C256}$, H65-$BRIP_{C277}$ were prepared in 25 mM triethanolamine, 150 mM NaCl pH 8, while immunoconjugates H65-$BRIP_{270}$, 4A2-$BRIP_{C270}$ and 4A2-$BRIP_{C277}$ were prepared in 0.1 M sodium phosphate, 150 mM NaCl pH 7.5. Following conjugation, 10 μM mercaptoethylamine was added for 15 minutes at 25° C. to quenched any unreacted m2IT linkers on the antibody. The quenched reaction solution was promptly loaded onto a gel filtration column (AcA44) to remove unconjugated ribosome-inactivating protein. Purification was completed using soft gel affinity chromatography on Blue Toyopearl ® resin using a method similar to Knowles et al., *Analyt. Biochem.*, 160, 440 (1987). Samples of the final product were run on 5% non-reduced SDS PAGE, Coomassie stained, and scanned with a Shimadzu laser densitometer to quantitate the number of toxins per antibody. The conjugation efficiency was substantially greater for $BRIP_{C277}$ (78%) than for either of the other two analogs, $BRIP_{C270}$ and $BRIP_{C256}$ (each Of these was about 10%). Additionally, the $BRIP_{C277}$ product was a polyconjugate, i.e., several BRIP molecules conjugated to a single antibody, in contrast to the $BRIP_{C270}$ and $BRIP_{C256}$ products which were monoconjugates.

Whole Cell Kill Assay

Immunoconjugates of native BRIP and of the BRIP analogs were tested for the ability to inhibit protein synthesis in HSB2 cells by the whole cell kill assay described in Example 1. Standard immunoconjugates H65-RTA (H65 derivatized with SPDP linked to RTA) and 4MRTA (4A2 antibody derivatized with M2IT linked to RTA) and BRIP immunoconjugate samples were diluted with RPMI without leucine at half-log concentrations ranging from 2000 to 0.632 ng/ml. All dilutions were added in triplicate to microtiter plates containing $1\times10^5$ HSB2 cells. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar toxin concentration (pM T) of immunoconjugate which resulted in a 50% inhibition of protein synthesis ($IC_{50}$) was calculated. The assay results are presented below in Table 15.

TABLE 15

| Conjugate | IC$_{50}$ (pM T) |
|---|---|
| 4A2-BRIP | 122.45 |
| 4A2-BRIP$_{C270}$ | 46.3 |
| 4A2-BRIP$_{C277}$ | 57.5 |
| 4A2-BRIP$_{C256}$ | 1116 |
| H65-BRIP | >5000 |
| H65-BRIP$_{C277}$ | 1176 |

The BRIP analog conjugates were less potent than the ricin conjugate control (dam not shown). The immunotoxins containing antibody 4A2 and either the BRIP$_{C270}$ or the BRIP$_{C277}$ analog exhibited comparable to increased specific cytotoxicity toward target cells as compared to immunotoxin containing native BRIP. While 4A2-BRIP$_{C256}$ is less active than 4A2-BRIP, 4A2-BRIP$_{C270}$ and 4A2-BRIP$_{C277}$ are between 3 and 4 times more active. Similarly, the immunoconjugate of H65 to BRIP$_{C277}$ shows greater toxicity toward target cells than the immunoconjugate of H65 to native BRIP. Thus, linkage of antibody to BRIP derivatives which have an available cysteine residue in an appropriate location results in immunotoxins with enhanced specific toxicity toward target cells relative to conjugates with native BRIP.

Disulfide Bond Stability Assay

Immunoconjugates prepared with native BRIP and the BRIP analogs were examined by the disulfide bond stability assay described in Example 1. Briefly, conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparisons with the amount of RIP released by high concentrations of 2-mercaptoethanol (to determine 100% release), the concentration of glutathione required to release 50% of the RIP (the RC$_{50}$) was calculated. As shown below in Table 16, the conjugates prepared with BRIP$_{C270}$ or BRIP$_{C277}$ were significantly more stable than either the RTA conjugates or those prepared with native BRIP.

TABLE 16

| Conjugate | RC$_{50}$ (mM) |
|---|---|
| H65-RTA | 7.0 |
| H65-BRIP | 2.8 |
| H65-BRIPC277 | 196.0 |
| 4A2-RTA | 4.4 |
| 4A2-BRIP | 3.3 |
| 4A2-BRIP$_{C270}$ | 53.0 |
| 4A2-BRIP$_{C277}$ | 187.0 |

These unexpected results suggest that conjugates prepared with Type I RIP analogs according to the present invention may have enhanced stability and efficacy in vivo.

EXAMPLE 14

Plants of the genus Momordica produce a number of related proteins known as momordins or momorcharins which are Type I RIPs. The gene encoding momordin II was cloned from *Momordica balsamina* seeds.

Preparation of *M. balsamina* RNA

Total RNA was prepared from 4 g of *M. balsamina* seeds as described in Ausubel et al., supra. PolyA containing RNA was prepared from 1 mg of total RNA by chromatography on oligo-(dT)-cellulose. 40 mg of oligo-(dT)-cellulose Type 7 (Pharmacia) was added to 0.1 N NaOH and poured into a disposable column (Biorad). The column was washed with water until the eluate was pH 5.5, and then was washed with 1X loading buffer (50 mM NaCitrate, 0.5M NaCl, 1 mM EDTA, 0.1% SDS, pH 7.0) until the eluate was pH 7.0. 1 mg of total RNA was suspended in 300 μl of water, heated to 65° C. for 5 minutes, and 300 μl of 2X loading buffer was added (100 mM Na Citrate, 1M NaCl, 2 mM EDTA, and 0.2% SDS). The RNA was loaded onto the column, and the flow through was reheated to 65° C., cooled to room temperature, and reloaded onto the column. Column-bound mRNA was washed 5 times with 0.5 ml of 1X loading buffer, and two times with 0.5 ml of 0.05M NaCitrate, 0.1 M NaCl, 1 mM EDTA, 0.1% SDS. PolyA-containing RNA was eluted two times from the column with 0.5 ml of 25 mM NaCitrate, 1 mM EDTA, and 0.05% SDS.

Library Preparation

A cDNA library from the polyA-containing *M. balsamina* RNA was prepared in a bacterial expression plasmid with the SuperScript Plasmid System (BRL, Gaithersburg, Md.). The cDNA was synthesized from 2 μg of poly A-containing RNA, size fractionated, digested with NotI, and ligated into the expression vector pSPORT as recommended by the manufacturer of the vector, BRL.

Cloning of the Momordin II Gene

A DNA fragment encoding the first 27 amino acids of momordin II was amplified from *M. balsamina* cDNA by PCR. First strand cDNA was prepared from 100 ng of polyA containing RNA with an RNA-PCR Kit (Perkin Elmer Cetus). Two partially degenerate primers were synthesized based on the amino acid sequence of the first 27 amino acids of momordin II described in Li et al., *Experientia*, 36, 524–527 (1980). Because the amino acid sequence of amino acids 1–27 of momordin II is 52% homologous to amino acids 1–17 of momordin I [Ho et al., *BBA*, 1088, 311–314 (1991)], some codon assignments in the degenerate primers were based on homology to the corresponding amino acid as well as codon preference in the momordin I gene. The sequences of primers momo-3 and momo-4 are set out below using IUPAC nucleotide symbols.

momo-3 (SEQ ID NO: 52)
5' GATGTTAAYTTYGAYTTGTCNACDGCTAC 3'
momo-4 (SEQ ID NO: 53)
5' ATTGGNAGDGTAGCCCTRAARTCYTCDAT 3'

The resulting 81 bp PCR product was purified on a 5% acrylamide gel and cloned into the SmaI site of pUC18. Three candidate clones were sequenced, and one clone, pMO110, was identified which encoded the N-terminal 27 amino acids of momordin II.

A hybridization probe was designed for screening of the momordin II cDNA library based on the sequence of the pMO110 momordin II DNA fragment. The sequence of the primer momo-5 is shown below.

momo-5 (SEQ ID NO: 54)
5' GCCACTGCAAAAACCTACACAAAATTTATTGA 3'

Primer momo-5 corresponds to amino acids 9–18 of mature momordin II. The underlined nucleotides of the primer were expected to match the DNA sequence of the momordin II gene exactly. Since this sequence is highly A/T-rich and may hybridize to the momordin II gene weakly, the additional adjacent nucleotides were included in the primer. Bases 3 and 30 (overlined) were in the "wobble" position (i.e., the third nucleotide in a codon) of amino acids 9 (alanine) and 18 (isoleucine), respectively, of momordin II and may not be identical to the nucleotide bases in the native gene.

A 90,000 member cDNA library in pSPORT was screened with $^{32}$P-kinased momo-5, and eight potential candidate clones were identified. One clone, pING3619, was sequenced and contains an open reading frame corresponding in part to the expected N-terminal 27 residues of Momordin II. The complete momordin gene contains 286 amino acids, the first 23 of which are a presumed leader signal (mature momordin II is 263 residues). The DNA sequence of the momordin II gene is set out in SEQ ID NO: 13.

Construction of an Expression Vector Containing the Momordin II Gene

A bacterial expression vector for the momordin II gene was constructed. Two PCR primers were synthesized, one (momo-9) which primes from the +1 residue of the mature momordin II amino acid sequence, and one at the C-terminus (momo-10) of momordin II which introduces an XhoI restriction site:

momo-9 (SEQ ID NO: 55)
5' GATGTTAACTTCGATTTGTCGA 3'
momo-10 (SEQ ID NO: 56)
5' TCAACTCGAGGTACTCAATTCACAACAGATTCC 3' pING3619 was amplified with momo-9 and momo-10, and the product was treated with T4 polymerase, cut with XhoI, and purified on an agarose gel. This gene fragment was ligated along with the 131 bp pelB leader fragment from pIC100 which has been generated by SstI digestion, T4-polymerase treatment, and EcoRI digestion, into the arab expression vector cleaved with EcoRI and XhoI. The product of this three piece ligation was sequenced to verify that the pelB junction and momordin II coding sequence were correct. Arabinose induction of cells containing the momordin II expression plasmid pING3621 results in production of momordin II in *E. coli*.

Analogs of Mormordin II

Mormordin II has no natural cysteines available for conjugation to antibody. Analogs of mormordin which have a free cysteine for conjugation to an antibody may be constructed. Positions likely to be appropriate for substitution of a cysteine residue may be identified from FIG. 3 as positions near the ricin A-chain cysteine$_{259}$ and as positions including the last 26 amino acids of momordin II that are accessible to solvent. For example, the arginine at position 242 of momordin II aligns with the ricin A-chain cysteine at position 259 and is a preferred target for substitution. Additional preferred substitution positions for momordin II include the serine at position 241 and the alanine at position 243.

While the present invention has been described in terms of preferred embodiments, it is understood that variations and improvements will occur to those skilled in the art. Therefore, it is intended that the appended claims cover all such equivalent variations which come within the scope of the invention as claimed.

---

We claim:

1. An isolated polynucleotide encoding an analog of the Type I ribosome inactivating protein, gelonin, wherein a cysteine is substituted for an amino acid which is not naturally available for intermolecular disulfide bonding in gelonin and said cysteine being available for intermolecular disulfide bonding, wherein said gelonin has the amino acid sequence of SEQ ID NO:2 and said cysteine is substituted for an amino acid in said gelonin from amino acid 239 to the carboxy terminal amino acid shown in SEQ ID NO: 2, and wherein said analog retains ribosome inactivating activity of said gelonin.

2. A vector comprising the polynucleotide of claim 1 which encodes an analog of gelonin.

3. A host cell comprising a vector according to claim 2.

4. The isolated polynucleotide recited in claim 1 encoding an analog of gelonin, wherein said gelonin has the amino acid sequence of SEQ ID NO: 2, and wherein said cysteine is substituted for an amino acid at a position in said amino acid sequence of SEQ ID NO: 2 selected from the group consisting of positions 239, 244, 247, and 248.

5. A vector comprising an polynucleotide according to claim 4.

6. A host cell comprising the vector according to claim 5.

7. The host cell recited in claim 6, wherein said host cell is deposited as ATCC accession No. 69009.

8. The isolated polynucleotide recited in claim 1 encoding an analog of gelonin, wherein said gelonin has the amino acid sequence of SEQ ID NO: 2, and wherein additionally the native cysteine residues of said amino acid sequence of SEQ ID NO: 2 at positions 44 and 50 are replaced with alanine residues.

9. A polynucleotide encoding an analog of the Type I ribosome inactivating protein, gelonin as shown in SEQ ID NO: 2, wherein a cysteine is substituted in said analog for another amino acid at an amino acid position not naturally available for intermolecular disulfide bonding in said gelonin and said cysteine being available for intermolecular disulfide bonding, wherein said cysteine is substituted at an amino acid position in said gelonin from position 239 to the carboxy terminal residue, and wherein said analog retains ribosome-inactivating activity of said gelonin.

10. A host cell comprising the vector according to claim 9.

11. An isolated polynucleotide encoding an analog of the Type I ribosome-inactivating protein, gelonin, wherein said gelonin has the amino acid sequence of SEQ ID NO:2 and wherein said analog consists of a cysteine residue substituted for a non-cysteine residue at position 60 in the gelonin amino acid sequence of SEQ ID NO: 2.

12. A vector comprising an polynucleotide according to claim 11.

13. A host cell comprising the vector according to claim 12.

14. An isolated polynucleotide encoding an analog of the Type I ribosome-inactivating protein, gelonin, wherein said gelonin has the amino acid sequence of SEQ ID NO:2 and wherein said analog consists of a non-cysteine residue substituted for a cysteine residue at position 50 in the gelonin amino acid sequence of SEQ ID NO: 2.

15. A vector comprising an polynucleotide according to claim 14.

16. A host cell comprising the vector according to claim 15.

17. An isolated polynucleotide encoding an analog of the Type I ribosome-inactivating protein, gelonin, wherein said gelonin has the amino acid sequence of SEQ ID NO: 2; and wherein a non-cysteine amino acid is substituted at position 44 in SEQ ID NO: 2.

18. A vector comprising the polynucleotide according to claim 17.

19. A host cell comprising the vector according to claim 18.

20. An isolated polynucleotide encoding an analog of the Type I ribosome-inactivating protein, gelonin, wherein said gelonin has the amino acid sequence of SEQ ID NO:2 and wherein said analog consists of a cysteine residue substituted for a non-cysteine residue at position 10 in the gelonin amino acid sequence of SEQ ID NO: 2.

21. A vector comprising the polynucleotide according to claim 20.

22. A host cell comprising the vector according to claim 21.

23. The host cell recited in claim 22, wherein said host cell is deposited as ATCC Accession No. 69008.

* * * * *

SEQUENCE LISTING ( 1 ) GENERAL INFORMATION:

( i i i ) NUMBER OF SEQUENCES: 101

( 2 ) INFORMATION FOR SEQ ID NO:1:

( i ) SEQUENCE CHARACTERISTICS:
( A ) LENGTH: 267 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Ile Phe Pro Lys Gln Tyr Pro Ile Ile Asn Phe Thr Thr Ala Gly Ala
 1               5                  10                  15

Thr Val Gln Ser Tyr Thr Asn Phe Ile Arg Ala Val Arg Gly Arg Leu
                20                  25                  30

Thr Thr Gly Ala Asp Val Arg His Glu Ile Pro Val Leu Pro Asn Arg
            35                  40                  45

Val Gly Leu Pro Ile Asn Gln Arg Phe Ile Leu Val Glu Leu Ser Asn
        50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
```

```
                          100                        105                          110
    Asn Arg Tyr Thr Phe Ala Phe Gly Gly Asn Tyr Asp Arg Leu Glu Gln
            115                        120                125

Leu Ala Gly Asn Leu Arg Glu Asn Ile Glu Leu Gly Asn Gly Pro Leu
        130                        135                140

Glu Glu Ala Ile Ser Ala Leu Tyr Tyr Tyr Ser Thr Gly Gly Thr Gln
    145                        150                155                        160

Leu Pro Thr Leu Ala Arg Ser Phe Ile Ile Cys Ile Gln Met Ile Ser
                    165                        170                175

Glu Ala Ala Arg Phe Gln Tyr Ile Glu Gly Glu Met Arg Thr Arg Ile
                180                        185                190

Arg Tyr Asn Arg Arg Ser Ala Pro Asp Pro Ser Val Ile Thr Leu Glu
            195                        200                205

Asn Ser Trp Gly Arg Leu Ser Thr Ala Ile Gln Glu Ser Asn Gln Gly
        210                        215                220

Ala Phe Ala Ser Pro Ile Gln Leu Gln Arg Arg Asn Gly Ser Lys Phe
    225                        230                235                        240

Ser Val Tyr Asp Val Ser Ile Leu Ile Pro Ile Ile Ala Leu Met Val
                    245                        250                255

Tyr Arg Cys Ala Pro Pro Pro Ser Ser Gln Phe
                260                        265
```

( 2 ) INFORMATION FOR SEQ ID NO:2:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
    Gly Leu Asp Thr Val Ser Phe Ser Thr Lys Gly Ala Thr Tyr Ile Thr
    1               5                   10                  15

Tyr Val Asn Phe Leu Asn Glu Leu Arg Val Lys Leu Lys Pro Glu Gly
                20                  25                  30

Asn Ser His Gly Ile Pro Leu Leu Arg Lys Lys Cys Asp Asp Pro Gly
                35                  40                  45

Lys Cys Phe Val Leu Val Ala Leu Ser Asn Asp Asn Gly Gln Leu Ala
        50                  55                  60

Glu Ile Ala Ile Asp Val Thr Ser Val Tyr Val Val Gly Tyr Gln Val
    65                  70                  75                  80

Arg Asn Arg Ser Tyr Phe Phe Lys Asp Ala Pro Asp Ala Ala Tyr Glu
                    85                  90                  95

Gly Leu Phe Lys Asn Thr Ile Lys Thr Arg Leu His Phe Gly Gly Thr
                100                 105                 110

Tyr Pro Ser Leu Glu Gly Glu Lys Ala Tyr Arg Glu Thr Thr Asp Leu
                115                 120                 125

Gly Ile Glu Pro Leu Arg Ile Gly Ile Lys Lys Leu Asp Glu Asn Ala
        130                 135                 140

Ile Asp Asn Tyr Lys Pro Thr Glu Ile Ala Ser Ser Leu Leu Val Val
    145                 150                 155                 160

Ile Gln Met Val Ser Glu Ala Ala Arg Phe Thr Phe Ile Glu Asn Gln
                    165                 170                 175

Ile Arg Asn Asn Phe Gln Gln Arg Ile Arg Pro Ala Asn Asn Thr Ile
                180                 185                 190

Ser Leu Glu Asn Lys Trp Gly Lys Leu Ser Phe Gln Ile Arg Thr Ser
        195                 200                 205
```

```
            Gly Ala Asn Gly Met Phe Ser Glu Ala Val Glu Leu Glu Arg Ala Asn
                210                 215                 220

Gly Lys Lys Tyr Tyr Val Thr Ala Val Asp Gln Val Lys Pro Lys Ile
            225                 230                 235                 240

Ala Leu Leu Lys Phe Val Asp Lys Asp Pro Lys
                            245                 250
```

( 2 ) INFORMATION FOR SEQ ID NO:3:

( i ) SEQUENCE CHARACTERISTICS:
        ( A ) LENGTH: 280 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
            Ala Ala Lys Met Ala Lys Asn Val Asp Lys Pro Leu Phe Thr Ala Thr
            1               5                   10                  15

Phe Asn Val Gln Ala Ser Ser Ala Asp Tyr Ala Thr Phe Ile Ala Gly
                            20                  25                  30

Ile Arg Asn Lys Leu Arg Asn Pro Ala His Phe Ser His Asn Arg Pro
                        35                  40                  45

Val Leu Pro Pro Val Glu Pro Asn Val Pro Pro Ser Arg Trp Phe His
            50                  55                  60

Val Val Leu Lys Ala Ser Pro Thr Ser Ala Gly Leu Thr Leu Ala Ile
            65                  70                  75                  80

Arg Ala Asp Asn Ile Tyr Leu Glu Gly Phe Lys Ser Ser Asp Gly Thr
                            85                  90                  95

Trp Trp Glu Leu Thr Pro Gly Leu Ile Pro Gly Ala Thr Tyr Val Gly
                        100                 105                 110

Phe Gly Gly Thr Tyr Arg Asp Leu Leu Gly Asp Thr Asp Lys Leu Thr
                        115                 120                 125

Asn Val Ala Leu Gly Arg Gln Gln Leu Ala Asp Ala Val Thr Ala Leu
            130                 135                 140

His Gly Arg Thr Lys Ala Asp Lys Ala Ser Gly Pro Lys Gln Gln Gln
            145                 150                 155                 160

Ala Arg Glu Ala Val Thr Thr Leu Val Leu Met Val Asn Glu Ala Thr
                            165                 170                 175

Arg Phe Gln Thr Val Ser Gly Phe Val Ala Gly Leu Leu His Pro Lys
                        180                 185                 190

Ala Val Glu Lys Lys Ser Gly Lys Ile Gly Asn Glu Met Lys Ala Gln
                        195                 200                 205

Val Asn Gly Trp Gln Asp Leu Ser Ala Ala Leu Leu Lys Thr Asp Val
            210                 215                 220

Lys Pro Pro Pro Gly Lys Ser Pro Ala Lys Phe Ala Pro Ile Glu Lys
            225                 230                 235                 240

Met Gly Val Arg Thr Ala Glu Gln Ala Ala Asn Thr Leu Gly Ile Leu
                            245                 250                 255

Leu Phe Val Glu Val Pro Gly Gly Leu Thr Val Ala Lys Ala Leu Glu
                        260                 265                 270

Leu Phe His Ala Ser Gly Gly Lys
                        275                 280
```

( 2 ) INFORMATION FOR SEQ ID NO:4:

( i ) SEQUENCE CHARACTERISTICS:
        ( A ) LENGTH: 263 amino acids
        ( B ) TYPE: amino acid ( D ) TOPOLOGY: linear ( i i ) MOLECULE TYPE: protein ( x i ) SEQUENCE DESCRIPTION: SEQ ID NO:4:

```
Asp Val Asn Phe Asp Leu Ser Thr Ala Thr Ala Lys Thr Tyr Thr Lys
 1               5                  10                  15
Phe Ile Glu Asp Phe Arg Ala Thr Leu Pro Phe Ser His Lys Val Tyr
            20                  25                  30
Asp Ile Pro Leu Leu Tyr Ser Thr Ile Ser Asp Ser Arg Arg Phe Ile
        35                  40                  45
Leu Leu Asp Leu Thr Ser Tyr Ala Tyr Glu Thr Ile Ser Val Ala Ile
        50                  55                  60
Asp Val Thr Asn Val Tyr Val Ala Tyr Arg Thr Arg Asp Val Ser
65                  70                  75                  80
Tyr Phe Phe Lys Glu Ser Pro Pro Glu Ala Tyr Asn Ile Leu Phe Lys
                85                  90                  95
Gly Thr Arg Lys Ile Thr Leu Pro Tyr Thr Gly Asn Tyr Glu Asn Leu
            100                 105                 110
Gln Thr Ala Ala His Lys Ile Arg Glu Asn Ile Asp Leu Gly Leu Pro
        115                 120                 125
Ala Leu Ser Ser Ala Ile Thr Thr Leu Phe Tyr Tyr Asn Ala Gln Ser
    130                 135                 140
Ala Pro Ser Ala Leu Leu Val Leu Ile Gln Thr Thr Ala Glu Ala Ala
145                 150                 155                 160
Arg Phe Lys Tyr Ile Glu Arg His Val Ala Lys Tyr Val Ala Thr Asn
                165                 170                 175
Phe Lys Pro Asn Leu Ala Ile Ile Ser Leu Glu Asn Gln Trp Ser Ala
            180                 185                 190
Leu Ser Lys Gln Ile Phe Leu Ala Gln Asn Gln Gly Gly Lys Phe Arg
        195                 200                 205
Asn Pro Val Asp Leu Ile Lys Pro Thr Gly Glu Arg Phe Gln Val Thr
    210                 215                 220
Asn Val Asp Ser Asp Val Val Lys Gly Asn Ile Lys Leu Leu Leu Asn
225                 230                 235                 240
Ser Arg Ala Ser Thr Ala Asp Glu Asn Phe Ile Thr Thr Met Thr Leu
                245                 250                 255
Leu Gly Glu Ser Val Val Asn
            260
```

( 2 ) INFORMATION FOR SEQ ID NO:5:

( i ) SEQUENCE CHARACTERISTICS:
      ( A ) LENGTH: 248 amino acids
      ( B ) TYPE: amino acid
      ( D ) TOPOLOGY: linear ( i i ) MOLECULE TYPE: protein ( x i ) SEQUENCE DESCRIPTION: SEQ ID NO:5:

```
Asp Val Arg Phe Ser Leu Ser Gly Ser Ser Thr Ser Tyr Ser Lys
 1               5                  10                  15
Phe Ile Gly Asp Leu Arg Lys Ala Leu Pro Ser Asn Gly Thr Val Tyr
            20                  25                  30
Asn Leu Thr Ile Leu Leu Ser Ser Ala Ser Gly Ala Ser Arg Tyr Thr
        35                  40                  45
Leu Met Thr Leu Ser Asn Tyr Asp Gly Lys Ala Ile Thr Val Ala Val
        50                  55                  60
Asp Val Ser Gln Leu Tyr Ile Met Gly Tyr Leu Val Asn Ser Thr Ser
```

|  | 65 |  |  |  | 70 |  |  |  | 75 |  |  |  | 80 |  |  |
|---|---|---|---|---|---|---|---|---|---|---|---|---|---|---|---|
| Tyr | Phe | Phe | Asn | Glu | Ser | Asp | Ala | Lys | Leu | Ala | Ser | Gln | Tyr | Val | Phe |
|  |  |  |  | 85 |  |  |  |  | 90 |  |  |  |  | 95 |  |
| Lys | Gly | Ser | Thr | Ile | Val | Thr | Leu | Pro | Tyr | Ser | Gly | Asn | Tyr | Glu | Lys |
|  |  |  | 100 |  |  |  |  | 105 |  |  |  |  | 110 |  |  |
| Leu | Gln | Thr | Ala | Ala | Gly | Lys | Ile | Arg | Glu | Lys | Ile | Pro | Leu | Gly | Phe |
|  |  | 115 |  |  |  |  |  | 120 |  |  |  |  | 125 |  |  |
| Pro | Ala | Leu | Asp | Ser | Ala | Leu | Thr | Thr | Ile | Phe | His | Tyr | Asp | Ser | Thr |
|  | 130 |  |  |  |  |  | 135 |  |  |  |  | 140 |  |  |  |
| Ala | Ala | Ala | Ala | Ala | Phe | Leu | Val | Ile | Leu | Gln | Thr | Thr | Ala | Glu | Ala |
| 145 |  |  |  |  | 150 |  |  |  |  | 155 |  |  |  |  | 160 |
| Ser | Arg | Phe | Lys | Tyr | Ile | Glu | Gly | Gln | Ile | Ile | Glu | Arg | Ile | Ser | Lys |
|  |  |  |  | 165 |  |  |  |  | 170 |  |  |  |  | 175 |  |
| Asn | Gln | Val | Pro | Ser | Leu | Ala | Thr | Ile | Ser | Leu | Glu | Asn | Ser | Leu | Trp |
|  |  |  | 180 |  |  |  |  | 185 |  |  |  |  | 190 |  |  |
| Ser | Ala | Leu | Ser | Lys | Gln | Ile | Gln | Leu | Ala | Gln | Thr | Asn | Asn | Gly | Thr |
|  |  | 195 |  |  |  |  |  | 200 |  |  |  |  | 205 |  |  |
| Phe | Lys | Thr | Pro | Val | Val | Ile | Thr | Asp | Asp | Lys | Gly | Gln | Arg | Val | Glu |
|  | 210 |  |  |  |  |  | 215 |  |  |  |  | 220 |  |  |  |
| Ile | Thr | Asn | Val | Thr | Ser | Lys | Val | Val | Thr | Lys | Asn | Ile | Gln | Leu | Leu |
| 225 |  |  |  |  | 230 |  |  |  |  | 235 |  |  |  |  | 240 |
| Leu | Asn | Tyr | Lys | Gln | Asn | Val | Ala |  |  |  |  |  |  |  |  |
|  |  |  |  | 245 |  |  |  |  |  |  |  |  |  |  |  |

( 2 ) INFORMATION FOR SEQ ID NO:6:

( i ) SEQUENCE CHARACTERISTICS:
( A ) LENGTH: 255 amino acids
( B ) TYPE: amino acid
( D ) TOPOLOGY: linear ( i i ) MOLECULE TYPE: protein ( x i ) SEQUENCE DESCRIPTION: SEQ ID NO:6:

|  |  |  |  |  |  |  |  |  |  |  |  |  |  |  |  |
|---|---|---|---|---|---|---|---|---|---|---|---|---|---|---|---|
| Asp | Val | Ser | Phe | Arg | Leu | Ser | Gly | Ala | Thr | Ser | Ser | Ser | Tyr | Gly | Val |
| 1 |  |  |  | 5 |  |  |  |  | 10 |  |  |  |  | 15 |  |
| Phe | Ile | Ser | Asn | Leu | Arg | Lys | Ala | Leu | Pro | Asn | Glu | Arg | Lys | Leu | Tyr |
|  |  |  | 20 |  |  |  |  | 25 |  |  |  |  | 30 |  |  |
| Asp | Leu | Pro | Leu | Ile | Arg | Ser | Ser | Leu | Pro | Gly | Ser | Gln | Arg | Tyr | Ala |
|  |  | 35 |  |  |  |  | 40 |  |  |  |  | 45 |  |  |  |
| Ile | Ile | His | Leu | Thr | Asn | Tyr | Ala | Asp | Glu | Val | Ala | Leu | Asp | Val | Thr |
|  | 50 |  |  |  |  | 55 |  |  |  |  | 60 |  |  |  |  |
| Asn | Val | Asp | Ala | Gly | Leu | Pro | Arg | Asn | Ala | Val | Leu | Tyr | Ile | Met | Gly |
| 65 |  |  |  |  | 70 |  |  |  |  | 75 |  |  |  |  | 80 |
| Tyr | Arg | Ala | Gly | Asp | Thr | Ser | Tyr | Phe | Phe | Asn | Glu | Ala | Ser | Ala | Thr |
|  |  |  |  | 85 |  |  |  |  | 90 |  |  |  |  | 95 |  |
| Glu | Ala | Ala | Lys | Tyr | Val | Phe | Lys | Asp | Ala | Met | Arg | Lys | Val | Thr | Leu |
|  |  |  | 100 |  |  |  |  | 105 |  |  |  |  | 110 |  |  |
| Pro | Tyr | Ser | Gly | Asn | Tyr | Glu | Arg | Leu | Gln | Thr | Ala | Ala | Gly | Gly | Leu |
|  |  | 115 |  |  |  |  | 120 |  |  |  |  | 125 |  |  |  |
| Arg | Glu | Asn | Ile | Pro | Leu | Gly | Leu | Pro | Ala | Leu | Asp | Ser | Ala | Ile | Thr |
|  | 130 |  |  |  |  | 135 |  |  |  |  | 140 |  |  |  |  |
| Thr | Leu | Phe | Tyr | Tyr | Asn | Ala | Asn | Ser | Ala | Ala | Ser | Ala | Leu | Met | Val |
| 145 |  |  |  |  | 150 |  |  |  |  | 155 |  |  |  |  | 160 |
| Leu | Ile | Gln | Ser | Thr | Ser | Glu | Ala | Ala | Arg | Tyr | Lys | Phe | Ile | Glu | Gln |
|  |  |  |  | 165 |  |  |  |  | 170 |  |  |  |  | 175 |  |
| Gln | Ile | Gly | Ser | Arg | Val | Asp | Lys | Thr | Phe | Leu | Pro | Ser | Leu | Ala | Ile |
|  |  |  | 180 |  |  |  |  | 185 |  |  |  |  | 190 |  |  |

```
        Ile  Ser  Leu  Glu  Asn  Ser  Leu  Trp  Leu  Ala  Leu  Ser  Lys  Gln  Ile  Gln
                  195                      200                      205

Ile  Ala  Ser  Thr  Asn  Asn  Gly  Glu  Phe  Glu  Thr  Pro  Val  Val  Leu  Ile
             210                      215                      220

Asn  Ala  Gln  Asn  Gln  Arg  Val  Thr  Ile  Thr  Asn  Val  Asp  Ala  Gly  Val
        225                      230                      235                      240

Val  Thr  Ser  Asn  Ile  Ala  Leu  Leu  Leu  Asn  Arg  Asn  Asn  Met  Ala
                            245                      250                      255
```

( 2 ) INFORMATION FOR SEQ ID NO:7:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
        Asp  Val  Ser  Phe  Arg  Leu  Ser  Gly  Ala  Asp  Pro  Arg  Ser  Tyr  Gly  Met
        1              5                        10                       15

Phe  Ile  Lys  Asp  Leu  Arg  Asn  Ala  Leu  Pro  Phe  Arg  Glu  Lys  Val  Tyr
                       20                       25                       30

Asn  Ile  Pro  Leu  Leu  Leu  Pro  Ser  Val  Ser  Gly  Ala  Gly  Arg  Tyr  Leu
                  35                       40                       45

Leu  Met  His  Leu  Phe  Asn  Tyr  Asp  Gly  Lys  Thr  Ile  Thr  Val  Ala  Val
             50                       55                       60

Asp  Val  Thr  Asn  Val  Tyr  Ile  Met  Gly  Tyr  Leu  Ala  Asp  Thr  Thr  Ser
        65                       70                       75                       80

Tyr  Phe  Phe  Asn  Glu  Pro  Ala  Ala  Glu  Leu  Ala  Ser  Gln  Tyr  Val  Phe
                            85                       90                       95

Arg  Asp  Ala  Arg  Arg  Lys  Ile  Thr  Leu  Pro  Tyr  Ser  Gly  Asn  Tyr  Glu
                            100                      105                      110

Arg  Leu  Gln  Ile  Ala  Ala  Gly  Lys  Pro  Arg  Glu  Lys  Ile  Pro  Ile  Gly
                  115                      120                      125

Leu  Pro  Ala  Leu  Asp  Ser  Ala  Ile  Ser  Thr  Leu  Leu  His  Tyr  Asp  Ser
             130                      135                      140

Thr  Ala  Ala  Ala  Gly  Ala  Leu  Leu  Val  Leu  Ile  Gln  Thr  Thr  Ala  Glu
        145                      150                      155                      160

Ala  Ala  Arg  Phe  Lys  Tyr  Ile  Glu  Gln  Gln  Ile  Gln  Glu  Arg  Ala  Tyr
                            165                      170                      175

Arg  Asp  Glu  Val  Pro  Ser  Leu  Ala  Thr  Ile  Ser  Leu  Glu  Asn  Ser  Trp
                       180                      185                      190

Ser  Gly  Leu  Ser  Lys  Gln  Ile  Gln  Leu  Ala  Gln  Gly  Asn  Asn  Gly  Ile
                  195                      200                      205

Phe  Arg  Thr  Pro  Ile  Val  Leu  Val  Asp  Asn  Lys  Gly  Asn  Arg  Val  Gln
             210                      215                      220

Ile  Thr  Asn  Val  Thr  Ser  Lys  Val  Val  Thr  Ser  Asn  Ile  Gln  Leu  Leu
        225                      230                      235                      240

Leu  Asn  Thr  Arg  Asn  Ile  Ala  Glu  Gly  Asp  Asn  Gly  Asp  Val  Ser  Thr
                            245                      250                      255

Thr  His  Gly  Phe  Ser  Ser  Thr
                       260
```

( 2 ) INFORMATION FOR SEQ ID NO:8:

( i ) SEQUENCE CHARACTERISTICS:
        ( A ) LENGTH: 250 amino acids
        ( B ) TYPE: amino acid ( D ) TOPOLOGY: linear ( i i ) MOLECULE TYPE: protein ( x i ) SEQUENCE DESCRIPTION: SEQ ID NO:8:

| Ala | Pro | Thr | Leu | Glu | Thr | Ile | Ala | Ser | Leu | Asp | Leu | Asn | Asn | Pro | Thr |
|---|---|---|---|---|---|---|---|---|---|---|---|---|---|---|---|
| 1 | | | | 5 | | | | | 10 | | | | | 15 | |
| Thr | Tyr | Leu | Ser | Phe | Ile | Thr | Asn | Ile | Arg | Thr | Lys | Val | Ala | Asp | Lys |
| | | | 20 | | | | 25 | | | | | 30 | | | |
| Thr | Glu | Gln | Cys | Thr | Ile | Gln | Lys | Ile | Ser | Lys | Thr | Phe | Thr | Gln | Arg |
| | | 35 | | | | 40 | | | | | 45 | | | | |
| Tyr | Ser | Tyr | Ile | Asp | Leu | Ile | Val | Ser | Ser | Thr | Gln | Lys | Ile | Thr | Leu |
| | 50 | | | | 55 | | | | | 60 | | | | | |
| Ala | Ile | Asp | Met | Ala | Asp | Leu | Tyr | Val | Leu | Gly | Tyr | Ser | Asp | Ile | Ala |
| 65 | | | | 70 | | | | | 75 | | | | | | 80 |
| Asn | Asn | Lys | Gly | Arg | Ala | Phe | Phe | Lys | Asp | Val | Thr | Glu | Ala | Val | |
| | | | | 85 | | | | | 90 | | | | | 95 | |
| Ala | Asn | Asn | Phe | Phe | Pro | Gly | Ala | Thr | Gly | Thr | Asn | Arg | Ile | Lys | Leu |
| | | | 100 | | | | | 105 | | | | | 110 | | |
| Thr | Phe | Thr | Gly | Ser | Tyr | Gly | Asp | Leu | Glu | Lys | Asn | Gly | Gly | Leu | Arg |
| | | 115 | | | | | 120 | | | | | 125 | | | |
| Lys | Asp | Asn | Pro | Leu | Gly | Ile | Phe | Arg | Leu | Glu | Asn | Ser | Ile | Val | Asn |
| | 130 | | | | | 135 | | | | | 140 | | | | |
| Ile | Tyr | Gly | Lys | Ala | Gly | Asp | Val | Lys | Lys | Gln | Ala | Lys | Phe | Phe | Leu |
| 145 | | | | | 150 | | | | | 155 | | | | | 160 |
| Leu | Ala | Ile | Gln | Met | Val | Ser | Glu | Ala | Ala | Arg | Phe | Lys | Tyr | Ile | Ser |
| | | | | 165 | | | | | 170 | | | | | 175 | |
| Asp | Lys | Ile | Pro | Ser | Glu | Lys | Tyr | Glu | Glu | Val | Thr | Val | Asp | Glu | Tyr |
| | | | 180 | | | | | 185 | | | | | 190 | | |
| Met | Thr | Ala | Leu | Glu | Asn | Asn | Trp | Ala | Lys | Leu | Ser | Thr | Ala | Val | Tyr |
| | | 195 | | | | | 200 | | | | | 205 | | | |
| Asn | Ser | Lys | Pro | Ser | Thr | Thr | Thr | Ala | Thr | Lys | Cys | Gln | Leu | Ala | Thr |
| | 210 | | | | | 215 | | | | | 220 | | | | |
| Ser | Pro | Val | Thr | Ile | Ser | Pro | Trp | Ile | Phe | Lys | Thr | Val | Glu | Glu | Ile |
| 225 | | | | | 230 | | | | | 235 | | | | | 240 |
| Lys | Leu | Val | Met | Gly | Leu | Leu | Lys | Ser | Ser | | | | | | |
| | | | | 245 | | | | | 250 | | | | | | |

( 2 ) INFORMATION FOR SEQ ID NO:9:

( i ) SEQUENCE CHARACTERISTICS:
( A ) LENGTH: 261 amino acids
( B ) TYPE: amino acid
( D ) TOPOLOGY: linear ( i i ) MOLECULE TYPE: protein ( x i ) SEQUENCE DESCRIPTION: SEQ ID NO:9:

| Ile | Asn | Thr | Ile | Thr | Phe | Asp | Ala | Gly | Asn | Ala | Thr | Ile | Asn | Lys | Tyr |
|---|---|---|---|---|---|---|---|---|---|---|---|---|---|---|---|
| 1 | | | | 5 | | | | | 10 | | | | | 15 | |
| Ala | Thr | Phe | Met | Glu | Ser | Leu | Arg | Asn | Glu | Ala | Lys | Asp | Pro | Ser | Leu |
| | | | 20 | | | | | 25 | | | | | 30 | | |
| Lys | Cys | Tyr | Gly | Ile | Pro | Met | Leu | Pro | Asn | Thr | Asn | Ser | Thr | Ile | Lys |
| | | 35 | | | | | 40 | | | | | 45 | | | |
| Tyr | Leu | Leu | Val | Lys | Leu | Gln | Gly | Ala | Ser | Leu | Lys | Thr | Ile | Thr | Leu |
| | 50 | | | | | 55 | | | | | 60 | | | | |
| Met | Leu | Arg | Arg | Asn | Asn | Leu | Tyr | Val | Met | Gly | Tyr | Ser | Asp | Pro | Tyr |
| 65 | | | | | 70 | | | | | 75 | | | | | 80 |
| Asp | Asn | Lys | Cys | Arg | Tyr | His | Ile | Phe | Asn | Asp | Ile | Lys | Gly | Thr | Glu |

|  |  |  | 85 |  |  |  |  | 90 |  |  |  |  | 95 |  |  |
|---|---|---|---|---|---|---|---|---|---|---|---|---|---|---|---|

```
        Tyr   Ser   Asp   Val   Glu   Asn   Thr   Leu   Cys   Pro   Ser   Ser   Asn   Pro   Arg   Val
                          100                           105                     110

Ala   Lys   Pro   Ile   Asn   Tyr   Asn   Gly   Leu   Tyr   Pro   Thr   Leu   Glu   Lys   Lys
                    115                           120                           125

Ala   Gly   Val   Thr   Ser   Arg   Asn   Glu   Val   Gln   Leu   Gly   Ile   Gln   Ile   Leu
              130                                 135                           140

Ser   Ser   Lys   Ile   Gly   Lys   Ile   Ser   Gly   Gln   Gly   Ser   Phe   Thr   Glu   Lys
        145                           150                           155                           160

Ile   Glu   Ala   Asp   Phe   Leu   Leu   Val   Ala   Ile   Gln   Met   Val   Ser   Glu   Ala
                                165                           170                           175

Ala   Arg   Phe   Lys   Tyr   Ile   Glu   Asn   Gln   Val   Lys   Thr   Asn   Phe   Asn   Arg
                          180                           185                           190

Asp   Phe   Ser   Pro   Asn   Asp   Lys   Val   Leu   Asp   Leu   Glu   Glu   Asn   Trp   Gly
                    195                           200                           205

Lys   Ile   Ser   Thr   Ala   Ile   His   Asn   Ser   Lys   Asn   Gly   Ala   Leu   Pro   Lys
              210                           215                           220

Pro   Leu   Glu   Leu   Lys   Asn   Ala   Asp   Gly   Thr   Lys   Trp   Ile   Val   Leu   Arg
        225                           230                           235                           240

Val   Asp   Glu   Ile   Lys   Pro   Asp   Val   Gly   Leu   Leu   Asn   Tyr   Val   Asn   Gly
                                245                           250                           255

Thr   Cys   Gln   Ala   Thr
                          260
```

( 2 ) INFORMATION FOR SEQ ID NO:10:

( i ) SEQUENCE CHARACTERISTICS:
        ( A ) LENGTH: 259 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
        Val   Thr   Ser   Ile   Thr   Leu   Asp   Leu   Val   Asn   Pro   Thr   Ala   Gly   Gln   Tyr
        1                       5                           10                            15

Ser   Ser   Phe   Val   Asp   Lys   Ile   Arg   Asn   Asn   Val   Lys   Asp   Pro   Asn   Leu
                          20                            25                            30

Lys   Tyr   Gly   Gly   Thr   Asp   Ile   Ala   Val   Ile   Gly   Pro   Pro   Ser   Lys   Glu
                    35                            40                            45

Lys   Phe   Leu   Arg   Ile   Asn   Phe   Gln   Ser   Ser   Arg   Gly   Thr   Val   Ser   Leu
              50                            55                            60

Gly   Leu   Lys   Arg   Asp   Asn   Leu   Tyr   Val   Val   Ala   Tyr   Leu   Ala   Met   Asp
        65                            70                            75                            80

Asn   Thr   Asn   Val   Asn   Arg   Ala   Tyr   Tyr   Phe   Arg   Ser   Glu   Ile   Thr   Ser
                                85                            90                            95

Ala   Glu   Ser   Thr   Ala   Leu   Phe   Pro   Glu   Ala   Thr   Thr   Ala   Asn   Gln   Lys
                          100                           105                           110

Ala   Leu   Glu   Tyr   Thr   Glu   Asp   Tyr   Gln   Ser   Ile   Glu   Lys   Asn   Ala   Gln
                    115                           120                           125

Ile   Thr   Gln   Gly   Asp   Gln   Ser   Arg   Lys   Glu   Leu   Gly   Leu   Gly   Ile   Asp
              130                           135                           140

Leu   Leu   Ser   Thr   Ser   Met   Glu   Ala   Val   Asn   Lys   Lys   Ala   Arg   Val   Val
        145                           150                           155                           160

Lys   Asp   Glu   Ala   Arg   Phe   Leu   Leu   Ile   Ala   Ile   Gln   Met   Thr   Ala   Glu
                                165                           170                           175

Ala   Ala   Arg   Phe   Arg   Tyr   Ile   Gln   Asn   Leu   Val   Ile   Lys   Asn   Phe   Pro
                          180                           185                           190
```

|  |  |  |  |  |  |  |  |  |  |  |  |  |  |
|---|---|---|---|---|---|---|---|---|---|---|---|---|---|
| Asn | Lys | Phe<br>195 | Asn | Ser | Glu | Asn<br>200 | Lys | Val | Ile | Gln | Phe<br>205 | Glu | Val | Asn | Trp |
| Lys | Lys<br>210 | Ile | Ser | Thr | Ala<br>215 | Ile | Tyr | Gly | Asp | Ala<br>220 | Lys | Asn | Gly | Val | Phe |
| Asn<br>225 | Lys | Asp | Tyr | Asp<br>230 | Phe | Gly | Phe | Gly | Lys<br>235 | Val | Arg | Gln | Val | Lys<br>240 | Asp |
| Leu | Gln | Met | Gly | Leu<br>245 | Leu | Met | Tyr | Leu | Gly<br>250 | Lys | Pro | Lys | Ser<br>255 | Ser | Asn |
| Glu | Ala | Asn |

( 2 ) INFORMATION FOR SEQ ID NO:11:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GGGCTAGATA CCGTGTCATT CTCAACCAAA GGTGCCACTT ATATTACCTA CGTGAATTTC    60
TTGAATGAGC TACGAGTTAA ATTGAAACCC GAAGGTAACA GCCATGGAAT CCCATTGCTG   120
CGCAAAAAAT GTGATGATCC TGGAAAGTGT TTCGTTTTGG TAGCGCTTTC AAATGACAAT   180
GGACAGTTGG CGGAAATAGC TATAGATGTT ACAAGTGTTT ATGTGGTGGG CTATCAAGTA   240
AGAAACAGAT CTTACTTCTT TAAAGATGCT CCAGATGCTG CTTACGAAGG CCTCTTCAAA   300
AACACAATTA AACAAGACT TCATTTTGGC GGCACGTATC CCTCGCTGGA AGGTGAGAAG    360
GCATATAGAG AGACAACAGA CTTGGGCATT GAACCATTAA GGATTGGCAT CAAGAAACTT   420
GATGAAAATG CGATAGACAA TTATAAACCA ACGGAGATAG CTAGTTCTCT ATTGGTTGTT   480
ATTCAAATGG TGTCTGAAGC AGCTCGATTC ACCTTTATTG AGAACCAAAT TAGAAATAAC   540
TTTCAACAGA GAATTCGCCC GGCGAATAAT ACAATCAGCC TTGAGAATAA ATGGGGTAAA   600
CTCTCGTTCC AGATCCGGAC ATCAGGTGCA AATGGAATGT TTTCGGAGGC AGTTGAATTG   660
GAACGTGCAA ATGGCAAAAA ATACTATGTC ACCGCAGTTG ATCAAGTAAA ACCCAAAATA   720
GCACTCTTGA AGTTCGTCGA TAAAGATCCT AAAACGAGCC TTGCTGCTGA ATTGATAATC   780
CAGAACTATG AGTCATTAGT GGGCTTTGAT TAG                                813
```

( 2 ) INFORMATION FOR SEQ ID NO:12:

( i ) SEQUENCE CHARACTERISTICS:
        ( A ) LENGTH: 846 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
ATGGCGGCAA AGATGGCGAA GAACGTGGAC AAGCCGCTCT TCACCGCGAC GTTCAACGTC    60
CAGGCCAGCT CCGCCGACTA CGCCACCTTC ATCGCCGGCA TCCGCAACAA GCTCCGCAAC   120
CCGGCGCACT TCTCCCACAA CCGCCCCGTG CTGCCGCCGG TCGAGCCCAA CGTCCCGCCG   180
AGCAGGTGGT TCCACGTCGT GCTCAAGGCC TCGCCGACCA GCGCCGGGCT CACGCTGGCC   240
ATCCGCGCGG ACAACATCTA CCTGGAGGGC TTCAAGAGCA GCGACGGCAC CTGGTGGGAG   300
CTCACCCCGG GCCTCATCCC CGGCGCCACC TACGTCGGGT TCGGCGGCAC CTACCGCGAC   360
CTCCTCGGCG ACACCGACAA GCTAACCAAC GTCGCTCTCG GCCGACAGCA GCTGGCGGAC   420
```

| | | | | | |
|---|---|---|---|---|---|
|GCGGTGACCG|CGCTCCACGG|GCGCACCAAG|GCCGACAAGG|CCTCCGGCCC|GAAGCAGCAG| 480
|CAGGCGAGGG|AGGCGGTGAC|GACGCTGGTC|CTCATGGTGA|ACGAGGCCAC|GCGGTTCCAG| 540
|ACGGTGTCTG|GGTTCGTGGC|CGGGTTGCTG|CACCCCAAGG|CGGTGGAGAA|GAAGAGCGGG| 600
|AAGATCGGCA|ATGAGATGAA|GGCCCAGGTG|AACGGGTGGC|AGGACCTGTC|CGCGGCGCTG| 660
|CTGAAGACGG|ACGTGAAGCC|TCCGCCGGGA|AAGTCGCCAG|CGAAGTTCGC|GCCGATCGAG| 720
|AAGATGGGCG|TGAGGACGGC|TGAACAGGCC|GCCAACACGC|TGGGGATCCT|GCTGTTCGTG| 780
|GAGGTGCCGG|GTGGGTTGAC|GGTGGCCAAG|GCGCTGGAGC|TGTTCCATGC|GAGTGGTGGG| 840
|AAATAG| | | | | 846

(2) INFORMATION FOR SEQ ID NO:13:

(i) SEQUENCE CHARACTERISTICS:
       (A) LENGTH: 913 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:13:

| | | | | | |
|---|---|---|---|---|---|
|CGTCCGAAAA|TGGTGAAATG|CTTACTACTT|TCTTTTTTAA|TTATCGCCAT|CTTCATTGGT| 60
|GTTCCTACTG|CCAAAGGCGA|TGTTAACTTC|GATTTGTCGA|CTGCCACTGC|AAAAACCTAC| 120
|ACAAAATTTA|TCGAAGATTT|CAGGGCGACT|CTTCCATTTA|GCCATAAAGT|GTATGATATA| 180
|CCTCTACTGT|ATTCCACTAT|TTCCGACTCC|AGACGTTTCA|TACTCCTCGA|TCTTACAAGT| 240
|TATGCATATG|AAACCATCTC|GGTGGCCATA|GATGTGACGA|ACGTTTATGT|TGTGGCGTAT| 300
|CGCACCCGCG|ATGTATCCTA|CTTTTTTAAA|GAATCTCCTC|CTGAAGCTTA|TAACATCCTA| 360
|TTCAAAGGTA|CGCGGAAAAT|TACACTGCCA|TATACCGGTA|ATTATGAAAA|TCTTCAAACT| 420
|GCTGCACACA|AAATAAGAGA|GAATATTGAT|CTTGGACTCC|CTGCCTTGAG|TAGTGCCATT| 480
|ACCACATTGT|TTTATTACAA|TGCCCAATCT|GCTCCTTCTG|CATTGCTTGT|ACTAATCCAG| 540
|ACGACTGCAG|AAGCTGCAAG|ATTTAAGTAT|ATCGAGCGAC|ACGTTGCTAA|GTATGTTGCC| 600
|ACTAACTTTA|AGCCAAATCT|AGCCATCATA|AGCTTGGAAA|ATCAATGGTC|TGCTCTCTCC| 660
|AACAAATCTT|TTTGGCGCAG|AATCAAGGAG|GAAAATTTAG|AAATCCTGTC|GACCTTATAA| 720
|AACCTACCGG|GGAACGGTTT|CAAGTAACCA|ATGTTGATTC|AGATGTTGTA|AAAGGTAATA| 780
|TCAAACTCCT|GCTGAACTCC|AGAGCTAGCA|CTGCTGATGA|AAACTTTATC|ACAACCATGA| 840
|CTCTACTTGG|GGAATCTGTT|GTGAATTGAA|AGTTTAATAA|TCCACCCATA|TCGAAATAAG| 900
|GCATGTTCAT|GAC| | | | | 913

(2) INFORMATION FOR SEQ ID NO:14:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:14:

TTYAARGAYG CNCCNGAYGC NGCNTAYGAR GG                                32

(2) INFORMATION FOR SEQ ID NO:15:

(i) SEQUENCE CHARACTERISTICS:
       (A) LENGTH: 32 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

ACYTGRTCNA CNGCNGTNAC RTARTAYTTY TT        32

( 2 ) INFORMATION FOR SEQ ID NO:16:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:16:

GGNYTNGAYA CNGTN W SNTT Y W SNACNAAR GG        32

( 2 ) INFORMATION FOR SEQ ID NO:17:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:17:

AATGGTTCAA TGCCCAAGTC TGT        23

( 2 ) INFORMATION FOR SEQ ID NO:18:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:18:

TGTCTCTCTA TATGCCTTTC CAC        23

( 2 ) INFORMATION FOR SEQ ID NO:19:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:19:

TCAACCCGGG CTAGATACCG TGTCATTCTC AACCAAAGGT GCCACTTATA TTA        53

( 2 ) INFORMATION FOR SEQ ID NO:20:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:20:

CTTCATTTTG GCGGCACGTA TCC　　　　　　　　　　　　　　　　　　　　　　　　　　23

( 2 ) INFORMATION FOR SEQ ID NO:21:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CTCGAGGCTG CAAGCTTACG TGGGATTTTT TTTTTTTTT TTTTTT　　　　　　　　　　　　46

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

CTCGCTGGAA GGTGAGAA　　　　　　　　　　　　　　　　　　　　　　　　　　　　18

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

CTCGAGGCTG CAAGCTTACG TGGGA　　　　　　　　　　　　　　　　　　　　　　　25

( 2 ) INFORMATION FOR SEQ ID NO:24:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

TGATCTCGAG TACTATTTAG GATCTTTATC GACGA　　　　　　　　　　　　　　　　　35

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTAAGCAGCA TCTGGAGCAT CT　　　　　　　　　　　　　　　　　　　　　　　　22

( 2 ) INFORMATION FOR SEQ ID NO:26:

( i ) SEQUENCE CHARACTERISTICS:

( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CATTCAAGAA ATTCACGTAG G                                                              21

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

GGCCTGGACA CCGTGAGCTT TAG                                                            23

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

TCGATTGCGA TCCTAAATAG TACTC                                                          25

( 2 ) INFORMATION FOR SEQ ID NO:29:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

TTTAGGATCG CAATCGACGA ACTTCAAG                                                       28

( 2 ) INFORMATION FOR SEQ ID NO:30:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

GTTCGTCTGT AAAGATCCTA AATAGTACTC GA                                                  32

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

GGATCTTTAC AGACGAACTT CAAGAGT 27

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TCTTGTGCTT CGTCGATAAA GATCC 25

( 2 ) INFORMATION FOR SEQ ID NO:33:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

ATCGACGAAG CACAAGAGTG CTATTTT 27

( 2 ) INFORMATION FOR SEQ ID NO:34:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GTAAAACCAT GCATAGCACT CTTGAAGTTC GT 32

( 2 ) INFORMATION FOR SEQ ID NO:35:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

AGTGCTATGC ATGGTTTTAC TTGATCAACT GC 32

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

AGCACATGTG GTGCCACTTA TATTACCTA 29

( 2 ) INFORMATION FOR SEQ ID NO:37:

( i ) SEQUENCE CHARACTERISTICS:
       ( A ) LENGTH: 33 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:37:

TAAGTGGCAC CACATGTGCT AAAGCTCACG GTG    33

( 2 ) INFORMATION FOR SEQ ID NO:38:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:38:

TGACTGTGGA CAGTTGGCGG AAATA    25

( 2 ) INFORMATION FOR SEQ ID NO:39:

( i ) SEQUENCE CHARACTERISTICS:
              ( A ) LENGTH: 32 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:39:

GCCACTGTCC ACAGTCATTT GAAAGCGCTA CC    32

( 2 ) INFORMATION FOR SEQ ID NO:40:

( i ) SEQUENCE CHARACTERISTICS:
              ( A ) LENGTH: 36 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:40:

GATGATCCTG GAAAGGCTTT CGTTTGGTA GCGCTT    36

( 2 ) INFORMATION FOR SEQ ID NO:41:

( i ) SEQUENCE CHARACTERISTICS:
              ( A ) LENGTH: 41 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:41:

AAGCCTTTCC AGGATCATCA GCTTTTTTGG GCAGCAATGG G    41

( 2 ) INFORMATION FOR SEQ ID NO:42:

( i ) SEQUENCE CHARACTERISTICS:
              ( A ) LENGTH: 23 base pairs
              ( B ) TYPE: nucleic acid
              ( C ) STRANDEDNESS: single
              ( D ) TOPOLOGY: linear ( i i ) MOLECULE TYPE: DNA ( x i ) SEQUENCE DESCRIPTION: SEQ ID NO:42:

AAGCCTTTCC AGGATCATCA CAT  23

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GCGACTCTCT ACTGTTTC  18

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGTTAGCAAT TTAACTGTGA T  21

( 2 ) INFORMATION FOR SEQ ID NO:45:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

AACAGCTATG ACCATG  16

( 2 ) INFORMATION FOR SEQ ID NO:46:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

TGAACTCGAG GAAACTACCT ATTTCCCAC  29

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

GCATTACATC CATGGCGGC  19

( 2 ) INFORMATION FOR SEQ ID NO:48:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:48:

GATATCTCGA GTTAACTATT TCCCACCACA CGCATGGAAC AGCTCCAGCG CCTTGGCCAC    60

CGTC    64

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

TATCTGTTCG TGGAGGTGCC G    21

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

CGTTAGCAAT TTAACTGTGA T    21

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CCAAGTGTCT GGAGCTGTTC CATGCGA    27

( 2 ) INFORMATION FOR SEQ ID NO:52:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

GATGTTAAYT TYGAYTTGTC NACDGCTAC    29

( 2 ) INFORMATION FOR SEQ ID NO:53:

( i ) SEQUENCE CHARACTERISTICS:
        ( A ) LENGTH: 29 base pairs
        ( B ) TYPE: nucleic acid
        ( C ) STRANDEDNESS: single (D) TOPOLOGY: linear (ii) MOLECULE TYPE: DNA (xi) SEQUENCE DESCRIPTION: SEQ ID NO:53:

ATTGGNAGDG TAGCCCTRAA RTCYTCDAT 29

(2) INFORMATION FOR SEQ ID NO:54:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:54:

GCCACTGCAA AAACCTACAC AAAATTTATT GA 32

(2) INFORMATION FOR SEQ ID NO:55:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:55:

GATGTTAACT TCGATTTGTC GA 22

(2) INFORMATION FOR SEQ ID NO:56:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:56:

TCAACTCGAG GTACTCAATT CACAACAGAT TCC 33

(2) INFORMATION FOR SEQ ID NO:57:

(i) SEQUENCE CHARACTERISTICS:
(A) LENGTH: 813 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:57:

GGCCTGGACA CCGTGAGCTT TAGCACTAAA GGTGCCACTT ATATTACCTA CGTGAATTTC 60

TTGAATGAGC TACGAGTTAA ATTGAAACCC GAAGGTAACA GCCATGGAAT CCCATTGCTG 120

CGCAAAAAAT GTGATGATCC TGGAAAGTGT TTCGTTTTGG TAGCGCTTTC AAATGACAAT 180

GGACAGTTGG CGGAAATAGC TATAGATGTT ACAAGTGTTT ATGTGGTGGG CTATCAAGTA 240

AGAAACAGAT CTTACTTCTT TAAAGATGCT CCAGATGCTG CTTACGAAGG CCTCTTCAAA 300

AACACAATTA AACAAGACT TCATTTTGGC GGCACGTATC CCTCGCTGGA AGGTGAGAAG 360

GCATATAGAG AGACAACAGA CTTGGGCATT GAACCATTAA GGATTGGCAT CAAGAAACTT 420

GATGAAAATG CGATAGACAA TTATAAACCA ACGGAGATAG CTAGTTCTCT ATTGGTTGTT 480

```
ATTCAAATGG TGTCTGAAGC AGCTCGATTC ACCTTTATTG AGAACCAAAT TAGAAATAAC      540

TTTCAACAGA GAATTCGCCC GGCGAATAAT ACAATCAGCC TTGAGAATAA ATGGGGTAAA      600

CTCTCGTTCC AGATCCGGAC ATCAGGTGCA AATGGAATGT TTTCGGAGGC AGTTGAATTG      660

GAACGTGCAA ATGGCAAAAA ATACTATGTC ACCGCAGTTG ATCAAGTAAA ACCCAAAATA      720

GCACTCTTGA AGTTCGTCGA TAAAGATCCT AAAACGAGCC TTGCTGCTGA ATTGATAATC      780

CAGAACTATG AGTCATTAGT GGGCTTTGAT TAG                                   813
```

( 2 ) INFORMATION FOR SEQ ID NO:58:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:58:

```
Cys His His His Ala Ser Arg Val Ala Arg Met Ala Ser Asp Glu Phe
1               5                   10                  15

Pro Ser Met Cys
            20
```

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:59:

```
Pro Ser Gly Gln Ala Gly Ala Ala Ala Ser Glu Ser Leu Phe Ile Ser
1               5                   10                  15

Asn His Ala Tyr
            20
```

( 2 ) INFORMATION FOR SEQ ID NO:60:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

```
CAGCCATGGA ATCCCATTGC TG                                                22
```

( 2 ) INFORMATION FOR SEQ ID NO:61:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:61:

```
CACATGTAAA ACAAGACTTC ATTTTGGC                                          28
```

( 2 ) INFORMATION FOR SEQ ID NO:62:

( i ) SEQUENCE CHARACTERISTICS:

-continued ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:62:

TGAAGTCTTG TTTTAGATGT GTTTTTGAAG AGGCCT        36

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:63:

ATGCCATATG CAATTATAAA CCAACGGAGA        30

( 2 ) INFORMATION FOR SEQ ID NO:64:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:64:

GGTTTATAAT TGCATATGGC ATTTTCATCA AGTTTCTTG        39

( 2 ) INFORMATION FOR SEQ ID NO:65:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:65:

CTTTCAACAA TGCATTCGCC CGGCGAATAA TAC        33

( 2 ) INFORMATION FOR SEQ ID NO:66:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:66:

GCGAATGCAT TGTTGAAAGT TATTTCTAAT TTG        33

( 2 ) INFORMATION FOR SEQ ID NO:67:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:67:

GTTTTGTGAG GCAGTTGAAT TGGAAC   26

( 2 ) INFORMATION FOR SEQ ID NO:68:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:68:

TTCAACTGCC TCACAAAACA TTCCATTTGC ACCT   34

( 2 ) INFORMATION FOR SEQ ID NO:69:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:69:

AAAAGCTGAT GATCCTGGAA AGTG   24

( 2 ) INFORMATION FOR SEQ ID NO:70:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:70:

TCCAGGATCA TCAGCTTTTT TGCGCAGCAA TGGGA   35

( 2 ) INFORMATION FOR SEQ ID NO:71:

( i ) SEQUENCE CHARACTERISTICS:
        ( A ) LENGTH: 321 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:71:

GACATCCAGA TGACTCAGTC TCCATCTTCC ATGTCTGCAT CTCTGGGAGA CAGAGTCACT   60

ATCACTTGCC GGGCGAGTCA GGACATTAAT AGCTATTTAA GCTGGTTCCA GCAGAAACCA   120

GGGAAATCTC CTAAGACCCT GATCTATCGT GCAAACAGAT TGGTAGATGG GGTCCCATCA   180

AGGTTCAGTG GCAGTGGATC TGGGACAGAT TATACTCTCA CCATCAGCAG CCTGCAATAT   240

GAAGATTTTG GAATTTATTA TTGTCAACAG TATGATGAGT CTCCGTGGAC GTTCGGTGGA   300

GGCACCAAGC TTGAAATCAA A   321

( 2 ) INFORMATION FOR SEQ ID NO:72:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

| | | | | | |
|---|---|---|---|---|---|
| CAGATCCAGT | TGGTGCAGTC | TGGACCTGGC | CTGAAGAAGC | CTGGAGGGTC | CGTCAGAATC | 60 |
| TCCTGCGCAG | CTTCTGGGTA | TACCTTCACA | AACTATGGAA | TGAACTGGGT | GAAGCAGGCT | 120 |
| CCAGGAAAGG | GTTTAAGGTG | GATGGGCTGG | ATAAACACCC | ACACTGGAGA | GCCAACATAT | 180 |
| GCTGATGACT | TCAAGGGACG | GTTTACCTTC | TCTTTGGACA | CGTCTAAGAG | CACTGCCTAT | 240 |
| TTACAGATCA | ACAGCCTCAG | AGCCGAGGAC | ACGGCTACAT | ATTTCTGTAC | AAGACGGGGT | 300 |
| TACGACTGGT | ACTTCGATGT | CTGGGGCCAA | GGGACCACGG | TCACCGTCTC | CTCC | 354 |

( 2 ) INFORMATION FOR SEQ ID NO:73:

( i ) SEQUENCE CHARACTERISTICS:
( A ) LENGTH: 354 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:73:

| | | | | | |
|---|---|---|---|---|---|
| GAGATCCAGT | TGGTGCAGTC | TGGAGGAGGC | CTGGTGAAGC | CTGGAGGGTC | CGTCAGAATC | 60 |
| TCCTGCGCAG | CTTCTGGGTA | TACCTTCACA | AACTATGGAA | TGAACTGGGT | GCGCCAGGCT | 120 |
| CCAGGAAAGG | GTTTAGAGTG | GATGGGCTGG | ATAAACACCC | ACACTGGAGA | GCCAACATAT | 180 |
| GCTGATTCTT | TCAAGGGACG | GTTTACCTTC | TCTTTGGACG | ATTCTAAGAA | CACTGCCTAT | 240 |
| TTACAGATCA | ACAGCCTCAG | AGCCGAGGAC | ACGGCTGTGT | ATTTCTGTAC | AAGACGGGGT | 300 |
| TACGACTGGT | ACTTCGATGT | CTGGGGCCAA | GGGACCACGG | TCACCGTCTC | CTCC | 354 |

( 2 ) INFORMATION FOR SEQ ID NO:74:

( i ) SEQUENCE CHARACTERISTICS:
( A ) LENGTH: 321 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:74:

| | | | | | |
|---|---|---|---|---|---|
| GACATCCAGA | TGACTCAGTC | TCCATCTTCC | CTGTCTGCAT | CTGTAGGAGA | CAGAGTCACT | 60 |
| ATCACTTGCC | GGGCGAGTCA | GGACATTAAT | AGCTATTTAA | GCTGGTTCCA | GCAGAAACCA | 120 |
| GGGAAAGCTC | CTAAGACCCT | GATCTATCGT | GCAAACAGAT | TGGAATCTGG | GGTCCCATCA | 180 |
| AGGTTCAGTG | GCAGTGGATC | TGGGACAGAT | TATACTCTCA | CCATCAGCAG | CCTGCAATAT | 240 |
| GAAGATTTTG | GAATTTATTA | TTGTCAACAG | TATGATGAGT | CTCCGTGGAC | GTTCGGTGGA | 300 |
| GGCACCAAGC | TTGAAATCAA | A | | | | 321 |

( 2 ) INFORMATION FOR SEQ ID NO:75:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:75:

| | | | | | |
|---|---|---|---|---|---|
| TGTCATCATC | ATGCATCGCG | AGTTGCCAGA | ATGGCATCTG | ATGAGTTTCC | TTCTATGTGC | 60 |

GCAAGTACTC 70

(2) INFORMATION FOR SEQ ID NO:76:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

TCGAGAGTAC TTGCGCACAT AGAAGGAAAC TCATCAGATG CCATTCTGGC AACTCGCGAT 60

GCATGATGAT GACATGCA 78

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:77:

TGTTCGGCCG CATGTCATCA TCATGCATCG 30

(2) INFORMATION FOR SEQ ID NO:78:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:78:

AGTCATGCCC CGCGC 15

(2) INFORMATION FOR SEQ ID NO:79:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:79:

TCCCGGCTGT CCTACAGT 18

(2) INFORMATION FOR SEQ ID NO:80:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:80:

TCCAGCCTGT CCAGATGGTG TGTGAGTTTT GTCACAA 37

(2) INFORMATION FOR SEQ ID NO:81:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:81:

CTAACTCGAG AGTACTGTAT GCATGGTTCG AGATGAACAA AGATTCTGAG GCTGCAGCTC    60

CAGCCTGTCC AGATGG    76

( 2 ) INFORMATION FOR SEQ ID NO:82:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:82:

CTAACTCGAG AGTACTGTAT    20

( 2 ) INFORMATION FOR SEQ ID NO:83:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:83:

TCCAGCCTGT CCAGATGGAC ACTCTCCCCT GTTGAA    36

( 2 ) INFORMATION FOR SEQ ID NO:84:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:84:

GTACAGTGGA AGGTGGAT    18

( 2 ) INFORMATION FOR SEQ ID NO:85:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:85:

CATGCGGCCG ATTTAGGATC TTTATCGACG A    31

( 2 ) INFORMATION FOR SEQ ID NO:86:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:86:

AACATCCAGT TGGTGCAGTC TG 22

( 2 ) INFORMATION FOR SEQ ID NO:87:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:87:

GAGGAGACGG TGACCGTGGT 20

( 2 ) INFORMATION FOR SEQ ID NO:88:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:88:

GACATCAAGA TGACCCAGT 19

( 2 ) INFORMATION FOR SEQ ID NO:89:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:89:

GTTTGATTTC AAGCTTGGTG C 21

( 2 ) INFORMATION FOR SEQ ID NO:90:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:90:

ACTTCGGCCG CACCATCTGG ACAGGCTGGA G 31

( 2 ) INFORMATION FOR SEQ ID NO:91:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:91:

CGTTAGCAAT TTAACTGTGA T 21

( 2 ) INFORMATION FOR SEQ ID NO:92:

( i ) SEQUENCE CHARACTERISTICS:
    ( A ) LENGTH: 723 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:92:

| | | | | | | |
|---|---|---|---|---|---|---|
| GACATCCAGA | TGACTCAGTC | TCCATCTTCC | CTGTCTGCAT | CTGTAGGAGA | CAGAGTCACT | 60 |
| ATCACTTGCC | GGGCGAGTCA | GGACATTAAT | AGCTATTTAA | GCTGGTTCCA | GCAGAAACCA | 120 |
| GGGAAAGCTC | CTAAGACCCT | GATCTATCGT | GCAAACAGAT | TGGAATCTGG | GGTCCCATCA | 180 |
| AGGTTCAGTG | GCAGTGGATC | TGGGACAGAT | TATACTCTCA | CCATCAGCAG | CCTGCAATAT | 240 |
| GAAGATTTTG | GAATTTATTA | TTGTCAACAG | TATGATGAGT | CTCCGTGGAC | GTTCGGTGGA | 300 |
| GGCACCAAGC | TTGAGATGAA | AGGTGGCGGT | GGATCTGGTG | GAGGTGGGTC | CGGAGGTGGA | 360 |
| GGATCTGAGA | TCCAGTTGGT | GCAGTCTGGA | GGAGGCCTGG | TGAAGCCTGG | AGGGTCCGTC | 420 |
| AGAATCTCCT | GCGCAGCTTC | TGGGTATACC | TTCACAAACT | ATGGAATGAA | CTGGGTGCGC | 480 |
| CAGGCTCCAG | GAAAGGGTTT | AGAGTGGATG | GCTGGATAA | ACACCCACAC | TGGAGAGCCA | 540 |
| ACATATGCTG | ATTCTTTCAA | GGGACGGTTT | ACCTTCTCTT | TGGACGATTC | TAAGAACACT | 600 |
| GCCTATTTAC | AGATCAACAG | CCTCAGAGCC | GAGGACACGG | CTGTGTATTT | CTGTACAAGA | 660 |
| CGGGGTTACG | ACTGGTACTT | CGATGTCTGG | GGCCAAGGGA | CCACGGTCAC | CGTCTCCTCA | 720 |
| TGA | | | | | | 723 |

( 2 ) INFORMATION FOR SEQ ID NO:93:

( i ) SEQUENCE CHARACTERISTICS:
    ( A ) LENGTH: 723 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:93:

| | | | | | | |
|---|---|---|---|---|---|---|
| GAGATCCAGT | TGGTGCAGTC | TGGAGGAGGC | CTGGTGAAGC | CTGGAGGGTC | CGTCAGAATC | 60 |
| TCCTGCGCAG | CTTCTGGGTA | TACCTTCACA | AACTATGGAA | TGAACTGGGT | GCGCCAGGCT | 120 |
| CCAGGAAAGG | GTTTAGAGTG | GATGGGCTGG | ATAAACACCC | ACACTGGAGA | GCCAACATAT | 180 |
| GCTGATTCTT | TCAAGGGACG | GTTTACCTTC | TCTTTGGACG | ATTCTAAGAA | CACTGCCTAT | 240 |
| TTACAGATCA | ACAGCCTCAG | AGCCGAGGAC | ACGGCTGTGT | ATTTCTGTAC | AAGACGGGGT | 300 |
| TACGACTGGT | ACTTCGATGT | CTGGGGCCAA | GGGACCACGG | TCACCGTCTC | CTCAGGTGGC | 360 |
| GGTGGATCTG | GTGGAGGTGG | GTCCGGAGGT | GGAGGATCTG | ACATCCAGAT | GACTCAGTCT | 420 |
| CCATCTTCCC | TGTCTGCATC | TGTAGGAGAC | AGAGTCACTA | TCACTTGCCG | GGCGAGTCAG | 480 |
| GACATTAATA | GCTATTTAAG | CTGGTTCCAG | CAGAAACCAG | GAAAGCTCC | TAAGACCCTG | 540 |
| ATCTATCGTG | CAAACAGATT | GGAATCTGGG | GTCCCATCAA | GGTTCAGTGG | CAGTGGATCT | 600 |
| GGGACAGATT | ATACTCTCAC | CATCAGCAGC | CTGCAATATG | AAGATTTTGG | AATTTATTAT | 660 |
| TGTCAACAGT | ATGATGAGTC | TCCGTGGACG | TTCGGTGGAG | GCACCAAGCT | TGAGATGAAA | 720 |
| TGA | | | | | | 723 |

( 2 ) INFORMATION FOR SEQ ID NO:94:

( i ) SEQUENCE CHARACTERISTICS:

( A ) LENGTH: 51 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:94:

CGGACCCACC TCCACCAGAT CCACCGCCAC CTTTCATCTC AAGCTTGGTG C          51

( 2 ) INFORMATION FOR SEQ ID NO:95:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:95:

GACATCCAGA TGACTCAGT          19

( 2 ) INFORMATION FOR SEQ ID NO:96:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:96:

GGTGGAGGTG GGTCCGGAGG TGGAGGATCT GAGATCCAGT TGGTGCAGT          49

( 2 ) INFORMATION FOR SEQ ID NO:97:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:97:

TGTACTCGAG CCCATCATGA GGAGACGGTG ACCGT          35

( 2 ) INFORMATION FOR SEQ ID NO:98:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:98:

GGTGGAGGTG GGTCCGGAGG TGGAGGATCT          30

( 2 ) INFORMATION FOR SEQ ID NO:99:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (x i) SEQUENCE DESCRIPTION: SEQ ID NO:99:

TGTACTCGAG CCCATCATTT CATCTCAAGC TTGGTGC                                    3 7

(2) INFORMATION FOR SEQ ID NO:100:

(i) SEQUENCE CHARACTERISTICS:
     (A) LENGTH: 22 base pairs
     (B) TYPE: nucleic acid
     (C) STRANDEDNESS: single
     (D) TOPOLOGY: linear (ii) MOLECULE TYPE: DNA (xi) SEQUENCE DESCRIPTION: SEQ ID NO:100:

GAGATCCAGT TGGTGCAGTC TG                                                    2 2

(2) INFORMATION FOR SEQ ID NO:101:

(i) SEQUENCE CHARACTERISTICS:
     (A) LENGTH: 49 base pairs
     (B) TYPE: nucleic acid
     (C) STRANDEDNESS: single
     (D) TOPOLOGY: linear (ii) MOLECULE TYPE: DNA (xi) SEQUENCE DESCRIPTION: SEQ ID NO:101:

CGGACCCACC TCCACCAGAT CCACCGCCAC CTGAGGAGAC GGTGACCGT                        4 9